(12) United States Patent
Verkman et al.

(10) Patent No.: US 9,073,863 B2
(45) Date of Patent: Jul. 7, 2015

(54) CYANOQUINOLINE COMPOUNDS HAVING ACTIVITY IN CORRECTING MUTANT-CFTR PROCESSING AND INCREASING ION TRANSPORT AND USES THEREOF

(75) Inventors: Alan S. Verkman, San Francisco, CA (US); Puay-Wah Phuan, San Francisco, CA (US); Mark J. Kurth, Davis, CA (US); John Knapp, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/122,193

(22) PCT Filed: May 25, 2012

(86) PCT No.: PCT/US2012/039706
§ 371 (c)(1),
(2), (4) Date: Apr. 24, 2014

(87) PCT Pub. No.: WO2012/166654
PCT Pub. Date: Dec. 6, 2012

(65) Prior Publication Data
US 2014/0296215 A1    Oct. 2, 2014

Related U.S. Application Data

(60) Provisional application No. 61/491,119, filed on May 27, 2011.

(30) Foreign Application Priority Data

Sep. 29, 2011  (CA) ...................................... 2754237

(51) Int. Cl.
*A61K 31/44* (2006.01)
*C07D 215/54* (2006.01)
*C07D 409/12* (2006.01)
*C07D 409/14* (2006.01)
*C07D 401/12* (2006.01)

(52) U.S. Cl.
CPC ............ *C07D 215/54* (2013.01); *C07D 409/12* (2013.01); *C07D 409/14* (2013.01); *C07D 401/12* (2013.01); *A61K 31/44* (2013.01)

(58) Field of Classification Search
CPC .... A61K 31/44; C07D 215/54; C07D 401/12; C07D 409/12; C07D 409/14
USPC ......................................................... 546/159
See application file for complete search history.

(56) References Cited

U.S. PATENT DOCUMENTS

| | | | |
|---|---|---|---|
| 5,654,007 A | 8/1997 | Johnson et al. | |
| 5,785,049 A | 7/1998 | Smith et al. | |
| 5,922,354 A | 7/1999 | Johnson et al. | |
| 5,976,574 A | 11/1999 | Gordon | |
| 5,985,248 A | 11/1999 | Gordon et al. | |
| 5,993,783 A | 11/1999 | Eljamal et al. | |
| 5,997,848 A | 12/1999 | Patton et al. | |
| 6,201,107 B1 | 3/2001 | Lap-Chee et al. | |
| 8,039,462 B2 * | 10/2011 | Kelleher-Anderson | 514/218 |
| 8,785,490 B2 * | 7/2014 | Trent et al. | 514/418 |
| 2005/0282856 A1 | 12/2005 | Hennequin | |
| 2008/0318984 A1 | 12/2008 | Verkman et al. | |
| 2009/0012073 A1 | 1/2009 | Branch et al. | |

FOREIGN PATENT DOCUMENTS

| | | | |
|---|---|---|---|
| CS | 262022 | * | 2/1989 |
| WO | 0296879 | | 5/2002 |
| WO | 2005120497 | | 12/2005 |
| WO | 2006124874 | * | 11/2006 |
| WO | 2009000085 | | 12/2008 |
| WO | 2009051910 | | 4/2009 |

OTHER PUBLICATIONS

Gundla, CA 149:44599, abstract only of J Med Chem, 51(12), 2008, 3367-3377.*
Hosokawa-Muto, Antimicrob Agents Chemother, 53(2), 765-771, 2009.*
Phuan, Molecular Pharmacology, vol. 80(4), p. 683-693, 2011.*
Pedemonte et al. "Phenylglycine and Sulfonamide Correctors and Defective deltaf508 and G551D Cystic Fibrosis Transmembrane Conductance Regulator Chloride, Channel Gating," Mol. Pharmacol., 67:1797-1807 (2005).
Becker et al., "G protein-coupled receptors: In silico drug discovery in 3D," PNAS 101 (31): 11304-1309 (2004).
Egan et al., "Curcumin, a major constituent of turmeric, corrects cystic fibrosis defects," Science 304:600-602 (2004).

* cited by examiner

*Primary Examiner* — D M Seaman
(74) *Attorney, Agent, or Firm* — Rudy J. Ng; Carol L. Francis; Bozicevic, Field & Francis LLP

(57) ABSTRACT

The present disclosure provides pharmaceutical compositions, pharmaceutical preparations and methods for increasing activity of a mutant cystic fibrosis transmembrane conductance regulator protein (mutant-CFTR). The pharmaceutical compositions, pharmaceutical preparations and methods are useful for the study and treatment of disorders associated with mutant-CFTR, such as cystic fibrosis. The pharmaceutical compositions and pharmaceutical preparations may include one or more cyanoquinoline-containing compounds of the embodiments, or an analog or derivative thereof.

57 Claims, 10 Drawing Sheets

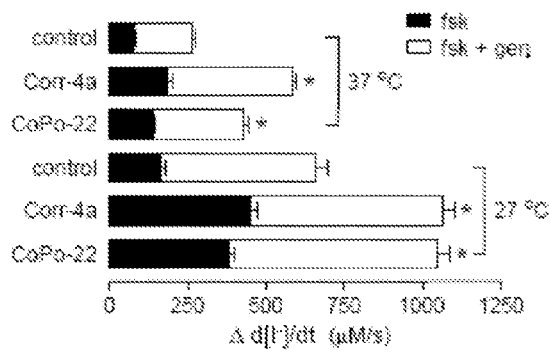 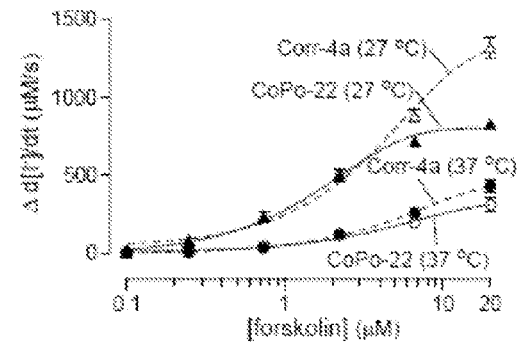
FIG. 3A    FIG. 3B
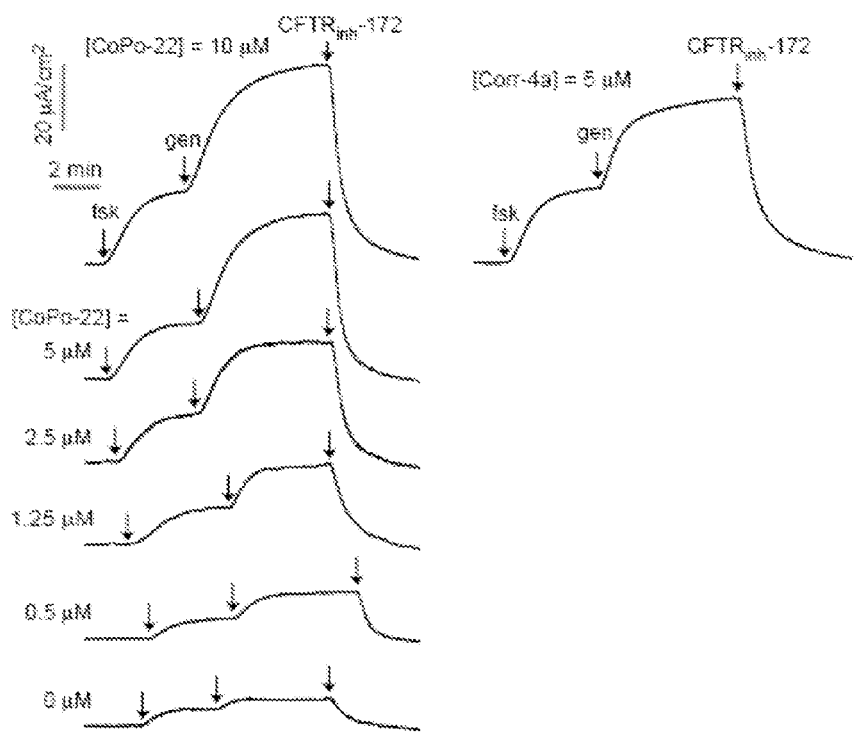
FIG. 3C

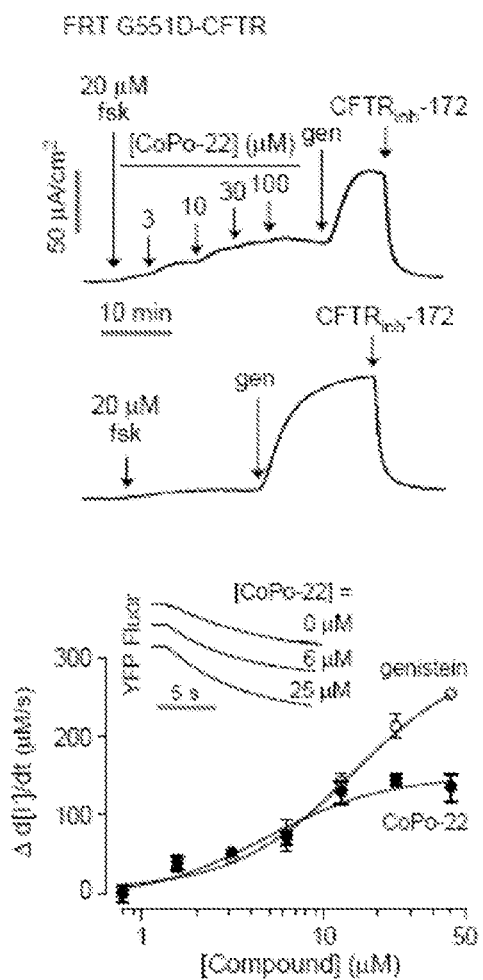
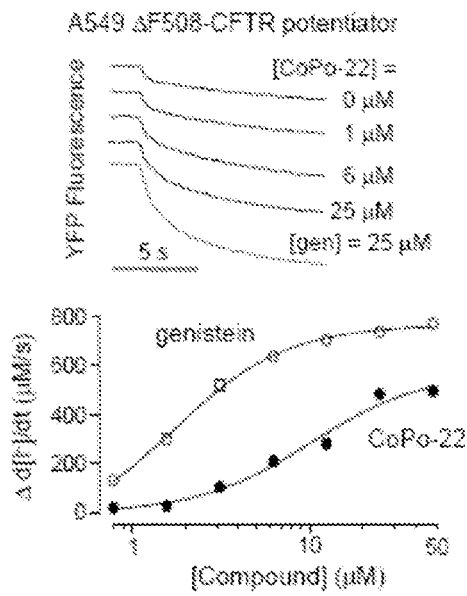
FIG. 6B
FIG. 6A

CYANOQUINOLINE COMPOUNDS HAVING ACTIVITY IN CORRECTING MUTANT-CFTR PROCESSING AND INCREASING ION TRANSPORT AND USES THEREOF

CROSS-REFERENCE TO RELATED APPLICATIONS

Pursuant to 35 U.S.C. §119(e), this application claims priority to U.S. Provisional Patent Application Ser. No. 61/491,119, filed May 27, 2011, and also claims priority pursuant to 35 U.S.C. §119(a) to Canadian Patent Application No. 2,754,237, filed Sep. 29, 2011, each of which applications are incorporated herein by reference in their entirety.

STATEMENT REGARDING FEDERALLY SPONSORED RESEARCH

This invention was made with government support under grant nos. DK072517, HL73856, DK86125, DK35124, EB00415 and EY13574 awarded by the National Institutes of Health and grant no. DK075302 awarded by the Cystic Fibrosis Foundation (A.S.V.) and the National Institutes of Health. The government has certain rights in the invention.

INTRODUCTION

The cystic fibrosis transmembrane conductance regulator protein (CFTR) is a cAMP activated chloride ion (Cl$^-$) channel responsible for Cl$^-$ transport. CFTR is expressed in epithelial cells in mammalian airways, intestine, pancreas and testis. It is there where CFTR provides a pathway for the movement of Cl$^-$ ions across the apical membrane and a key point at which to regulate the rate of transepithelial salt and water transport. Hormones, such as a β-adrenergic agonist, or toxins, such as cholera toxin, lead to an increase in cAMP, activation of cAMP-dependent protein kinase, and phosphorylation of the CFTR Cl$^-$ channel, which causes the channel to open. An increase in the concentration of Ca$^{2+}$ in a cell can also activate different apical membrane channels. Phosphorylation by protein kinase C can either open or shut Cl$^-$ channels in the apical membrane.

Dysfunction of CFTR is associated with a wide spectrum of disease, including cystic fibrosis (CF) and with some forms of male infertility, polycystic kidney disease and secretory diarrhea. CF is a hereditary disease that mainly affects the lungs and digestive system, causing progressive disability and early death. With an average life expectancy of around 31 years, CF is one of the most common life-shortening, childhood-onset inherited diseases. This disease is caused by mutation of the gene encoding CFTR, and is autosomal recessive. The most common CFTR mutation, deletion of phenylalanine-508 (ΔF508-CFTR), is present in at least one allele in about 90% of CF patients. ΔF508-CFTR causes Cl$^-$ impermeability because CFTR is not processed correctly, causing it to be retained at the endoplasmic reticulum (rather than the plasma membrane). ΔF508-CFTR also has reduced intrinsic Cl$^-$ conductance relative to wildtype CFTR.

SUMMARY

The present disclosure provides compositions, pharmaceutical preparations and methods for increasing activity (e.g., ion transport) of a mutant-cystic fibrosis transmembrane conductance regulator protein ("mutant-CFTR") that are useful for the study and treatment of cystic fibrosis ("CF"). The compositions and pharmaceutical preparations may include one or more compounds of the present disclosure, or an analog or derivative thereof.

The present disclosure provides a pharmaceutical composition that comprises a compound of formula (I):

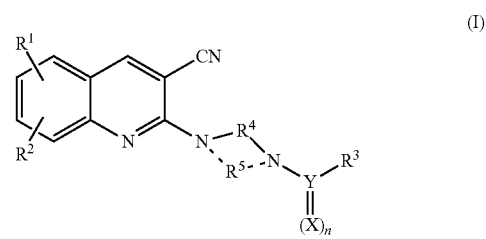

(I)

or salts, solvates, hydrates, and prodrug forms thereof, and stereoisomers thereof, wherein:

R$^1$ and R$^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl;

R$^3$ is selected from alkyl, substituted alkyl, alkylamino, alkylarylamino, aryl, substituted aryl, cycloalkyl, substituted cycloalkyl, heteroaryl, substituted heteroaryl, heterocyclyl, and substituted heterocyclyl;

R$^4$ is an alkyl or substituted alkyl;

R$^5$ is optional and, if present, is an alkyl or substituted alkyl; and

Y is C or S, with the proviso that:

when Y is C, X is either O or S, and n is 1, and when Y is S, X is O, and n is 2.

The present disclosure provides a pharmaceutical composition comprising a compound of Formula (II):

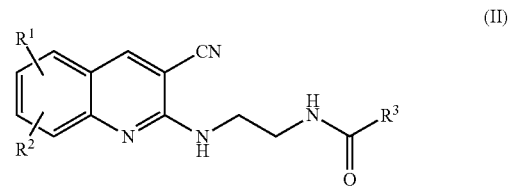

(II)

or salts, solvates, hydrates, and prodrug forms thereof, and stereoisomers thereof, wherein:

R$^1$ and R$^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and R$^3$ is selected from aryl, substituted aryl, cycloalkyl, substituted cycloalkyl, heteroaryl, substituted heteroaryl, heterocyclyl, and substituted heterocyclyl.

The present disclosure provides a pharmaceutical composition comprising a compound of Formula (III):

(III)

or salts, solvates, hydrates, and prodrug forms thereof, and stereoisomers thereof, wherein:

$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and $R^4$ and $R^5$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

The present disclosure provides a pharmaceutical composition comprising a compound of Formula (IV):

(IV)

or salts, solvates, hydrates, and prodrug forms thereof, and stereoisomers thereof, wherein:

$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and $R^6$ is selected from heteroaryl and substituted heteroaryl.

The present disclosure provides a pharmaceutical composition comprising a compound of Formula (V):

(V)

or salts, solvates, hydrates, and prodrug forms thereof, and stereoisomers thereof, wherein:

$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl;

$R^3$ is selected from alkyl, substituted alkyl, aryl, substituted aryl, cycloalkyl, substituted cycloalkyl, heteroaryl, substituted heteroaryl, heterocyclyl, and substituted heterocyclyl;

is a heterocylyl or substituted heterocyclyl; and

Y is C or S, with the proviso that when Y is C, n is 1 and when Y is S, n is 2.

The present disclosure provides a pharmaceutical composition comprising a compound of Formula (VI):

(VI)

or salts, solvates, hydrates, and prodrug forms thereof, and stereoisomers thereof, wherein:

$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and $R^3$ and $R^4$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and X is O or S.

The present disclosure provides a pharmaceutical composition comprising a compound of Formula (VII):

(VII)

or salts, solvates, hydrates, and prodrug forms thereof, and stereoisomers thereof, wherein:

$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and $R^3$ is selected from aryl, substituted aryl, cycloalkyl, substituted cycloalkyl, heteroaryl, substituted heteroaryl, heterocyclyl, and substituted heterocyclyl.

The present disclosure provides pharmaceutical compositions that include an effective amount of a disclosed compound. The pharmaceutical compositions can include at least one of a pharmaceutically acceptable carrier, a pharmaceutically acceptable diluent, a pharmaceutically acceptable excipient, and a pharmaceutically acceptable adjuvant.

The present disclosure provides methods of treating a subject having a condition associated with mutant-CFTR, which involves administering to the subject a therapeutically effective amount of a pharmaceutical composition that includes a disclosed compound. The present disclosure provides methods of increasing ion permeability of a cell producing a mutant-CFTR protein, which involves contacting the cell with an effective amount of a pharmaceutical composition that includes a disclosed compound so as to increase CFTR-mediated ion permeability of the cell.

The present disclosure provides kits containing one or more pharmaceutical compositions that include a disclosed compound, as well as methods of preparing the pharmaceutical compositions.

Advantages of the compounds and pharmaceutical compositions include improved drug like properties such as increased potency and solubility, as well as expanded diversity for generating additional corrector compounds, potentiator compound and/or compounds that have both corrector and potentiator activities. The compounds also are useful in the study of mutant-CFTR related disorders. Thus, the present disclosure addresses many unmet needs in the development and use of mutant-CFTR corrector compounds, potentiator compounds and/or compounds that have both corrector and potentiator activities. These and other objects and advantages of the present disclosure will be apparent from the detailed description below.

BRIEF DESCRIPTION OF FIGURES

FIG. 3A shows a graph of iodine influx for ΔF508-CFTR expressing FRT cells incubated at 37° C. or 27° C. with or without Compound 22 (20 μM) or Corr-4a (10 μM), according to embodiments of the present disclosure. FIG. 3B shows a graph of forskolin dose-response for experiments as in FIG. 3A, measured in the presence of genistein (50 μM), according to embodiments of the present disclosure. FIG. 3C shows graphs of short-circuit measurements showing apical membrane chloride current after incubation for 24 h at 37° C. with various concentrations of Compound 22, according to embodiments of the present disclosure.

FIGS. 6A and 6B show graphs of Compound 22 activity in G551D-CFTR expressing FRT cells and DF508-CFTR expressing A459 cells, according to embodiments of the present disclosure.

DETAILED DESCRIPTION

Figure 1A:
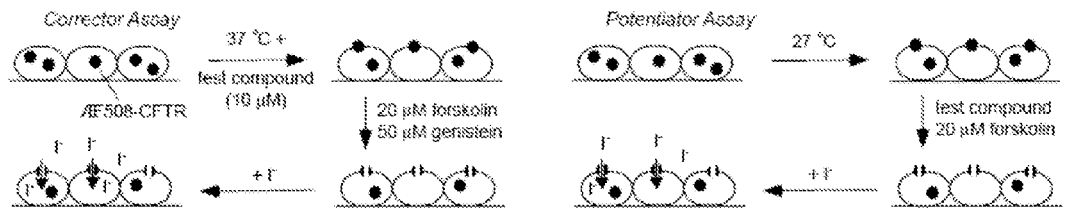
FIG. 1A shows a schematic of a high-throughput screening procedure used to identify dual-acting ΔF508-CFTR corrector-potentiator compounds, according to embodiments of the present disclosure.

The present disclosure is based on the discovery of cyanoquinoline and related compounds that correct cellular processing or folding of mutant cystic fibrosis transmembrane conductance regulator protein ("mutant-CFTR") with high nanomolar potency. The cyanoquinoline and related compounds may also increase ion transport mediated by mutant-CFTR (e.g., ΔF508-CFTR). The cyanoquinoline and related compounds exhibit a broad range of one or more other properties that find use in the study and treatment of disorders related to mutant-CFTR, such as cystic fibrosis ("CF").

The compounds share a cyanoquinoline core which includes a cyanoquinoline bicyclic structure (e.g., 3-cyanoquinoline) that can accommodate attachment of functionalities at various positions on the core ring.

By exploiting the chemical and structural aspects in the design, and synthesis and screening of compound libraries of the present disclosure, features for optimization of compounds containing a cyanoquinoline core structural motif have been identified. The compounds of the present disclosure include one or more of such features so as to impart a pharmacological or biological property that benefits the compound's manufacture, handling, potency, selectivity, and/or pharmacokinetic parameters. The present disclosure also includes compounds with features useful in the study of mutant-CFTR.

As such, the present disclosure provides novel compounds, compositions and pharmaceutical preparations that correct cellular processing or folding of mutant-CFTR (e.g., ΔF508-CFTR) and/or increase ion transport mediated by mutant-CFTR (e.g., ΔF508-CFTR). The present disclosure also features methods of use of such compositions in the treatment of a subject for CF, as well as increasing activity of mutant-CFTR in a cell, e.g., by correcting cellular processing or folding of mutant-CFTR and/or by increasing ion transport by mutant-CFTR, as well as kits and compound libraries useful for the study and treatment of CF.

Before the present invention and specific exemplary embodiments of the present disclosure are described, it is to be understood that the present disclosure is not limited to particular embodiments described, as such may, of course, vary. It is also to be understood that the terminology used herein is for the purpose of describing particular embodiments only, and is not intended to be limiting, since the scope of the present invention will be defined only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the embodiments. The upper and lower limits of these smaller ranges may independently be included in the smaller ranges is also encompassed within the embodiments, subject to any specifically excluded limit in the stated range. Where the stated range includes one or both of the limits, ranges excluding either both of those included limits are also included in the embodiments.

Unless defined otherwise, all technical and scientific terms used herein have the same meaning as commonly understood by one of ordinary skill in the relevant art. Although any methods and materials similar or equivalent to those described herein can also be used in the practice or testing of embodiments of the present disclosure, exemplary methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior invention. Further, the dates of publication provided may be different from the actual publication dates which may need to be independently confirmed.

It must be noted that as used herein and in the appended claims, the singular forms "a", "and", and "the" include plural referents unless the context clearly dictates otherwise. Thus, for example, reference to a "compound" includes a plurality of such compounds and equivalents thereof known to those skilled in the art, and so forth.

Terms

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. By way of non-limiting example, such substituents may include e.g. halo (such as fluoro, chloro, bromo), —CN, —CF$_3$, —OH, —OCF$_3$, C$_{2-6}$ alkenyl, C$_{3-6}$ alkynyl, C$_{1-6}$ alkoxy, aryl and di-C$_{1-6}$ alkylamino.

"Acyl" refers to a radical —C(O)R, where R is hydrogen, alkyl, cycloalkyl, cycloheteroalkyl, aryl, arylalkyl, heteroalkyl, heteroaryl or heteroarylalkyl as defined herein. Representative examples include, but are not limited to, formyl, acetyl, cyclohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, cycloheteroalkyl, aryl, arylalkyl, heteroalkyl, heteroaryl, heteroarylalkyl and R is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)H, —OC(O)-alkyl, —OC(O)-aryl or —OC(O)-cycloalkyl and the like.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups may have from 1 or 2 to 6 or 12 carbon atoms. The simplest aliphatic compound is methane and its chemically bonded form methyl (e.g., CH$_4$, CH$_3$—, —CH$_2$—, —CH(R)—, —C(R$_i$)(R$_{ii}$)—). Aliphatics include saturated and unsaturated compounds. Lower aliphatics typically refer to shorter aliphatic compounds having from 1 to 6 carbon atoms.

"Alkanoyl" or "acyl" as used herein refers to the group —C(O)H or —C(O)-alkyl.

"Alkenyl" refers to monovalent olefinically unsaturated hydrocarbyl groups having up to 11 carbon atoms, such as from 2 to 8 carbon atoms, or from 2 to 6 carbon atoms, which can be straight-chained or branched and having at least 1, such as from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), and the like.

"Alkenylene" refers to divalent olefinically unsaturated hydrocarbyl groups having up to 11 carbon atoms, such as from 2 to 6 carbon atoms, which can be straight-chained or branched and having at least 1, such as from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkoxy" refers to the group —O-alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxyamino" refers to a radical —N(H)O-alkyl or —N(H)O-cycloalkyl as defined herein.

"Alkoxycarbonyl" refers to a radical —C(O)-alkoxy where alkoxy is as defined herein.

"Alkoxycarbonylamino" refers to the group —NRC(O) OR' where R is hydrogen, alkyl, aryl or cycloalkyl, and R' is alkyl or cycloalkyl.

"Alkyl" refers to monovalent saturated aliphatic hydrocarbyl groups particularly having up to 11 carbon atoms, such as from 1 to 8 carbon atoms, or a lower alkyl having from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Alkylamino" refers to a radical alkyl-NRR', wherein each of R and R' are independently selected from hydrogen, alkyl or cycloalkyl.

"Alkylarylamino" refers to a radical —NRR' where R represents an alkyl or cycloalkyl group and R' is an aryl as defined herein.

"Alkylene" refers to divalent saturated aliphatic hydrocarbyl groups particularly having up to 11 carbon atoms, such as from 1 to 6 carbon atoms, which can be straight-chained or branched. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Alkylthio" refers to a radical —S-alkyl or —S-cycloalkyl group as defined herein that may be optionally substituted as defined herein. Representative examples include, but are not limited to, methylthio, ethylthio, propylthio, butylthio, and the like.

"Alkynyl" refers to acetylenically unsaturated hydrocarbyl groups particularly having up to 11 carbon atoms, such as from 2 to 6 carbon atoms, which can be straight-chained or branched and having at least 1, such as from 1 to 2 sites of alkynyl unsaturation. Particular non-limiting examples of alkynyl groups include acetylenic, ethynyl (—C≡CH), propargyl (—$CH_2$C≡CH), and the like.

"Amide" refers to the radical —NHC(O)— or —C(O)$NH_2$.

"Amino" refers to the radical —$NH_2$.

"Aminocarbonyl" refers to the group —C(O)NRR where each R is independently hydrogen, alkyl, aryl or cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalkyl, or where the R groups are joined to form an alkylene group.

"Aralkyl" or "arylalkyl" refers to an alkyl group, as defined above, substituted with one or more aryl groups, as defined above.

"Aromatic" refers to a mono- or polycyclic aromatic hydrocarbon group, and may include one or more heteroatoms in the aromatic ring or ring system termed a heteroaromatic. Also referred to as "aromatic ring" or "aromatic ring system." Simple aromatics include from 3 to 14 carbons, examples of which include arsindole, benzene, benzothiophene, benzo[c]thiophene, benzimidazole, benzoxazole, benzisoxazole, benzothiazole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, purine, quinazoline, quinoline, quinolizine, quinoxaline, tetrazole, thiadiazole, thiazole, thiophene, triazole, [2,4,6]triazine and xanthene, as well as fused ring systems such as acridine, anthracene, cinnoline, naphthalene, naphthyridine, quinoline, isoquinoline, quinoxaline and quinazoline.

"Aryl" refers to any functional group or substituent derived from a simple aromatic ring by removal of a hydrogen atom from a carbon atom of a parent aromatic ring system. Typical aryl groups include from 6 to 14 carbon atoms. Examples include the radicals of arsindole, benzene, benzothiophene, benzo[c]thiophene, benzimidazole, benzoxazole, benzisoxazole, benzothiazole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, purine quinazoline, quinoline, quinolizine, quinoxaline, tetrazole, thiadiazole, thiazole, thiophene, triazole, [2,4,6]triazine and xanthene, as well as fused ring systems such as acridine, anthracene, cinnoline, naphthalene, naphthyridine, quinoline, isoquinoline, quinoxaline and quinazoline. Examples of radicals denoted by the term "aryl" that are of interest include: phenyl, furyl, pyrrolyl, pyrrolidinyl, imidazolyl, isoxazolyl, triazolyl, thiadiazolyl, oxadiazolyl, tetrazolyl, thiatriazolyl, thienyl, oxatriazolyl, oxazinyl, pyridyl, pyrimidyl, pyrazinyl, pyridazinyl, quinolinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

"Arylalkyloxy" refers to an —O-arylalkyl radical where arylalkyl is as defined herein.

"Arylamino" refers to the group aryl-NRR', wherein each of R and R' are independently selected from hydrogen, aryl and heteroaryl.

"Aryloxy" refers to —O-aryl groups wherein "aryl" is as defined herein.

"Arylsulfonyl" refers to a radical —S(O)$_2$R where R is an aryl or heteroaryl group as defined herein.

"Azide" refers to $N_3$ or its radical —$N_3$ (also referred to as "azido").

"Carbamoyl" refers to the radical —C(O)N(R)$_2$ where each R group is independently hydrogen, alkyl, cycloalkyl or aryl, as defined herein, which may be optionally substituted as defined herein.

"Carbonyl" refers to the radical —C(O)—.

"Carboxy" refers to the radical —C(O)OH (also referred to as "carboxyl").

"Cyano" refers to the radical —CN.

"Cycloalkenyl" refers to cyclic hydrocarbyl groups having from 3 to 10 carbon atoms and having a single cyclic ring or multiple condensed rings, including fused and bridged ring systems and having at least one, such as from 1 to 2 sites of olefinic unsaturation. Such cycloalkenyl groups include, by way of example, single ring structures such as cyclohexenyl, cyclopentenyl, cyclopropenyl, and the like.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 6 alkyl groups. Such cycloalkyl groups include, by way of example, single ring structures such as cyclopropyl, cyclobutyl, cyclopentyl, cyclohexyl, cyclooctyl, 1-methylcyclopropyl, 2-methylcyclopentyl, 2-methylcyclooctyl, and the like, and multiple ring structures such as adamantanyl, and the like.

"Cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, which can be optionally substituted with one or more groups selected from acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$—, aryl-S(O)$_2$—, and the like. Substituting groups include carbonyl or thiocarbonyl which provide, for example, lactam and urea derivatives. In the examples, M is $CR^7$, $NR^3$, O, or S; Q is O, $NR^3$ or S.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Diamino" means a radical —NRN— where R represents an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein. The nitrogens of the diamino group may independently be secondary nitrogens or tertiary nitrogens, where if the nitrogen is a tertiary nitrogen, then the tertiary nitrogen may be a substituted amino group as defined herein.

"Halo" or "halogen" refers to fluoro, chloro, bromo and iodo. In some instances, halo groups can be fluoro, chloro or bromo.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described herein such as alkyl, e.g. heteroalkyl, cycloalkyl, e.g. cycloheteroalkyl, aryl, e.g. heteroaryl, cycloalkenyl, e.g., cycloheteroalkenyl, and the like having from 1 to 5, such as from 1 to 3 heteroatoms.

"Heterocycle," "heterocyclic," "heterocycloalkyl," and "heterocyclyl" refer to a saturated or unsaturated group having a single ring or multiple condensed rings, including fused, bridged and spiro ring systems, and having from 3 to 15 ring atoms, including 1 to 4 hetero atoms. These hetero atoms are selected from nitrogen, oxygen, or sulfur, where, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Hydroxyl" refers to the radical —OH.

"Nitro" refers to the radical —NO$_2$.

"Phenyl" (often abbreviated as -Ph) is the aryl form of benzene with the functional group, and has the formula —C$_6$H$_5$, where the six carbon atoms are arranged in an aromatic ring structure.

"Substituted" refers to a group in which one or more hydrogen atoms are each independently replaced with the same or different substituent(s). Typical substituents include, but are not limited to —X, —$R^{14}$, —O—, =O, —$OR^{14}$, —$SR^{14}$, —S$^-$, =S, —$NR^{14}R^{15}$, =$NR^{14}$, —$CX_3$, —$CF_3$, —CN, —OCN, —SCN, —NO, —NO$_2$, =N$_2$, —N$_3$, —S(O)$_2$, —S(O)$_2$O$^-$, —S(O)$_2$OH, —S(O)$_2$$R^{14}$, —OS(O$_2$)O$^-$, —OS(O)$_2$$R^{14}$, —P(O)(O—)$_2$, —P(O)($OR^{14}$)(O$^-$), —P(O)($OR^{14}$)($OR^{15}$), —C(O)$R^{14}$, —C(S)$R^{14}$, —C(O)$OR^{14}$, —C(O)$NR^{14}R^{15}$, —C(O)O$^-$, —C(S)$OR^{14}$, —$NR^{16}$C(O)$NR^{14}R^{15}$, —$NR^{16}$C(S)$NR^{14}R^{15}$, —$NR^{17}$C($NR^{16}$)$NR^{14}R^{15}$ and —C($NR^{16}$)$NR^{14}R^{15}$, where each X is independently a halogen, and where "$R^{14}$", "$R^{15}$", "$R^{16}$", and "$R^{17}$" are independently hydrogen, alkyl, substituted alkyl, aryl, arylalkyl, cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR^{18}R^{19}$, —C(O)$R^{18}$ or —S(O)$_2$$R^{18}$ or optionally $R^{18}$ and $R^{19}$ together with the atom to which they are both attached form a cycloheteroalkyl or substituted cycloheteroalkyl ring, and where "$R^{18}$", "$R^{19}$", and "$R^{22}$" are each independently selected from the group consisting of hydrogen, substituted or unsubstituted alkyl, substituted or unsubstituted aryl, substituted or unsubstituted arylalkyl, substituted or unsubstituted cycloalkyl, substituted or unsubstituted cycloheteroalkyl, substituted or unsubstituted heteroalkyl, substituted or unsubstituted heteroaryl, and substituted or unsubstituted heteroarylalkyl.

"Substituted aliphatic" includes those groups recited in the definition of "substituted" herein, and refers to aliphatic group having 1 or more substituents, for instance from 1 to 5 substituents, such as from 1 to 3 substituents, which in some instances are selected from acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$- and aryl-S(O)$_2$—, and the like.

"Substituted alkenyl" includes those groups recited in the definition of "substituted" herein, and refers to an alkenyl group having 1 or more substituents, for instance from 1 to 5 substituents, such as from 1 to 3 substituents, which in some instances are selected from acyl, acylamino, acyloxy, aliphatic, substituted aliphatic, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—, and the like.

"Substituted alkoxy" includes those groups recited in the definition of "substituted" herein, and refers to an alkoxy group having 1 or more substituents, for instance from 1 to 5 substituents, such as from 1 to 3 substituents, which in some instances are selected from acyl, acylamino, acyloxy, aliphatic, substituted aliphatic, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—, and the like.

"Substituted alkyl" includes those groups recited in the definition of "substituted" herein, and refers to an alkyl group having 1 or more substituents, for instance from 1 to 5 substituents, such as from 1 to 3 substituents, which in some instances are selected from acyl, acylamino, acyloxy, aliphatic, substituted aliphatic, alkenyl, substituted alkenyl, alkynyl, substituted alkynyl, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—, and the like.

"Substituted alkylene" includes those groups recited in the definition of "substituted" herein, and refers to an alkylene group having 1 or more substituents, for instance from 1 to 5 substituents, such as from 1 to 3 substituents, which in some instances are selected from acyl, acylamino, acyloxy, aliphatic, substituted aliphatic, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$- and aryl-S(O)$_2$—, and the like.

"Substituted alkynyl" includes those groups recited in the definition of "substituted" herein, and refers to an alkynyl group having 1 or more substituents, for instance from 1 to 5 substituents, such as from 1 to 3 substituents, which in some instances are selected from acyl, acylamino, acyloxy, aliphatic, substituted aliphatic, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—, and the like.

"Substituted amino" includes those groups recited in the definition of "substituted" herein, and refers to the group —N(R)$_2$ where each R is independently selected from hydrogen, aliphatic, substituted aliphatic, alkyl, substituted alkyl, alkenyl, substituted alkenyl, alkynyl, substituted alkynyl, aryl, substituted aryl, cycloalkyl, substituted cycloalkyl, and the like, and where both R groups are joined to form an alkylene group.

"Substituted aryl" includes those groups recited in the definition of "substituted" herein, and refers to an aryl group that may optionally be substituted with 1 or more substituents, for instance from 1 to 5 substituents, such as from 1 to 3 substituents, or 1 to 2 substituents, which in some instances are selected from acyl, acylamino, acyloxy, aliphatic, substituted aliphatic, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—, and the like. Substituted aryl substituents may include heteroaryls and substituted heteroaryls in which one or more carbon atoms of the aromatic ring system is replaced by N, O or S. Examples of substituents include from one to three halo, trihalomethyl, amino, protected amino, amino salts, mono-substituted amino, disubstituted amino, carboxy, protected carboxy, carboxylate salts, hydroxy, protected hydroxy, salts of a hydroxy group, lower alkoxy, lower allylthio, alkyl, substituted alkyl, cycloallyl, substituted cycloalkyl, (cycloallyl)alkyl, substituted (cycloalkyl)allyl, phenyl, substituted phenyl, phenylalkyl, and (substituted phenyl)allyl, and the like. Substituents for the heteroaryl group are as defined herein, or in the case of trihalomethyl, can be trifluoromethyl, trichloromethyl, tribromomethyl, or triiodomethyl, as used in conjunction with the above substituents for heteroaryl.

"Substituted cycloalkenyl" includes those groups recited in the definition of "substituted" herein, and refers to a cycloalkenyl group having 1 or more substituents, for instance from 1 to 5 substituents, such as from 1 to 3 substituents, which in some instances are selected from acyl, acylamino, acyloxy, aliphatic, substituted aliphatic, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—, and the like.

"Substituted cycloalkyl" includes those groups recited in the definition of "substituted" herein, and refers to a cycloalkyl group having 1 or more substituents, for instance from 1 to 5 substituents, such as from 1 to 3 substituents, which in some instances are selected from acyl, acylamino, acyloxy, aliphatic, substituted aliphatic, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—, and the like.

"Substituted phenyl" includes those groups recited in the definition of "substituted" herein, and refers to a phenyl group that may optionally be substituted with 1 or more substituents, for instance from 1 to 5 substituents, such as from 1 to 3 substituents. Substituents of the phenyl group include those selected from acyl, acylamino, acyloxy, alkenyl, substituted alkenyl, aliphatic, substituted aliphatic, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—, and the like. Substituents of the phenyl group include those that form a fused phenyl ring system in which a heterocycle ring is fused to the phenyl ring, and the heterocycle contains one or more heteroatoms independently selected from N, O and S. Substituents of the phenyl group may be selected from halogen, hydroxy, protected hydroxy, amino, protected amino, amide, protected amide, thiol, protected thiol, cyano, nitro, azido, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ allyl)carboxamide, N,N-di($C_1$ to $C_6$ allyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results. Examples of substituted phenyls include a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2,3, or 4-hydroxyphenyl, 2,4-dihydroxyphenyl, the protected-hydroxy derivatives thereof and the like; a nitrophenyl group such as 2,3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(iso-propyl)phenyl, 2,3, or 4-ethylphenyl, 2, 3 or 4-(n-propyl)phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-dibrotected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or dim-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like "Substituted thioalkoxy" includes those groups recited in the definition of "substituted" herein, and refers to a thioalkoxy group having 1 or more substituents, for instance from 1 to 5 substituents, such as from 1 to 3 substituents, which in some instances are selected from acyl, acylamino, acyloxy, aliphatic, substituted aliphatic, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—, and the like.

"Sulfanyl" refers to the radical —SH. "Substituted sulfanyl" refers to a radical such as —SR wherein R is any substituent described herein.

"Sulfone" refers to the group —SO$_2$R. In some embodiments, R is selected from H, lower alkyl, alkyl, aryl and heteroaryl.

"Sulfonyl" refers to the divalent radical —S(O$_2$)—. "Substituted sulfonyl" refers to a radical such as R—(O$_2$)S— wherein R is any substituent described herein. "Aminosulfonyl" refers to the radical H$_2$N(O$_2$)S—, and "substituted aminosulfonyl" refers to a radical such as R$_2$N(O$_2$)S— wherein each R is independently any substituent described herein.

"Thioalkoxy" refers to the group —S-alkyl.
"Thioaryloxy" refers to the group —S-aryl.
"Thioketo" refers to the group =S.
"Thiol" refers to the group —SH.

One having ordinary skill in the art will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

A "mutant cystic fibrosis transmembrane conductance regulator protein" or "mutant-CFTR" is the protein that results from a mutation, e.g., deletion mutation, insertion mutation, or point (substitution) mutation of the CFTR gene product relative to wildtype. A mutant-CFTR refers to a dysfunctional CFTR as compared to a functional (e.g., wildtype) CFTR, where the dysfunction can encompass one or more of the following: (i) aberrant CFTR production (e.g., at the level of transcription or translation); (ii) aberrant folding and/or trafficking; (iii) abnormal regulation of conductance; (iv) decreases in chloride conductance; (v) reduction in synthesis; and the like. A "mutant-CFTR gene" is a gene, or coding sequence, which encodes a mutant-CFTR. For the purposes of this application, the terms "genome" and "gene" are used interchangeably, e.g. "genome that encodes mutant-CFTR" and "gene that encodes mutant-CFTR".

A "gating defective mutant cystic fibrosis transmembrane conductance regulator protein" or "gating defective mutant-CFTR" is a mutant-CFTR that is present on the cell surface and is defective in gating of ions through the channel (e.g., regulation of ion transport). Thus, as used herein a "gating defective mutant-CFTR" encompasses dysfunctions associated with abnormal regulation of conductance and/or decreases in chloride conductance.

A "mutant-CFTR protein-mediated condition" means any condition, disorder or disease, or symptom of such condition, disorder, or disease that results from or is correlated to the presence of a mutant-CFTR, e.g., ΔF508-CFTR, e.g., chloride ion impermeability caused by reduced activity of ΔF508-CFTR in ion transport relative to a wildtype CFTR. A "mutant-CFTR protein-mediated condition" encompasses conditions in an affected subject which are associated with the presence of a ΔF508-CFTR mutation on at least one allele, thus including subjects that carry a ΔF508-CFTR mutation on both alleles as well as heterozygous subjects having two different mutant forms of CFTR, e.g., a subject with one copy of ΔF508-CFTR and a copy of different form of CFTR, e.g., a non-mutant CFTR or a different mutant CFTR. Such conditions, disorders, diseases, or symptoms thereof are treatable by specific activation of mutant-CFTR activity, e.g., activation of mutant-CFTR ion transport. ΔF508-CFTR is correlated to the presence of cystic fibrosis (CF), and a description of this disease, including its symptoms, is found in Accession No. 602421 (entitled cystic fibrosis transmembrane conductance regulator; CFTR), and Accession No. 2 19700 (entitled Cystic fibrosis; CF) of the Online Mendelian Inheritance of Man database, as found at the world wide website of the National Institute of Health at ncbi.nlm.nih.gov. Symptoms of mutant-CFTR protein-mediated conditions include meconium ileus, liver disease including biliary tract obstruction and stenosis, pancreatic insufficiency, pulmonary disease including chronic *Pseudomonas aeruginosa* infections and other infections of the lung, infertility associated with abnormal vas deferens development or abnormal cervical mucus, and carcinoma including adenocarcinoma. In certain embodiments, subjects that have a mutant-CFTR protein-mediated condition are homozygous for a gene encoding a ΔF508-CFTR protein. In certain embodiments, subjects that have a mutant-CFTR protein-mediated condition are heterozygous for a gene encoding a ΔF508-CFTR protein.

A "ΔF508-cystic fibrosis transmembrane conductance regulator protein" or "ΔF508-CFTR" is the protein that results from the deletion of a phenylalanine residue at amino acid position 508 of the CFTR gene product. A "ΔF508-CFTR gene" is a gene, or coding sequence, which encodes ΔF508-CFTR. A ΔF508-CFTR gene usually results from deletion of three nucleotides corresponding to the phenylalanine residue at amino acid position 508 of the encoded CFTR gene product. For the purposes of this application, the terms "genome" and "gene" are used interchangeably, e.g. "genome that encodes ΔF508-CFTR and "gene that encodes ΔF508-CFTR". For an example of a gene that encodes ΔF508-CFTR, see, e.g. WO 91102796.

A "mutant-CFTR activator" as used herein is a compound that increases the level of ion transport by a mutant-CFTR relative to ion transport in the absence of the compound, for example with respect to transport of chloride ions. CFTR activators of the embodiments are those that are specific mutant-CFTR activators, e.g., compounds that activate mutant-CFTR activity rather than affecting CFTR cellular misprocessing. Mutant-CFTR activators are usually high-affinity mutant-CFTR activators, e.g., have an affinity for mutant-CFTR of at least about one micromolar, about one to five micromolar, about 200 nanomolar to one micromolar, about 50 nanomolar to 200 nanomolar, or below 50 nanomolar.

A "gating defective mutant-CFTR activator" as used herein is a compound that increases the level of ion transport by a gating defective mutant-CFTR relative to ion transport in the absence of the compound, for example with respect to transport of chloride ions. CFTR activators of the embodiments are those that are specific gating defective mutant-CFTR activators, e.g., compounds that activate gating defective mutant-CFTR activity rather than affecting, for example, CFTR cellular misprocessing. Gating defective mutant-CFTR activators may be high-affinity activators of gating defective mutant-CFTRs, e.g., have an affinity for a gating defective mutant-CFTR (e.g., ΔF508-CFTR, G551D-CFTR, G1349D-CFTR, or D1152H-CFTR) of 20 micromolar or less, such as 15 micromolar or less, or 10 micromolar or less, or 5 micromolar or less, or one micromolar or less, for example from one to five micromolar, or from 50 nanomolar to one micromolar, or from 50 nanomolar to 200 nanomolar, or 50 nanomolar or less.

A "ΔF508-CFTR activator" as used herein is a compound that increases the level of ion transport by ΔF508-CFTR relative to ion transport in the absence of the compound, for example with respect to transport of chloride ions. CFTR activators of the embodiments are those that are specific ΔF508-CFTR activators, e.g., compounds that activate ΔF508-CFTR activity rather than affecting CFTR cellular misprocessing. ΔF508-CFTR activators may be high-affinity ΔF508-CFTR activators, e.g., have an affinity for ΔF508-CFTR of 20 micromolar or less, such as 15 micromolar or less, or 10 micromolar or less, or 5 micromolar or less, or one micromolar or less, for example from one to five micromolar, or from 50 nanomolar to one micromolar, or from 50 nanomolar to 200 nanomolar, or 50 nanomolar or less.

As used herein and in the cystic fibrosis field a "potentiator" or "mutant-CFTR potentiator" refers to a compound that increases a basal level of ion transport by a mutant-CFTR (e.g., ΔF508-CFTR, G551D-CFTR, G1349D-CFTR, or D1152H-CFTR), where the mutant CFTR (in the absence of the compound) exhibits aberrantly low levels of ion transport relative to wildtype CFTR. As such, a "mutant-CFTR potentiator" refers to a potentiator compound that provides for increased level of ion transport by a mutant-CFTR relative to ion transport capability of the mutant-CFTR in the absence of the compounds.

As used herein and in the cystic fibrosis field a "corrector" or "mutant-CFTR corrector" is a compound that increases the level of ion transport by a mutant-CFTR relative to ion transport in the absence of the compound by correcting the underlying defect of the CFTR polypeptide, e.g., a defect that results from post-translational mis-processing (e.g., misfolding). CFTR correctors of the embodiments are those that facilitate correction of specific mutant-CFTRs. Mutant-CFTR correctors may exhibit high affinity for one or more mutant-CFTRs, e.g., have an affinity for mutant-CFTR of 20 micromolar or less, such as 15 micromolar or less, or 10 micromolar or less, or 5 micromolar or less, or one micromolar or less, for example from one to five micromolar, or from 50 nanomolar to one micromolar, or from 50 nanomolar to 200 nanomolar, or 50 nanomolar or less.

As used herein, a "corrector-potentiator" or "mutant-CFTR corrector-potentiator" is a compound that exhibits both mutant-CFTR corrector and potentiator activity as described herein, and may exhibit high affinity for one or more mutant-CFTRs, e.g., have an affinity for mutant-CFTR of 20 micromolar or less, such as 15 micromolar or less, or 10 micromolar or less, or 5 micromolar or less, or one micromolar or less, for example from one to five micromolar, or from 50 nanomolar to one micromolar, or from 50 nanomolar to 200 nanomolar, or 50 nanomolar or less.

The term "analog" or "analogue" refers to without limitation any compound which has structural similarity to the parent compound and would be expected, by one skilled in the art, to exhibit the same or similar utility as the parent compound.

The term "derivative" refers to without limitation any compound which has a structure derived from the structure of the parent compound and whose structure is sufficiently similar to those disclosed herein and based upon that similarity, would be expected, by one skilled in the art, to exhibit the same or similar activities and utilities as the parent compound.

The term "effective amount" of a compound as provided herein is intended to mean a sufficient amount of the compound to provide the desired utility. The term "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated. Thus, as will be pointed out below, the exact amount required will vary from subject to subject, depending on the species, age, and general condition of the subject, the severity of the condition or disease that is being treated, the particular compound used, its mode of administration, and the like. Thus, it may not be possible to specify an exact "effective amount." However, an appropriate effective amount may be determined by one of ordinary skill in the art using only routine experimentation.

"Functional group" refers to atoms or small groups of atoms (two to four) that exhibit a characteristic reactivity when treated with certain reagents, and are attached to the carbon backbone of organic molecules. The same functional group will undergo the same or similar chemical reaction(s) regardless of the size of the molecule it is a part of. Examples of functional groups include halogen, hydroxy, carboxy, ester, thioester, amino, oxime, hydrazone, thiol, azide, nitro, nitroso, aldehyde, ketone, and the like. The functional groups can be protected or unprotected, activated or unactivated.

The term "in combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

The term "isolated" means that a compound which has been substantially separated from, or enriched relative to, other compounds with which it occurs in nature. "Isolated" also refers to the state of a compound separated from all or some of the components that accompany it during manufacture (e.g., chemical synthesis, recombinant expression, culture medium, and the like). Isolated compounds may be present as stereoisomers, and in particular, diastereomers as well as their racemic and resolved, enantiomerically pure forms and salts thereof. An isolated compound is substantially pure when it is at least 50% to 60%, by weight, free from organic molecules with which it is naturally associated or with which it is associated during manufacture. In certain instances, a substantially pure compound is 75% or more, or 90% or more, or 95% or more, or 99% or more, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample having a particular isomer of a compound of interest. Purity can be measured by any appropriate method, e.g., chromatography, mass spectroscopy, HPLC analysis, etc.

The term "optional" or "optionally" means that the subsequently described event, circumstance, feature or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or di-substituted with an alkyl group and situations where the heterocyclo group is not substituted with the alkyl group.

The term "organic group" and "organic radical" means any carbon containing group, including hydrocarbon groups that are classified as an aliphatic group, cyclic group, aromatic group, functionalized derivatives thereof and/or various combinations thereof.

The terms "monosubstituted" refers to group with one substituent, "disubstituted" refers to group with two substituents, "trisubstituted" refers a group with three substituents, and so forth. For example, a (monosubstituted)amino refers to an amino group with one substituent, whereas a (disubstituted)amino refers to an amino group with two substituents, and whereas a (trisubstituted)amino refers to an amino group with three substitutents. When two or more substituents are present, they can be the same or different.

The term "pharmaceutically acceptable" refers to a material that is not biologically or otherwise undesirable, i.e., the material is of a medically acceptable quality and composition that may be administered to an individual along with the selected active pharmaceutical ingredient without causing any undesirable biological effects or interacting in a deleterious manner with any of the other components of the pharmaceutical composition in which it is contained. In certain embodiments, pharmaceutically acceptable compositions do not include detectable amounts of dimethyl sulfoxide (DMSO). In certain embodiments, pharmaceutically acceptable compositions do not include solvents, such as dimethyl sulfoxide (DMSO) that may cause undesirable biological effects.

The term "pharmaceutically acceptable excipient" as used herein refers to any suitable substance which provides a pharmaceutically acceptable vehicle for administration of a compound(s) of interest to a subject. "Pharmaceutically acceptable excipient" can encompass substances referred to as pharmaceutically acceptable diluents, pharmaceutically acceptable additives and pharmaceutically acceptable carriers. For example, a "pharmaceutically acceptable excipient," "pharmaceutically acceptable diluent," "pharmaceutically acceptable carrier," and "pharmaceutically acceptable adjuvant" includes excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use, and may include both one and more than one such excipient, diluent, carrier, and adjuvant. In certain embodiments, pharmaceutically acceptable carriers do not include detectable amounts of dimethyl sulfoxide (DMSO). In certain embodiments, pharmaceutically acceptable carriers do not include solvents, such as dimethyl sulfoxide (DMSO) that may cause undesirable biological effects.

The term "physiological conditions" is meant to encompass those conditions compatible with living cells, e.g., predominantly aqueous conditions of a temperature, pH, salinity, etc. that are compatible with living cells.

The term "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, and the like. In certain embodiments, pharmaceutical compositions do not include detectable amounts of dimethyl sulfoxide (DMSO). In certain embodiments, pharmaceutical compositions do not include solvents, such as dimethyl sulfoxide (DMSO) that may cause undesirable biological effects.

The term "pharmaceutically acceptable derivatives" of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and are either pharmaceutically active or are prodrugs.

The term "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Polypeptides may be of any size, and the term "peptide" refers to polypeptides that are 8-50 residues (e.g., 8-20 residues) in length.

The term "protecting group" means a chemical group introduced into a molecule by chemical modification of a functional group in order to protect or shield the functional group from its normal chemical reactivity. Protecting groups, their addition and removal are well known (W. Green, P. G. M. Wuts, Protective Groups in Organic Synthesis, Wiley-Interscience, New York, 2005). Removal of the protecting group generates the original functional group, which may be referred to as an "unprotected group".

The term "prodrugs" means any compound that releases an active parent drug in vivo when such prodrug is administered to a mammalian subject. Prodrugs of a compound are prepared by modifying functional groups present in the compound in such a way that the modifications may be cleaved in vivo to release the parent compound. Prodrugs include compounds wherein a hydroxy, amino, or sulfhydryl group in the compound is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in the compounds, and the like.

The term "racemic" means a mixture containing approximately equal proportions of enantiomers.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on. Non-human animal models, particularly mammals, e.g. primate, murine, lagomorpha, etc. may be used for experimental investigations.

As used herein, the terms "determining," "measuring," and "assessing," and "assaying" are used interchangeably and include both quantitative and qualitative determinations.

The term "stereoisomer" means a compound with the same chemical formula and bond structure as a reference compound, but the geometrical positioning of atoms and functional groups in space differs. This class of isomers includes "enantiomers" in which different isomers are non-superimposable mirror-images of each other, and diastereomers when they are not. Enantiomers can be designated by "(+)" versus "(−)" when based on optical properties, or "(R)" versus "(S)" and or "D" versus "L" when based on geometric properties. For example, "D-enantiomer" and "L-enantiomer" refer to the enantiomers of a chiral system, based on the actual geometry of each enantiomer. In the context of amino acids, the enantiomer with geometry based on a naturally occurring amino acid is the L-enantiomer, whereas and the enantiomer based on a non-naturally occurring amino acid is the D-enantiomer. The term "diastereomer" refers to rotational or conformational stereoisomers ("rotational isomers" or "rotomers"; and "conformational isomers" or "conformers") when the isomers can interconvert by chemical bond rotations, or cis-trans isomerism ("cis-trans isomers") when this is not possible. Stereoisomers also include "tautomers" which are structural isomers of the same chemical substance that spontaneously interconvert with each other, even when pure. Thus unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

The term "treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

The term "unit dosage form" refers to physically discrete units suitable as unitary dosages for human and animal subjects, each unit containing a predetermined quantity of compounds of the embodiments calculated in an amount sufficient to produce the desired effect in association with a pharmaceutically acceptable diluent, carrier or vehicle. The specifications for the novel unit dosage forms of the embodiments depend on the particular compound employed and the effect to be achieved, and the pharmacodynamics associated with each compound in the host.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to substituted aryl-(substituted aryl)-substituted aryl.

It is further noted that the claims may be drafted to exclude any optional or alternative element. As such, this statement is intended to serve as antecedent basis for use of such exclusive terminology as "solely", "only" and the like in connection with the recitation of claim elements, or the use of a "negative" limitation.

In describing the embodiments, the structure of the compounds will be described first. Then, pharmaceutical formulations containing the compounds will be discussed, followed by a description of their methods of use, and kits.

Pharmaceutical Compositions

The present disclosure provides pharmaceutical compositions containing compounds that correct cellular processing or folding of mutant-CFTR, such as ΔF508-CFTR, and/or increase ion transport in a mutant-CFTR, such as ΔF508-CFTR, and methods of using the compounds and pharmaceutical compositions in the treatment of mutant-CFTR-mediated diseases and conditions, e.g., cystic fibrosis. For example, in some instances, the compounds correct cellular processing or folding of mutant-CFTR (e.g., mutant-CFTR correctors). In other embodiments, the compounds increase ion transport in a mutant-CFTR (e.g., mutant-CFTR potentiators). And in further embodiments, the compounds correct cellular processing or folding of mutant-CFTR and also increase ion transport in a mutant-CFTR (e.g., mutant-CFTR corrector-potentiators). Such compounds also find use in the study of CFTR ion transport, such as that of ΔF508-CFTR.

In certain embodiments, the present disclosure provides pharmaceutical compositions that include high-affinity small-molecule compounds that increase chloride ion (Cl$^-$) conductance in cellular processing and folding defective mutant-CFTRs, such as ΔF508-CFTR. In some instances, the present disclosure provides pharmaceutical compositions that include high-affinity small-molecule compounds that increase chloride ion (Cl$^-$) conductance in gating defective mutant-CFTRs, such as ΔF508-CFTR. In some cases, the present disclosure provides pharmaceutical compositions that include high-affinity small-molecule compounds that increase chloride ion (Cl$^-$) conductance in cellular processing and folding defective mutant-CFTRs, such as ΔF508-CFTR, and also increase chloride ion (Cl$^-$) conductance in gating defective mutant-CFTRs, such as ΔF508-CFTR.

In certain embodiments, the compounds of the pharmaceutical compositions include a cyanoquinoline core and multiple diversity points of substituents. For example, the cyanoquinoline compounds may have the following general structural formula:

General Cyanoquinoline Structural Formula

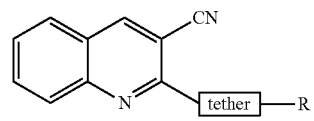

In certain embodiments, the cyanoquinoline group is a substituted or unsubstituted cyanoquinoline group. The cyanoquinoline group may be unsubstituted (e.g., substituted with only the cyano group and the tether group and no additional substituents), or may include from 1 to 5 additional substituents (e.g., substituents in addition to the cyano group and the tether group). If the cyanoquinoline is a substituted cyanoquinoline group, the substituents may be arranged in any one or more of the positions on the cyanoquinoline bicyclic ring structure that are not occupied by either the cyano group or the tether group. For example, one or more hydrogen atoms on the cyanoquinoline group may be replaced by one or more substituents. The ring atoms of the cyanoquinoline bicyclic ring structure may be numbered, such that the nitrogen is numbered as position number 1, the carbon attached to the tether group is numbered as position number 2 (i.e., carbon-2, or C-2), and the carbon attached to the cyano group is numbered as position number 3 (i.e., carbon-3, or C-3). The remaining carbons of the cyanoquinoline bicyclic ring structure may be numbered counterclockwise (excluding the bridging carbons) from the carbon attached to the cyano group (i.e., carbon-3, or C-3). Thus, for substituted cyanoquinoline groups, one or more of C-4, C-5, C-6, C-7 and C-8 may be bonded to a substituent other than hydrogen.

In certain embodiments, the tether group (also referred to as a "linker group") is selected from alkyl, substituted alkyl, alkenyl, substituted alkenyl, alkynyl, substituted alkynyl, alkylamino, alkylarylamino, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, the tether group is substituted with an R group, where R represents any one of the substituents described herein. For example, R may be selected from alkyl, substituted alkyl, alkylamino, alkylarylamino, aryl, substituted aryl, carbonyl, cycloalkyl, substituted cycloalkyl, heteroaryl, substituted heteroaryl, heterocyclyl, and substituted heterocyclyl.

The pharmaceutical compositions of the present disclosure include compounds of Formulae I-VII, shown below. Pharmaceutical compositions and methods of the present disclosure also include compounds of Formulae I-VII.

Formula I

The present disclosure provides a pharmaceutical composition that comprises a compound of formula (I):

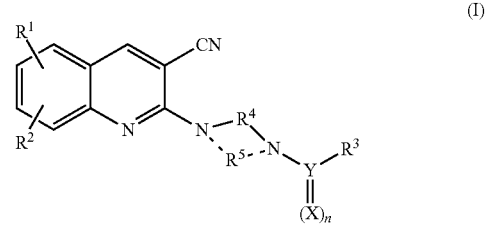

or salts, solvates, hydrates, and prodrug forms thereof, and stereoisomers thereof, wherein:

$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl;

$R^3$ is selected from alkyl, substituted alkyl, alkylamino, alkylarylamino, aryl, substituted aryl, cycloalkyl, substituted cycloalkyl, heteroaryl, substituted heteroaryl, heterocyclyl, and substituted heterocyclyl;

$R^4$ is an alkyl or substituted alkyl;

$R^5$ is optional and, if present, is an alkyl or substituted alkyl; and

Y is C or S, with the proviso that:
when Y is C, X is either O or S, and n is 1, and
when Y is S, X is O, and n is 2.

In the chemical formulae described herein, the dashed lines indicate optional bonds. In Formula (I), $R^1$ is selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, $R^1$ is selected from hydrogen, alkyl, substituted alkyl, alkenyl, substituted alkenyl, alkoxy, substituted alkoxy, aryl, substituted aryl, heteroaryl, substituted heteroaryl, heterocyclyl, and substituted heterocyclyl. In certain embodiments, $R^1$ is selected from hydrogen, alkyl, substituted alkyl, alkenyl, substituted alkenyl, alkoxy, substituted alkoxy, aryl, and substituted aryl. In certain embodiments, $R^1$ is selected from hydrogen, alkyl, substituted alkyl, alkoxy, and substituted alkoxy.

In certain embodiments, $R^1$ is hydrogen. In certain embodiments, $R^1$ is alkyl. In certain embodiments, $R^1$ is substituted alkyl. In certain embodiments, $R^1$ is alkenyl. In certain embodiments, $R^1$ is substituted alkenyl. In certain embodiments, $R^1$ is alkynyl. In certain embodiments, $R^1$ is substituted alkynyl. In certain embodiments, $R^1$ is alkoxy. In certain embodiments, $R^1$ is substituted alkoxy. In certain embodiments, $R^1$ is aryl. In certain embodiments, $R^1$ is substituted aryl. In certain embodiments, $R^1$ is cycloalkyl. In certain embodiments, $R^1$ is substituted cycloalkyl. In certain embodiments, $R^1$ is heteroaryl. In certain embodiments, $R^1$ is substituted heteroaryl. In certain embodiments, $R^1$ is heterocyclyl. In certain embodiments, $R^1$ is substituted heterocyclyl.

In Formula (I), $R^2$ is selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, $R^2$ is selected from hydrogen, alkyl, substituted alkyl, alkenyl, substituted alkenyl, alkoxy, substituted alkoxy, aryl, substituted aryl, heteroaryl, substituted heteroaryl, heterocyclyl, and substituted heterocyclyl. In certain embodiments, $R^2$ is selected from hydrogen, alkyl, substituted alkyl, alkenyl, substituted alkenyl, alkoxy, substituted alkoxy, aryl, and substituted aryl. In certain embodiments, $R^2$ is selected from hydrogen, alkyl, substituted alkyl, alkoxy, and substituted alkoxy.

In certain embodiments, $R^2$ is hydrogen. In certain embodiments, $R^2$ is alkyl. In certain embodiments, $R^2$ is substituted alkyl. In certain embodiments, $R^2$ is alkenyl. In certain embodiments, $R^2$ is substituted alkenyl. In certain embodiments, $R^2$ is alkynyl. In certain embodiments, $R^2$ is substituted alkynyl. In certain embodiments, $R^2$ is alkoxy. In certain embodiments, $R^2$ is substituted alkoxy. In certain embodiments, $R^2$ is aryl. In certain embodiments, $R^2$ is substituted aryl. In certain embodiments, $R^2$ is cycloalkyl. In certain embodiments, $R^2$ is substituted cycloalkyl. In certain embodiments, $R^2$ is heteroaryl. In certain embodiments, $R^2$ is substituted heteroaryl. In certain embodiments, $R^2$ is heterocyclyl. In certain embodiments, $R^2$ is substituted heterocyclyl.

In Formula (I), $R^3$ is selected from alkyl, substituted alkyl, alkylamino, alkylarylamino, aryl, substituted aryl, cycloalkyl, substituted cycloalkyl, heteroaryl, substituted heteroaryl, heterocyclyl, and substituted heterocyclyl.

In certain embodiments, $R^3$ is selected from alkylamino, alkylarylamino, aryl, substituted aryl, cycloalkyl, substituted cycloalkyl, heteroaryl, substituted heteroaryl, heterocyclyl, and substituted heterocyclyl. In certain embodiments, $R^3$ is selected from alkylamino, alkylarylamino, aryl, substituted aryl, heteroaryl, and substituted heteroaryl.

In certain embodiments, $R^3$ is alkyl. In certain embodiments, $R^3$ is substituted alkyl. In certain embodiments, $R^3$ is alkylamino. In certain embodiments, $R^3$ is alkylarylamino. In certain embodiments, $R^3$ is aryl. In certain embodiments, $R^3$ is substituted aryl. In certain embodiments, $R^3$ is cycloalkyl. In certain embodiments, $R^3$ is substituted cycloalkyl. In certain embodiments, $R^3$ is heteroaryl. In certain embodiments, $R^3$ is substituted heteroaryl. In certain embodiments, $R^3$ is heterocyclyl. In certain embodiments, $R^3$ is substituted heterocyclyl.

In Formula (I), $R^4$ is selected from alkyl and substituted alkyl. In certain embodiments, $R^4$ is alkyl. In certain embodiments, $R^4$ is substituted alkyl.

In Formula (I), $R^5$ is optional. If present, $R^5$ is selected from alkyl and substituted alkyl. In certain embodiments, $R^5$ is alkyl. In certain embodiments, $R^5$ is substituted alkyl. The dashed lines indicate optional bonds that are not present if $R^5$ is not present, and are present if $R^5$ is present. In certain embodiments, when $R^5$ is present, the optional bonds are also present, such that the portion of the molecule denoted by the following structure

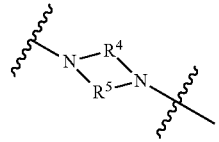

is a heterocyclyl or substituted heterocyclyl group. In the chemical formulae described herein, the wavy lines (∼∼∼) indicate attachment points to the remainder of the chemical structure.

In certain embodiments, as shown in Table I below, compounds of Formula I include Compound 01, Compound 02, Compound 03, Compound 05, Compound 08, Compound 09, Compound 10, Compound 14, Compound 20, Compound 22, Compound 35, Compound 68, Compound CP1, Compound CP3, Compound CP4, Compound CP5, Compound CP6, Compound AW1, Compound AW2, Compound AW3, Compound AW4, Compound AW5, Compound AW6, Compound AW7, Compound AW8, Compound AW9, Compound AW10, Compound AW11, Compound AW12, Compound 100, Compound 101, Compound 102, Compound 103, Compound 110, and Compound III. In some instances, compounds of Formula I do not include Compound AW5. In certain cases, compounds of Formula I do not include Compound AW6.

Formula II

The present disclosure provides a pharmaceutical composition that comprises a compound of formula (II):

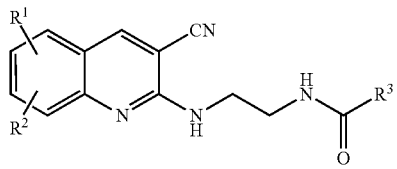
(II)

or salts, solvates, hydrates, and prodrug forms thereof, and stereoisomers thereof, wherein:

$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and $R^3$ is selected from aryl, substituted aryl, cycloalkyl, substituted cycloalkyl, heteroaryl, substituted heteroaryl, heterocyclyl, and substituted heterocyclyl.

In certain embodiments, as shown in Table II below, compounds of Formula II include Compound 01, Compound 02, Compound 03, Compound 22, Compound CP1, Compound CP3, Compound CP4, Compound CP5, Compound CP6, Compound 100, Compound 101, Compound 102, Compound 103, Compound 110, and Compound 111.

Formula III

The present disclosure provides a pharmaceutical composition that comprises a compound of formula (III):

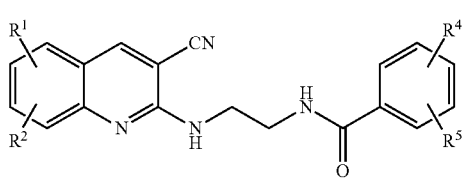
(III)

or salts, solvates, hydrates, and prodrug forms thereof, and stereoisomers thereof, wherein:

$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and $R^4$ and $R^5$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, as shown in Table III below, compounds of Formula III include Compound 01, Compound 02, Compound 22, Compound CP1, Compound CP3, Compound 100, Compound 101, Compound 102, and Compound 103.

Formula IV

The present disclosure provides a pharmaceutical composition that comprises a compound of formula (IV):

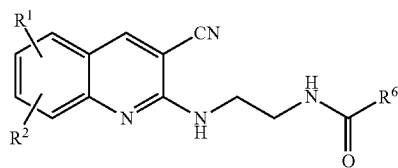
(IV)

or salts, solvates, hydrates, and prodrug forms thereof, and stereoisomers thereof, wherein:

$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and $R^6$ is selected from heteroaryl and substituted heteroaryl.

In Formulae (II), (III) and (IV), $R^1$ is selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, $R^1$ is selected from hydrogen, alkyl, substituted alkyl, alkenyl, substituted alkenyl, alkoxy, substituted alkoxy, aryl, substituted aryl, heteroaryl, substituted heteroaryl, heterocyclyl, and substituted heterocyclyl. In certain embodiments, $R^1$ is selected from hydrogen, alkyl, substituted alkyl, alkenyl, substituted alkenyl, alkoxy, substituted alkoxy, aryl, and substituted aryl. In certain embodiments, $R^1$ is selected from hydrogen, alkyl, substituted alkyl, alkoxy, and substituted alkoxy.

In certain embodiments, $R^1$ is hydrogen. In certain embodiments, $R^1$ is alkyl. In certain embodiments, $R^1$ is substituted alkyl. In certain embodiments, $R^1$ is alkenyl. In certain embodiments, $R^1$ is substituted alkenyl. In certain embodiments, $R^1$ is alkynyl. In certain embodiments, $R^1$ is substituted alkynyl. In certain embodiments, $R^1$ is alkoxy. In certain embodiments, $R^1$ is substituted alkoxy. In certain embodiments, $R^1$ is aryl. In certain embodiments, $R^1$ is substituted aryl. In certain embodiments, $R^1$ is cycloalkyl. In certain embodiments, $R^1$ is substituted cycloalkyl. In certain embodiments, $R^1$ is heteroaryl. In certain embodiments, $R^1$ is substituted heteroaryl. In certain embodiments, $R^1$ is heterocyclyl. In certain embodiments, $R^1$ is substituted heterocyclyl.

In Formulae (II), (III) and (IV), $R^2$ is selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, $R^2$ is selected from hydrogen, alkyl, substituted alkyl, alkenyl, substituted alkenyl, alkoxy, substituted alkoxy, aryl, substituted aryl, heteroaryl, substituted heteroaryl, heterocyclyl, and substituted heterocyclyl. In certain embodiments, $R^2$ is selected from hydrogen, alkyl, substituted alkyl, alkenyl, substituted alkenyl, alkoxy, substituted alkoxy, aryl, and substituted aryl. In certain embodiments, $R^2$ is selected from hydrogen, alkyl, substituted alkyl, alkoxy, and substituted alkoxy.

In certain embodiments, $R^2$ is hydrogen. In certain embodiments, $R^2$ is alkyl. In certain embodiments, $R^2$ is substituted alkyl. In certain embodiments, $R^2$ is alkenyl. In certain embodiments, $R^2$ is substituted alkenyl. In certain embodiments, $R^2$ is alkynyl. In certain embodiments, $R^2$ is substituted alkynyl. In certain embodiments, $R^2$ is alkoxy. In certain embodiments, $R^2$ is substituted alkoxy. In certain embodiments, $R^2$ is aryl. In certain embodiments, $R^2$ is substituted aryl. In certain embodiments, $R^2$ is cycloalkyl. In certain embodiments, $R^2$ is substituted cycloalkyl. In certain embodiments, $R^2$ is heteroaryl. In certain embodiments, $R^2$ is substituted heteroaryl. In certain embodiments, $R^2$ is heterocyclyl. In certain embodiments, $R^2$ is substituted heterocyclyl.

In Formulae (II), (III) and (IV), $R^3$ is selected from aryl, substituted aryl, cycloalkyl, substituted cycloalkyl, heteroaryl, substituted heteroaryl, heterocyclyl, and substituted heterocyclyl.

In certain embodiments, $R^3$ is selected from aryl, substituted aryl, cycloalkyl, substituted cycloalkyl, heteroaryl, substituted heteroaryl, heterocyclyl, and substituted heterocyclyl. In certain embodiments, $R^3$ is selected from aryl, substituted aryl, heteroaryl, and substituted heteroaryl.

In certain embodiments, $R^3$ is aryl. In certain embodiments, $R^3$ is substituted aryl. In certain embodiments, $R^3$ is cycloalkyl. In certain embodiments, $R^3$ is substituted cycloalkyl. In certain embodiments, $R^3$ is heteroaryl. In certain embodiments, $R^3$ is substituted heteroaryl. In certain embodiments, $R^3$ is heterocyclyl. In certain embodiments, $R^3$ is substituted heterocyclyl.

In Formulae (II), (III) and (IV), $R^4$ is selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, $R^4$ is selected from hydrogen, alkyl, substituted alkyl, alkenyl, substituted alkenyl, alkoxy, substituted alkoxy, aryl, substituted aryl, heteroaryl, substituted heteroaryl, heterocyclyl, and substituted heterocyclyl. In certain embodiments, $R^4$ is selected from hydrogen, alkyl, substituted alkyl, alkenyl, substituted alkenyl, alkoxy, substituted alkoxy, aryl, and substituted aryl. In certain embodiments, $R^4$ is selected from hydrogen, alkyl, substituted alkyl, alkoxy, and substituted alkoxy.

In certain embodiments, $R^4$ is hydrogen. In certain embodiments, $R^4$ is alkyl. In certain embodiments, $R^4$ is substituted alkyl. In certain embodiments, $R^4$ is alkenyl. In certain embodiments, $R^4$ is substituted alkenyl. In certain embodiments, $R^4$ is alkynyl. In certain embodiments, $R^4$ is substituted alkynyl. In certain embodiments, $R^4$ is alkoxy. In certain embodiments, $R^4$ is substituted alkoxy. In certain embodiments, $R^4$ is aryl. In certain embodiments, $R^4$ is substituted aryl. In certain embodiments, $R^4$ is cycloalkyl. In certain embodiments, $R^4$ is substituted cycloalkyl. In certain embodiments, $R^4$ is heteroaryl. In certain embodiments, $R^4$ is substituted heteroaryl. In certain embodiments, $R^4$ is heterocyclyl. In certain embodiments, $R^4$ is substituted heterocyclyl.

In Formulae (II), (III) and (IV), $R^5$ is selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, $R^5$ is selected from hydrogen, alkyl, substituted alkyl, alkenyl, substituted alkenyl, alkoxy, substituted alkoxy, aryl, substituted aryl, heteroaryl, substituted heteroaryl, heterocyclyl, and substituted heterocyclyl. In certain embodiments, $R^5$ is selected from hydrogen, alkyl, substituted alkyl, alkenyl, substituted alkenyl, alkoxy, substituted alkoxy, aryl, and substituted aryl. In certain embodiments, $R^5$ is selected from hydrogen, alkyl, substituted alkyl, alkoxy, and substituted alkoxy.

In certain embodiments, $R^5$ is hydrogen. In certain embodiments, $R^5$ is alkyl. In certain embodiments, $R^5$ is substituted alkyl. In certain embodiments, $R^5$ is alkenyl. In certain embodiments, $R^5$ is substituted alkenyl. In certain embodiments, $R^5$ is alkynyl. In certain embodiments, $R^5$ is substituted alkynyl. In certain embodiments, $R^5$ is alkoxy. In certain embodiments, $R^5$ is substituted alkoxy. In certain embodiments, $R^5$ is aryl. In certain embodiments, $R^5$ is substituted aryl. In certain embodiments, $R^5$ is cycloalkyl. In certain embodiments, $R^5$ is substituted cycloalkyl. In certain embodiments, $R^5$ is heteroaryl. In certain embodiments, $R^5$ is substituted heteroaryl. In certain embodiments, $R^5$ is heterocyclyl. In certain embodiments, $R^5$ is substituted heterocyclyl.

In Formulae (II), (III) and (IV), $R^6$ is selected from heteroaryl and substituted heteroaryl.

In certain embodiments, $R^6$ is heteroaryl. In certain embodiments, $R^6$ is substituted heteroaryl.

In certain embodiments, as shown in Table IV below, compounds of Formula IV include Compound 03, Compound CP4, Compound CP5, Compound CP6, Compound 110, and Compound 111.

Formula V

The present disclosure provides a pharmaceutical composition that comprises a compound of formula (V):

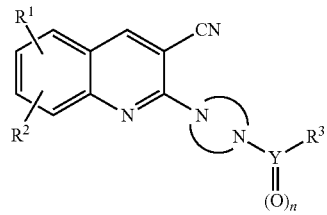

(V)

or salts, solvates, hydrates, and prodrug forms thereof, and stereoisomers thereof, wherein:

$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl;

$R^3$ is selected from alkyl, substituted alkyl, aryl, substituted aryl, cycloalkyl, substituted cycloalkyl, heteroaryl, substituted heteroaryl, heterocyclyl, and substituted heterocyclyl;

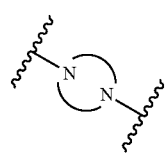

is a heterocylyl or substituted heterocyclyl; and

Y is C or S, with the proviso that when Y is C, n is 1 and when Y is S, n is 2.

In the chemical formulae described herein, the wavy lines (⁓) indicate attachment points to the remainder of the chemical structure.

In Formula (V), $R^1$ is selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, $R^1$ is selected from hydrogen, alkyl, substituted alkyl, alkenyl, substituted alkenyl, alkoxy, substituted alkoxy, aryl, substituted aryl, heteroaryl, substituted heteroaryl, heterocyclyl, and substituted heterocyclyl. In certain embodiments, $R^1$ is selected from hydrogen, alkyl, substituted alkyl, alkenyl, substituted alkenyl, alkoxy, substituted alkoxy, aryl, and substituted aryl. In certain embodiments, $R^1$ is selected from hydrogen, alkyl, substituted alkyl, alkoxy, and substituted alkoxy.

In certain embodiments, $R^1$ is hydrogen. In certain embodiments, $R^1$ is alkyl. In certain embodiments, $R^1$ is substituted alkyl. In certain embodiments, $R^1$ is alkenyl. In certain embodiments, $R^1$ is substituted alkenyl. In certain embodiments, $R^1$ is alkynyl. In certain embodiments, $R^1$ is substituted alkynyl. In certain embodiments, $R^1$ is alkoxy. In certain embodiments, $R^1$ is substituted alkoxy. In certain embodiments, $R^1$ is aryl. In certain embodiments, $R^1$ is substituted aryl. In certain embodiments, $R^1$ is cycloalkyl. In certain embodiments, $R^1$ is substituted cycloalkyl. In certain embodiments, $R^1$ is heteroaryl. In certain embodiments, $R^1$ is substituted heteroaryl. In certain embodiments, $R^1$ is heterocyclyl. In certain embodiments, $R^1$ is substituted heterocyclyl.

In Formula (V), $R^2$ is selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, $R^2$ is selected from hydrogen, alkyl, substituted alkyl, alkenyl, substituted alkenyl, alkoxy, substituted alkoxy, aryl, substituted aryl, heteroaryl, substituted heteroaryl, heterocyclyl, and substituted heterocyclyl. In certain embodiments, $R^2$ is selected from hydrogen, alkyl, substituted alkyl, alkenyl, substituted alkenyl, alkoxy, substituted alkoxy, aryl, and substituted aryl. In certain embodiments, $R^2$ is selected from hydrogen, alkyl, substituted alkyl, alkoxy, and substituted alkoxy.

In certain embodiments, $R^2$ is hydrogen. In certain embodiments, $R^2$ is alkyl. In certain embodiments, $R^2$ is substituted alkyl. In certain embodiments, $R^2$ is alkenyl. In certain embodiments, $R^2$ is substituted alkenyl. In certain embodiments, $R^2$ is alkynyl. In certain embodiments, $R^2$ is substituted alkynyl. In certain embodiments, $R^2$ is alkoxy. In certain embodiments, $R^2$ is substituted alkoxy. In certain embodiments, $R^2$ is aryl. In certain embodiments, $R^2$ is substituted aryl. In certain embodiments, $R^2$ is cycloalkyl. In certain embodiments, $R^2$ is substituted cycloalkyl. In certain embodiments, $R^2$ is heteroaryl. In certain embodiments, $R^2$ is substituted heteroaryl. In certain embodiments, $R^2$ is heterocyclyl. In certain embodiments, $R^2$ is substituted heterocyclyl.

In Formula (V), $R^3$ is selected from alkyl, substituted alkyl, aryl, substituted aryl, cycloalkyl, substituted cycloalkyl, heteroaryl, substituted heteroaryl, heterocyclyl, and substituted heterocyclyl.

In certain embodiments, $R^3$ is selected from alkyl, substituted alkyl, aryl, substituted aryl, cycloalkyl, substituted cycloalkyl, heteroaryl, substituted heteroaryl, heterocyclyl, and substituted heterocyclyl. In certain embodiments, $R^3$ is selected from alkyl, substituted alkyl, aryl, substituted aryl, heteroaryl, and substituted heteroaryl. In certain embodiments, $R^3$ is selected from aryl, substituted aryl, heteroaryl, and substituted heteroaryl.

In certain embodiments, $R^3$ is alkyl. In certain embodiments, $R^3$ is substituted alkyl. In certain embodiments, $R^3$ is aryl. In certain embodiments, $R^3$ is substituted aryl. In certain embodiments, $R^3$ is cycloalkyl. In certain embodiments, $R^3$ is substituted cycloalkyl. In certain embodiments, $R^3$ is heteroaryl. In certain embodiments, $R^3$ is substituted heteroaryl. In certain embodiments, $R^3$ is heterocyclyl. In certain embodiments, $R^3$ is substituted heterocyclyl.

In certain embodiments, as shown in Table V below, compounds of Formula V include Compound 05, Compound 08, Compound 09, Compound 10, Compound 20, Compound 35, Compound AW1, Compound AW2, Compound AW3, Compound AW4, Compound AW5, and Compound AW6. In some instances, compounds of Formula V do not include Compound AW6. In certain cases, compounds of Formula V do not include Compound AW6.

Formula VI

The present disclosure provides a pharmaceutical composition that comprises a compound of formula (VI):

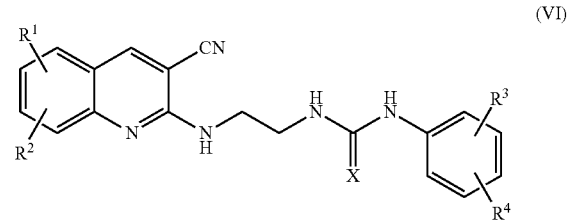

or salts, solvates, hydrates, and prodrug forms thereof, and stereoisomers thereof, wherein:

$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and $R^3$ and $R^4$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and X is O or S.

In Formula (VI), $R^1$ is selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, $R^1$ is selected from hydrogen, alkyl, substituted alkyl, alkenyl, substituted alkenyl, alkoxy, substituted alkoxy, aryl, substituted aryl, heteroaryl, substituted heteroaryl, heterocyclyl, and substituted heterocyclyl. In certain embodiments, $R^1$ is selected from hydrogen, alkyl, substituted alkyl, alkenyl, substituted alkenyl, alkoxy, substituted alkoxy, aryl, and substituted aryl. In certain embodiments, $R^1$ is selected from hydrogen, alkyl, substituted alkyl, alkoxy, and substituted alkoxy.

In certain embodiments, $R^1$ is hydrogen. In certain embodiments, $R^1$ is alkyl. In certain embodiments, $R^1$ is substituted alkyl. In certain embodiments, $R^1$ is alkenyl. In certain embodiments, $R^1$ is substituted alkenyl. In certain embodiments, $R^1$ is alkynyl. In certain embodiments, $R^1$ is substituted alkynyl. In certain embodiments, $R^1$ is alkoxy. In certain embodiments, $R^1$ is substituted alkoxy. In certain embodiments, $R^1$ is aryl. In certain embodiments, $R^1$ is substituted aryl. In certain embodiments, $R^1$ is cycloalkyl. In certain embodiments, $R^1$ is substituted cycloalkyl. In certain embodiments, $R^1$ is heteroaryl. In certain embodiments, $R^1$ is substituted heteroaryl. In certain embodiments, R¹ is heterocyclyl. In certain embodiments, R¹ is substituted heterocyclyl.

In Formula (VI), R² is selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, R² is selected from hydrogen, alkyl, substituted alkyl, alkenyl, substituted alkenyl, alkoxy, substituted alkoxy, aryl, substituted aryl, heteroaryl, substituted heteroaryl, heterocyclyl, and substituted heterocyclyl. In certain embodiments, R² is selected from hydrogen, alkyl, substituted alkyl, alkenyl, substituted alkenyl, alkoxy, substituted alkoxy, aryl, and substituted aryl. In certain embodiments, R² is selected from hydrogen, alkyl, substituted alkyl, alkoxy, and substituted alkoxy.

In certain embodiments, R² is hydrogen. In certain embodiments, R² is alkyl. In certain embodiments, R² is substituted alkyl. In certain embodiments, R² is alkenyl. In certain embodiments, R² is substituted alkenyl. In certain embodiments, R² is alkynyl. In certain embodiments, R² is substituted alkynyl. In certain embodiments, R² is alkoxy. In certain embodiments, R² is substituted alkoxy. In certain embodiments, R² is aryl. In certain embodiments, R² is substituted aryl. In certain embodiments, R² is cycloalkyl. In certain embodiments, R² is substituted cycloalkyl. In certain embodiments, R² is heteroaryl. In certain embodiments, R² is substituted heteroaryl. In certain embodiments, R² is heterocyclyl. In certain embodiments, R² is substituted heterocyclyl.

In Formula (VI), R³ is selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, R³ is selected from hydrogen, alkyl, substituted alkyl, alkenyl, substituted alkenyl, alkoxy, substituted alkoxy, aryl, substituted aryl, heteroaryl, substituted heteroaryl, heterocyclyl, and substituted heterocyclyl. In certain embodiments, R³ is selected from hydrogen, alkyl, substituted alkyl, alkenyl, substituted alkenyl, alkoxy, substituted alkoxy, aryl, and substituted aryl. In certain embodiments, R³ is selected from hydrogen, alkyl, substituted alkyl, alkoxy, and substituted alkoxy.

In certain embodiments, R³ is hydrogen. In certain embodiments, R³ is alkyl. In certain embodiments, R³ is substituted alkyl. In certain embodiments, R³ is alkenyl. In certain embodiments, R³ is substituted alkenyl. In certain embodiments, R³ is alkynyl. In certain embodiments, R³ is substituted alkynyl. In certain embodiments, R³ is alkoxy. In certain embodiments, R³ is substituted alkoxy. In certain embodiments, R³ is aryl. In certain embodiments, R³ is substituted aryl. In certain embodiments, R³ is cycloalkyl. In certain embodiments, R³ is substituted cycloalkyl. In certain embodiments, R³ is heteroaryl. In certain embodiments, R³ is substituted heteroaryl. In certain embodiments, R³ is heterocyclyl. In certain embodiments, R³ is substituted heterocyclyl.

In Formula (VI), R⁴ is selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, R⁴ is selected from hydrogen, alkyl, substituted alkyl, alkenyl, substituted alkenyl, alkoxy, substituted alkoxy, aryl, substituted aryl, heteroaryl, substituted heteroaryl, heterocyclyl, and substituted heterocyclyl. In certain embodiments, R⁴ is selected from hydrogen, alkyl, substituted alkyl, alkenyl, substituted alkenyl, alkoxy, substituted alkoxy, aryl, and substituted aryl. In certain embodiments, R⁴ is selected from hydrogen, alkyl, substituted alkyl, alkoxy, and substituted alkoxy.

In certain embodiments, R⁴ is hydrogen. In certain embodiments, R⁴ is alkyl. In certain embodiments, R⁴ is substituted alkyl. In certain embodiments, R⁴ is alkenyl. In certain embodiments, R⁴ is substituted alkenyl. In certain embodiments, R⁴ is alkynyl. In certain embodiments, R⁴ is substituted alkynyl. In certain embodiments, R⁴ is alkoxy. In certain embodiments, R⁴ is substituted alkoxy. In certain embodiments, R⁴ is aryl. In certain embodiments, R⁴ is substituted aryl. In certain embodiments, R⁴ is cycloalkyl. In certain embodiments, R⁴ is substituted cycloalkyl. In certain embodiments, R⁴ is heteroaryl. In certain embodiments, R⁴ is substituted heteroaryl. In certain embodiments, R⁴ is heterocyclyl. In certain embodiments, R⁴ is substituted heterocyclyl.

In certain embodiments, as shown in Table VI below, compounds of Formula VI include Compound 14 and Compound 68.

Formula VII

The present disclosure provides a pharmaceutical composition that comprises a compound of formula (VII):

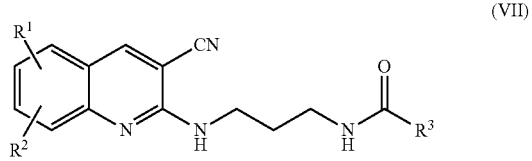

or salts, solvates, hydrates, and prodrug forms thereof, and stereoisomers thereof, wherein:

R¹ and R² are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and R³ is selected from aryl, substituted aryl, cycloalkyl, substituted cycloalkyl, heteroaryl, substituted heteroaryl, heterocyclyl, and substituted heterocyclyl.

In Formula (VII), R¹ is selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, R¹ is selected from hydrogen, alkyl, substituted alkyl, alkenyl, substituted alkenyl, alkoxy, substituted alkoxy, aryl, substituted aryl, heteroaryl, substituted heteroaryl, heterocyclyl, and substituted heterocyclyl. In certain embodiments, R¹ is selected from hydrogen, alkyl, substituted alkyl, alkenyl, substituted alkenyl, alkoxy, substituted alkoxy, aryl, and substituted aryl. In certain embodiments, R¹ is selected from hydrogen, alkyl, substituted alkyl, alkoxy, and substituted alkoxy.

In certain embodiments, R¹ is hydrogen. In certain embodiments, R¹ is alkyl. In certain embodiments, R¹ is substituted alkyl. In certain embodiments, R¹ is alkenyl. In certain embodiments, R¹ is substituted alkenyl. In certain embodiments, R¹ is alkynyl. In certain embodiments, R¹ is substituted alkynyl. In certain embodiments, R¹ is alkoxy. In certain embodiments, R¹ is substituted alkoxy. In certain embodiments, R¹ is aryl. In certain embodiments, R¹ is substituted aryl. In certain embodiments, R¹ is cycloalkyl. In certain embodiments, R¹ is substituted cycloalkyl. In certain embodiments, $R^1$ is heteroaryl. In certain embodiments, $R^1$ is substituted heteroaryl. In certain embodiments, $R^1$ is heterocyclyl. In certain embodiments, $R^1$ is substituted heterocyclyl.

In Formula (VII), $R^2$ is selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

In certain embodiments, $R^2$ is selected from hydrogen, alkyl, substituted alkyl, alkenyl, substituted alkenyl, alkoxy, substituted alkoxy, aryl, substituted aryl, heteroaryl, substituted heteroaryl, heterocyclyl, and substituted heterocyclyl. In certain embodiments, $R^2$ is selected from hydrogen, alkyl, substituted alkyl, alkenyl, substituted alkenyl, alkoxy, substituted alkoxy, aryl, and substituted aryl. In certain embodiments, $R^2$ is selected from hydrogen, alkyl, substituted alkyl, alkoxy, and substituted alkoxy.

In certain embodiments, $R^2$ is hydrogen. In certain embodiments, $R^2$ is alkyl. In certain embodiments, $R^2$ is substituted alkyl. In certain embodiments, $R^2$ is alkenyl. In certain embodiments, $R^2$ is substituted alkenyl. In certain embodiments, $R^2$ is alkynyl. In certain embodiments, $R^2$ is substituted alkynyl. In certain embodiments, $R^2$ is alkoxy. In certain embodiments, $R^2$ is substituted alkoxy. In certain embodiments, $R^2$ is aryl. In certain embodiments, $R^2$ is substituted aryl. In certain embodiments, $R^2$ is cycloalkyl. In certain embodiments, $R^2$ is substituted cycloalkyl. In certain embodiments, $R^2$ is heteroaryl. In certain embodiments, $R^2$ is substituted heteroaryl. In certain embodiments, $R^2$ is heterocyclyl. In certain embodiments, $R^2$ is substituted heterocyclyl.

In Formula (VII), $R^3$ is selected from aryl, substituted aryl, cycloalkyl, substituted cycloalkyl, heteroaryl, substituted heteroaryl, heterocyclyl, and substituted heterocyclyl.

In certain embodiments, $R^3$ is selected from aryl, substituted aryl, cycloalkyl, substituted cycloalkyl, heteroaryl, substituted heteroaryl, heterocyclyl, and substituted heterocyclyl. In certain embodiments, $R^3$ is selected from aryl, substituted aryl, heteroaryl, and substituted heteroaryl.

In certain embodiments, $R^3$ is aryl. In certain embodiments, $R^3$ is substituted aryl. In certain embodiments, $R^3$ is cycloalkyl. In certain embodiments, $R^3$ is substituted cycloalkyl. In certain embodiments, $R^3$ is heteroaryl. In certain embodiments, $R^3$ is substituted heteroaryl. In certain embodiments, $R^3$ is heterocyclyl. In certain embodiments, $R^3$ is substituted heterocyclyl.

In certain embodiments, as shown in Table VII below, compounds of Formula VII include Compound AW7, Compound AW8, Compound AW9, Compound AW10, Compound AW11, and Compound AW12.

Embodiments of Formulae I-VII include compounds illustrated in the following tables. The positions of the $R^1$ and $R^2$ substituents on the cyanoquinoline ring are indicated where relevant. Atom numbering of the cyanoquinoline ring is shown for example in the figure below.

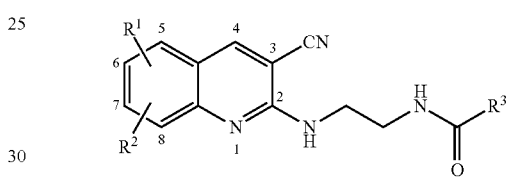

TABLE I

Compounds of Formula I

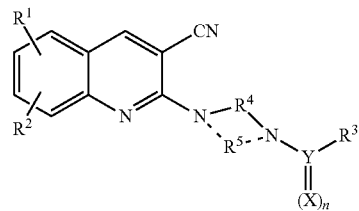

(I)

| Compound | $R^1$ (position) | $R^2$ (position) | 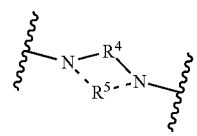 | X | Y | $R^3$ |
|---|---|---|---|---|---|---|
| 01 | $CH_3$ (C-8) | H | —NHCH$_2$CH$_2$NH— | O | C | |
| 02 | $CH_3$ (C-6) | H | —NHCH$_2$CH$_2$NH— | O | C | |

TABLE I-continued

Compounds of Formula I

| Compound | R¹ (position) | R² (position) | linker | X | Y | R³ |
|---|---|---|---|---|---|---|
| 03 | $CH_3$ (C-5) | $CH_3$ (C-7) | —$NHCH_2CH_2NH$— | O | C | 2-thienyl |
| 05 | $CH_3$ (C-6) | H | piperazine | O | S | 4-methoxyphenyl |
| 08 | $OCH_3$ (C-6) | H | piperazine | O | C | 2-fluorophenyl |
| 09 | $OCH_3$ (C-6) | H | piperazine | O | C | 2-chlorophenyl |
| 10 | $OCH_3$ (C-6) | H | piperazine | O | C | 2-bromophenyl |
| 14 | $CH_3$ (C-8) | H | —$NHCH_2CH_2NH$— | S | C | 2-ethoxyphenylamino |
| 20 | $CH_3$ (C-7) | H | homopiperazine | O | C | 2-thienyl |

TABLE I-continued

Compounds of Formula I

| Compound | R¹ (position) | R² (position) | (linker) | X | Y | R³ |
|---|---|---|---|---|---|---|
| 22 | CH₃ (C-5) | CH₃ (C-7) | —NHCH₂CH₂NH— | O | C | 3-methoxyphenyl |
| 35 | CH₃ (C-6) | CH₃ (C-7) | piperazinyl | O | S | CH₃ |
| 68 | OCH₃ (C-6) | H | —NHCH₂CH₂NH— | O | C | NH-(3-methylphenyl) |
| CP1 | CH₃ (C-5) | CH₃ (C-7) | —NHCH₂CH₂NH— | O | C | 2-methoxyphenyl |
| CP3 | CH₃ (C-5) | CH₃ (C-7) | —NHCH₂CH₂NH— | O | C | 4-methoxyphenyl |
| CP4 | CH₃ (C-5) | CH₃ (C-7) | —NHCH₂CH₂NH— | O | C | pyridin-2-yl |
| CP5 | CH₃ (C-5) | CH₃ (C-7) | —NHCH₂CH₂NH— | O | C | pyridin-3-yl |

TABLE I-continued
Compounds of Formula I
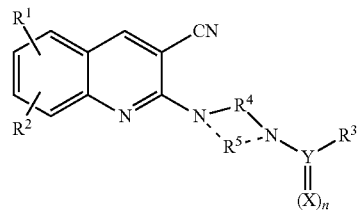
(I)
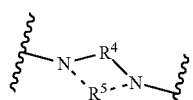
| Compound | R¹ (position) | R² (position) | | X | Y | R³ |
|---|---|---|---|---|---|---|
| CP6 | CH₃ (C-5) | CH₃ (C-7) | —NHCH₂CH₂NH— | O | C | 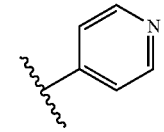 [SMILES: *c1ccncc1] |
| AW1 | CH₃ (C-5) | CH₃ (C-7) | 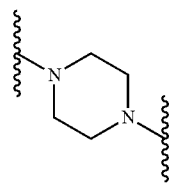 [SMILES: *N1CCN(*)CC1] | O | C | 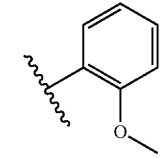 [SMILES: *c1ccccc1OC] |
| AW2 | CH₃ (C-5) | CH₃ (C-7) | 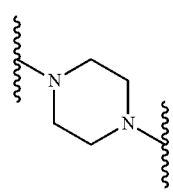 [SMILES: *N1CCN(*)CC1] | O | C | 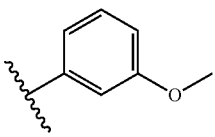 [SMILES: *c1cccc(OC)c1] |
| AW3 | CH₃ (C-5) | CH₃ (C-7) | 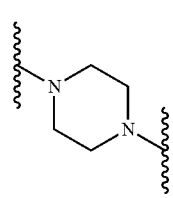 [SMILES: *N1CCN(*)CC1] | O | C | 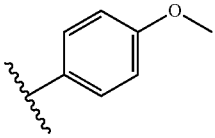 [SMILES: *c1ccc(OC)cc1] |
| AW4 | CH₃ (C-5) | CH₃ (C-7) | 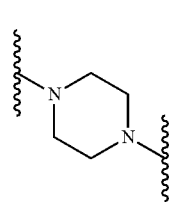 [SMILES: *N1CCN(*)CC1] | O | C | 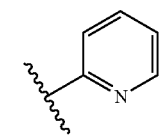 [SMILES: *c1ccccn1] |
| AW5 | CH₃ (C-5) | CH₃ (C-7) | 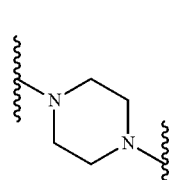 | O | C | 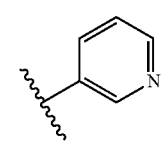 [SMILES: *c1cccnc1] |

US 9,073,863 B2
43                                                                                   44
TABLE I-continued
Compounds of Formula I
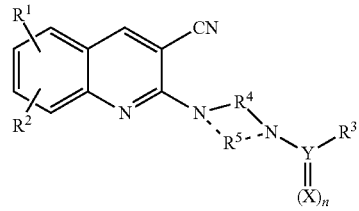
(I)
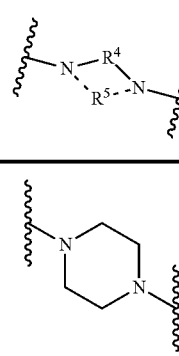
| Compound | R¹ (position) | R² (position) | | X | Y | R³ |
|---|---|---|---|---|---|---|
| AW6 | CH₃ (C-5) | CH₃ (C-7) | 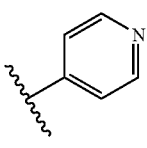 [SMILES: *c1ccncc1] | O | C | 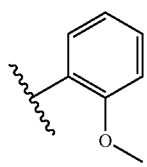 [SMILES: *c1ccccc1OC] |
| AW7 | CH₃ (C-5) | CH₃ (C-7) | —NHCH₂CH₂CH₂NH— | O | C | 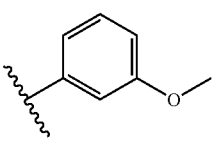 [SMILES: *c1cccc(OC)c1] |
| AW8 | CH₃ (C-5) | CH₃ (C-7) | —NHCH₂CH₂CH₂NH— | O | C | 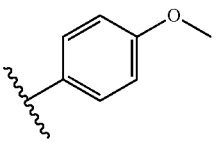 [SMILES: *c1ccc(OC)cc1] |
| AW9 | CH₃ (C-5) | CH₃ (C-7) | —NHCH₂CH₂CH₂NH— | O | C | 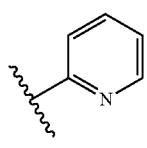 [SMILES: *c1ccccn1] |
| AW10 | CH₃ (C-5) | CH₃ (C-7) | —NHCH₂CH₂CH₂NH— | O | C | 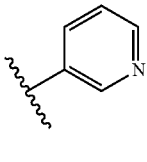 [SMILES: *c1cccnc1] |
| AW11 | CH₃ (C-5) | CH₃ (C-7) | —NHCH₂CH₂CH₂NH— | O | C | 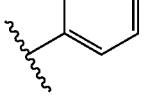 |
| AW12 | CH₃ (C-5) | CH₃ (C-7) | —NHCH₂CH₂CH₂NH— | O | C | |

TABLE I-continued

Compounds of Formula I (I)

| Compound | R¹ (position) | R² (position) | N-R⁴-R⁵-N bridge | X | Y | R³ |
|---|---|---|---|---|---|---|
| 100 | $CH_3$ (C-5) | $CH_3$ (C-7) | —NHCH₂CH₂NH— | O | C | phenyl |
| 101 | $CH_3$ (C-5) | $CH_3$ (C-7) | —NHCH₂CH₂NH— | O | C | 2,6-dimethoxyphenyl |
| 102 | $CH_3$ (C-5) | $CH_3$ (C-7) | —NHCH₂CH₂NH— | O | C | 2,4-dimethoxyphenyl |
| 103 | $CH_3$ (C-5) | $CH_3$ (C-7) | —NHCH₂CH₂NH— | O | C | 3,4-dimethoxyphenyl |
| 110 | $CH_3$ (C-5) | $CH_3$ (C-7) | —NHCH₂CH₂NH— | O | C | 5-methoxypyridin-2-yl |
| 111 | $CH_3$ (C-5) | $CH_3$ (C-7) | —NHCH₂CH₂NH— | O | C | pyrazin-2-yl |

TABLE II

Compounds of Formula II (II)

R¹ — quinoline with CN at 3-position, 2-NH-CH₂CH₂-NH-C(=O)-R³, R² on ring

| Compound | R¹ (position) | R² (position) | R³ |
|---|---|---|---|
| 01 | CH₃ (C-8) | H | 3,4-dimethoxyphenyl |
| 02 | CH₃ (C-6) | H | 3,4-dimethoxyphenyl |
| 03 | CH₃ (C-5) | CH₃ (C-7) | thiophen-2-yl |
| 22 | CH₃ (C-5) | CH₃ (C-7) | 3-methoxyphenyl |
| CP1 | CH₃ (C-5) | CH₃ (C-7) | 2-methoxyphenyl |
| CP3 | CH₃ (C-5) | CH₃ (C-7) | 4-methoxyphenyl |
| CP4 | CH₃ (C-5) | CH₃ (C-7) | pyridin-2-yl |
| CP5 | CH₃ (C-5) | CH₃ (C-7) | pyridin-3-yl |
| CP6 | CH₃ (C-5) | CH₃ (C-7) | pyridin-4-yl |
| 100 | CH₃ (C-5) | CH₃ (C-7) | phenyl |
| 101 | CH₃ (C-5) | CH₃ (C-7) | 2,6-dimethoxyphenyl |
| 102 | CH₃ (C-5) | CH₃ (C-7) | 2,4-dimethoxyphenyl |
| 103 | CH₃ (C-5) | CH₃ (C-7) | 3,4-dimethoxyphenyl |

TABLE II-continued

Compounds of Formula II

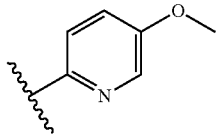 [SMILES: *c1ccc(OC)cn1]

| Compound | R¹ (position) | R² (position) | R³ |
|---|---|---|---|
| 110 | CH₃ (C-5) | CH₃ (C-7) | 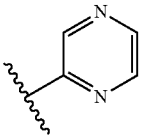 [SMILES: *c1cnccn1] |
| 111 | CH₃ (C-5) | CH₃ (C-7) | 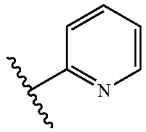 |

TABLE III

Compounds of Formula III

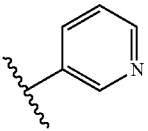 [SMILES: *c1cccnc1]

| Compound | R¹ (position) | R² (position) | R⁴ (position) | R⁵ (position) |
|---|---|---|---|---|
| 01 | CH₃ (C-8) | H | OCH₃ (C-3) | OCH₃ (C-3) |
| 02 | CH₃ (C-6) | H | OCH₃ (C-3) | OCH₃ (C-4) |
| 22 | CH₃ (C-5) | CH₃ (C-7) | OCH₃ (C-3) | H |
| CP1 | CH₃ (C-5) | CH₃ (C-7) | OCH₃ (C-2) | H |
| CP3 | CH₃ (C-5) | CH₃ (C-7) | OCH₃ (C-4) | H |
| 100 | CH₃ (C-5) | CH₃ (C-7) | H | H |
| 101 | CH₃ (C-5) | CH₃ (C-7) | OCH₃ (C-2) | OCH₃ (C-6) |
| 102 | CH₃ (C-5) | CH₃ (C-7) | OCH₃ (C-2) | OCH₃ (C-4) |
| 103 | CH₃ (C-5) | CH₃ (C-7) | OCH₃ (C-3) | OCH₃ (C-4) |

TABLE IV

Compounds of Formula IV

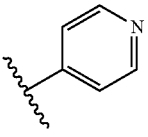 [SMILES: *c1ccncc1]

| Compound | R¹ (position) | R² (position) | R⁶ |
|---|---|---|---|
| 03 | CH₃ (C-5) | CH₃ (C-7) | 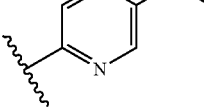 |

TABLE IV-continued

Compounds of Formula IV

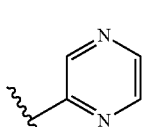

| Compound | R¹ (position) | R² (position) | R⁶ |
|---|---|---|---|
| CP4 | CH₃ (C-5) | CH₃ (C-7) | 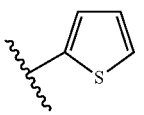 |
| CP5 | CH₃ (C-5) | CH₃ (C-7) | |
| CP6 | CH₃ (C-5) | CH₃ (C-7) | |
| 110 | CH₃ (C-5) | CH₃ (C-7) | |
| 111 | CH₃ (C-5) | CH₃ (C-7) | |

TABLE V

Compounds of Formula V

| Compound | R¹ (position) | R² (position) | Ring | Y | R³ |
|---|---|---|---|---|---|
| 05 | $CH_3$ (C-6) | H | piperazine | S | 4-methoxyphenyl |
| 08 | $OCH_3$ (C-6) | H | piperazine | C | 2-fluorophenyl |
| 09 | $OCH_3$ (C-6) | H | piperazine | C | 2-chlorophenyl |
| 10 | $OCH_3$ (C-6) | H | piperazine | C | 2-bromophenyl |
| 20 | $CH_3$ (C-7) | H | homopiperazine | C | 2-thienyl |
| 35 | $CH_3$ (C-6) | $CH_3$ (C-7) | piperazine | S | $CH_3$ |

TABLE V-continued

Compounds of Formula V (V)

| Compound | R¹ (position) | R² (position) | | Y | R³ |
|---|---|---|---|---|---|
| AW1 | $CH_3$ (C-5) | $CH_3$ (C-7) | piperazine | C | 2-methoxyphenyl |
| AW2 | $CH_3$ (C-5) | $CH_3$ (C-7) | piperazine | C | 3-methoxyphenyl |
| AW3 | $CH_3$ (C-5) | $CH_3$ (C-7) | piperazine | C | 4-methoxyphenyl |
| AW4 | $CH_3$ (C-5) | $CH_3$ (C-7) | piperazine | C | 2-pyridyl |
| AW5 | $CH_3$ (C-5) | $CH_3$ (C-7) | piperazine | C | 3-pyridyl |
| AW6 | $CH_3$ (C-5) | $CH_3$ (C-7) | piperazine | C | 4-pyridyl |

TABLE VI

Compounds of Formula VI (VI)

| Compound | R¹ (position) | R² (position) | R³ (position) | R⁴ (position) | X |
|---|---|---|---|---|---|
| 14 | CH₃ (C-8) | H | OCH₃ (C-2) | H | S |
| 68 | OCH₃ (C-6) | H | CH₃ (C-3) | H | O |

TABLE VII

Compounds of Formula VII (VII)

| Compound | R¹ (position) | R² (position) | R³ |
|---|---|---|---|
| AW7 | CH₃ (C-5) | CH₃ (C-7) | 2-methoxyphenyl |
| AW8 | CH₃ (C-5) | CH₃ (C-7) | 3-methoxyphenyl |
| AW9 | CH₃ (C-5) | CH₃ (C-7) | 4-methoxyphenyl |
| AW10 | CH₃ (C-5) | CH₃ (C-7) | 2-pyridyl |
| AW11 | CH₃ (C-5) | CH₃ (C-7) | 3-pyridyl |
| AW12 | CH₃ (C-5) | CH₃ (C-7) | 4-pyridyl |

In certain embodiments, compounds of Formulae I-VI include compounds having the following structures:

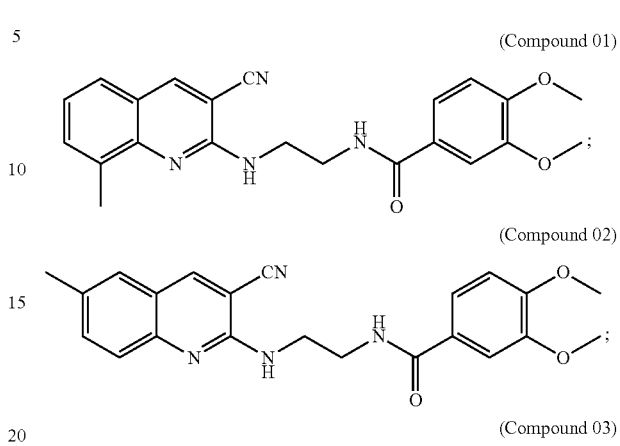

(Compound 01)

(Compound 02)

(Compound 03)

(Compound 05)

(Compound 08)

(Compound 09)

(Compound 10)

57
-continued
(Compound 14)
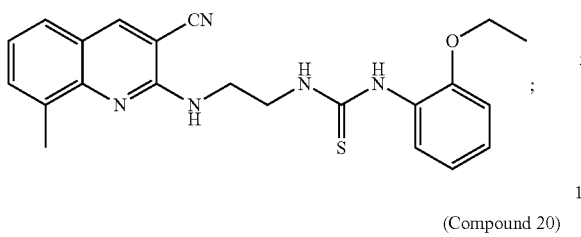
(Compound 20)
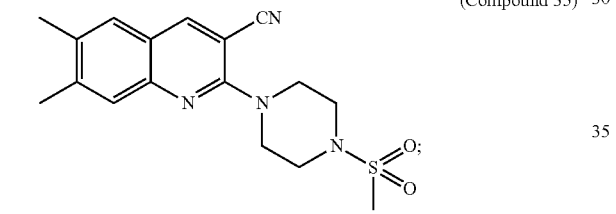
(Compound 22)
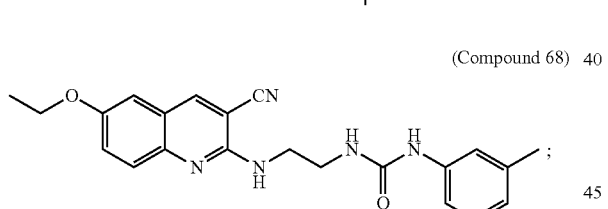
(Compound 35)
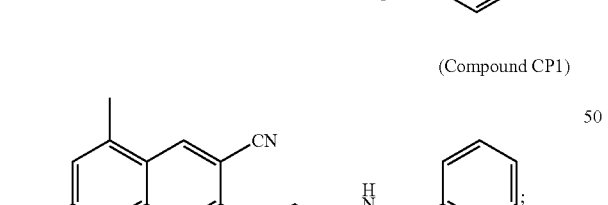
(Compound 68)
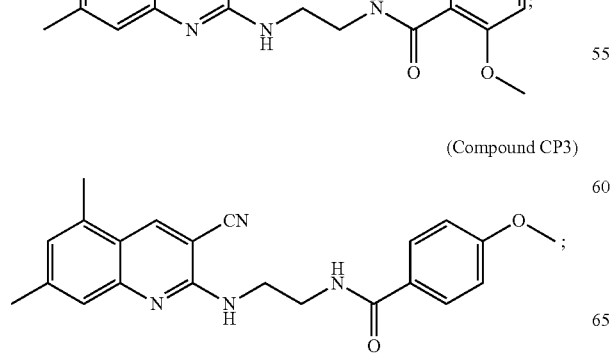
(Compound CP1)
(Compound CP3)
58
-continued
(Compound CP4)
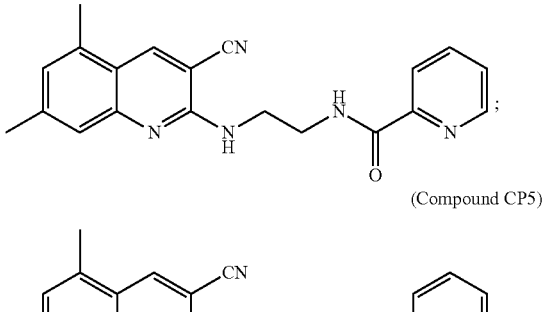
(Compound CP5)
(Compound CP6)
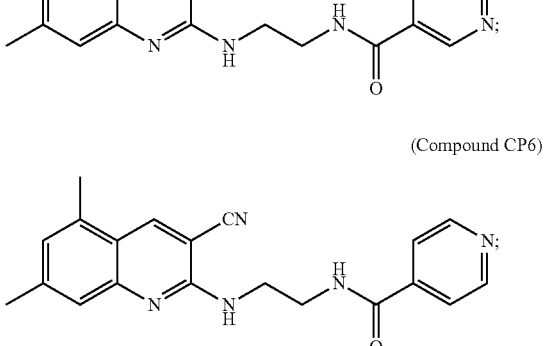
(Compound AW1)
(Compound AW2)
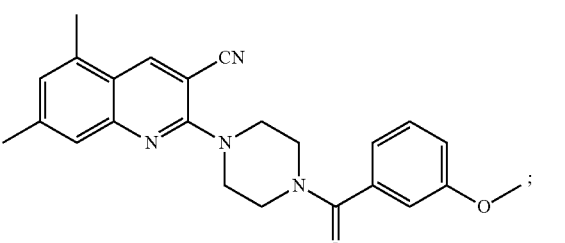
(Compound AW3)

(Compound AW4)
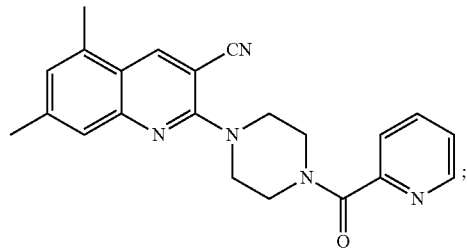
(Compound AW5)
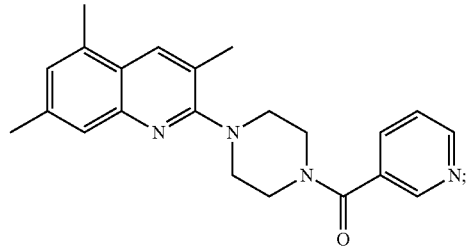
(Compound AW6)
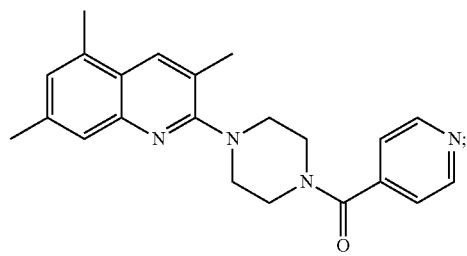
(Compound AW7)
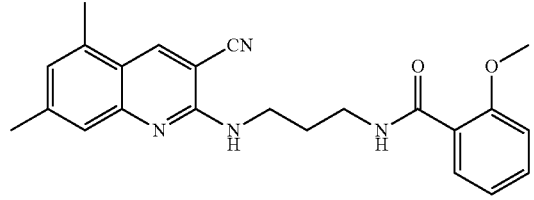
(Compound AW8)
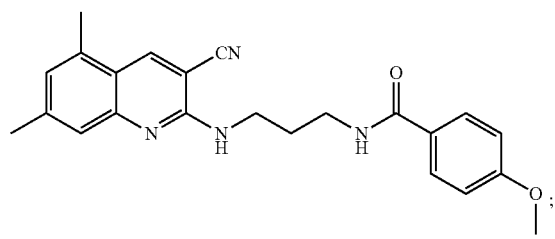
(Compound AW9)
(Compound AW10)
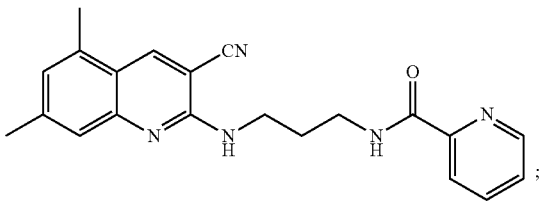
(Compound AW11)
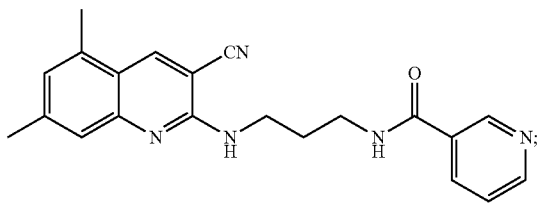
(Compound AW12)
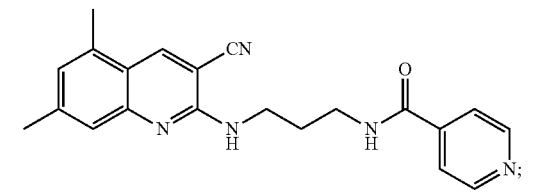
(Compound 100)
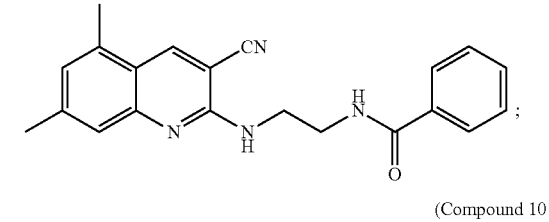
(Compound 101)
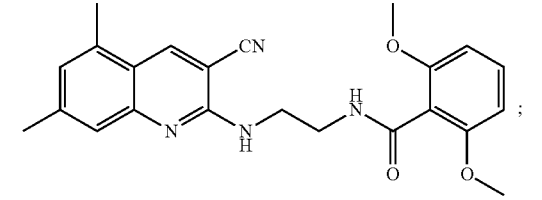
(Compound 102)
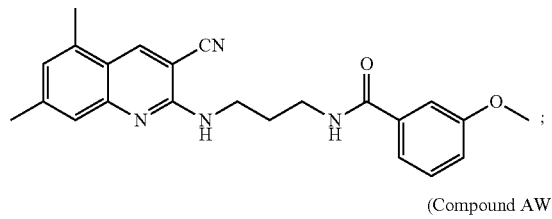
(Compound 103)
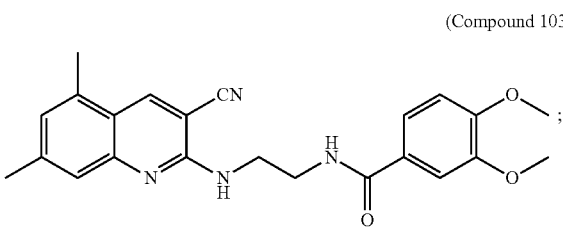

-continued

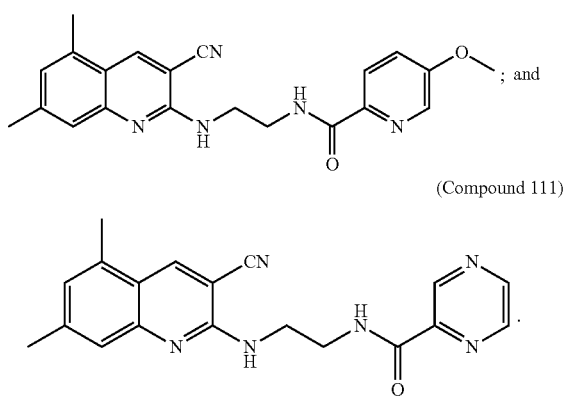

(Compound 110)

(Compound 111)

As referred to herein and/or in the accompanying figures, Compound 01 may also be known as Compound CoPo-01; Compound 02 may also be known as Compound CoPo-02; Compound 03 may also be known as Compound CoPo-03; Compound 05 may also be known as Compound CoPo-05; Compound 08 may also be known as Compound CoPo-08; Compound 09 may also be known as Compound CoPo-09; Compound 10 may also be known as Compound CoPo-10; Compound 14 may also be known as Compound CoPo-14; Compound 20 may also be known as Compound CoPo-20; Compound 22 may also be known as Compound CoPo-22; Compound 35 may also be known as Compound CoPo-35; Compound 68 may also be known as Compound CoPo-68; Compound 100 may also be known as Compound CoPo-100; Compound 101 may also be known as Compound CoPo-101; Compound 102 may also be known as Compound CoPo-102; Compound 103 may also be known as Compound CoPo-103; Compound 110 may also be known as Compound CoPo-110; and Compound III may also be known as Compound CoPo-111.

Analog and Derivative Compounds

Also provided by the present disclosure are analogs and derivatives of the subject compounds described above. The terms "analog" and "derivative" refers to a molecule which is structurally similar or has the same function or activity as the subject cyanoquinoline-containing compounds. Such analogs and derivatives of the subject compounds can be screened for efficiency in binding to and modulating the activity of a mutant CFTR, such as ΔF508-CFTR.

In some embodiments, in silico modeling can be used to screen libraries of analog or derivative compounds. For example, protein-ligand docking can be used to predict the position and orientation of a ligand (a small molecule) when it is bound to a protein such as a mutant-CFTR. Docking techniques can be for a variety of purposes, most notably in the virtual screening of large databases of available chemicals in order to select likely drug candidates. An exemplary in silico modeling program suitable for use with the subject method is the PREDICT™ 3D Modeling Technology (Predix Pharmaceuticals, Woburn Mass.), described in greater detail in Becker et al., *PNAS* 101(3 1): 11304-1 1309 (2004).

Pharmaceutical Preparations

Also provided by the present disclosure are pharmaceutical preparations of the subject compounds. Pharmaceutically acceptable derivatives include those that retain the essential characteristic of the parent compound, namely, the ability to activate a mutant-CFTR, such as ΔF508-CFTR. The pharmaceutically acceptable derivatives may further include one or more additional features that impart a pharmacological or biological property that benefits the compound's manufacture, handling, potency, selectivity, and/or pharmacokinetic parameters.

The subject compounds can be incorporated into a variety of formulations for therapeutic administration by a variety of routes. More particularly, the compounds of the present embodiments can be formulated into pharmaceutical compositions by combination with appropriate, pharmaceutically acceptable carriers, diluents, excipients and/or adjuvants, and may be formulated into preparations in solid, semi-solid (e.g., gel), liquid or gaseous forms, such as tablets, capsules, powders, granules, ointments, solutions, suspensions, suppositories, injections, inhalants, aerosols and the like. In certain embodiments, pharmaceutically acceptable compositions do not include detectable amounts of dimethyl sulfoxide (DMSO). In certain embodiments, pharmaceutically acceptable compositions do not include solvents, such as dimethyl sulfoxide (DMSO) that may cause undesirable biological effects. The formulations may be designed for administration to subjects or patients in need thereof via a number of different routes, including oral, buccal, rectal, parenteral, intraperitoneal, intradermal, intratracheal, transdermal, etc., administration. In certain embodiments, the pharmaceutical compositions are not administered transdermally.

Pharmaceutically acceptable excipients usable with the embodiments, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. The composition or formulation to be administered will, in any event, contain a quantity of the agent adequate to achieve the desired state in the subject being treated.

Dosage Forms

In pharmaceutical dosage forms, the subject compounds of the embodiments may be administered in the form of their pharmaceutically acceptable salts, or they may also be used alone or in appropriate association, as well as in combination, with other pharmaceutically active compounds. The following methods and excipients are merely examples and are in no way limiting.

The agent can be administered to a host using any available conventional methods and routes suitable for delivery of conventional drugs, including systemic or localized routes. In general, routes of administration contemplated by the embodiments include, but are not necessarily limited to, enteral, parenteral, or inhalational routes, such as intrapulmonary or intranasal delivery.

Conventional and pharmaceutically acceptable routes of administration include intranasal, intrapulmonary intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

In one embodiment of particular interest, the compounds of the embodiments are administered in aerosol formulation via intrapulmonary inhalation. The compounds of the embodiments can be formulated into pressurized acceptable propellants such as dichlorodifluoromethane, propane, nitrogen and the like.

Mechanical devices designed for intrapulmonary delivery of therapeutic products, include but are not limited to nebulizers, metered dose inhalers, and powder inhalers, all of which are familiar to those of skill in the art. Specific examples of devices suitable for the practice of the embodiments are the Ultravent nebulizer, manufactured by Mallinckrodt, Inc., St. Louis, Mo.; the Acorn I1 nebulizer, manufactured by Marquest Medical Products, Englewood, Colo.; the Ventolin metered dose inhaler, manufactured by Glaxo Inc., Research Triangle Park, N.C.; the Spinhaler powder inhaler, manufactured by Fisons Corp., Bedford, Mass.; the "standing cloud" device of Inhale Therapeutic Systems, Inc., San Carlos, Calif.; the AIR inhaler manufactured by Alkennes, Cambridge, Mass.; and the AERx pulmonary drug delivery system manufactured by Aradigm Corporation, Hayward, Calif. Other examples of devices suitable for the practice of the embodiments are the PARI LC PLUS®, the PARI LC STAR®, and the PARI BABY™ nebulizers by PARI Respiratory Equipment, Inc., Monterey, Calif.

Formulations for use with a metered dose inhaler device may include a finely divided powder. This powder may be produced by lyophilizing and then milling a liquid conjugate formulation and may also contain a stabilizer such as human serum albumin (HSA). In some instances, more than 0.5% (w/w) HSA is added. Additionally, one or more sugars or sugar alcohols may be added to the preparation if necessary. Examples include lactose maltose, mannitol, sorbitol, sorbitose, trehalose, xylitol, xylose, combinations thereof, and the like. The amount added to the formulation can range from about 0.01 to 200% (w/w), preferably from approximately 1 to 50%, of the conjugate present. Such formulations may then be lyophilized and milled to the desired particle size.

The properly sized particles may then be suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants may include sorbitan trioleate and soya lecithin, and the like. Oleic acid may also be useful as a surfactant. This mixture may then be loaded into the delivery device. An example of a metered dose inhaler suitable for use in the embodiments is the Ventolin metered dose inhaler, manufactured by Glaxo Inc., Research Triangle Park, N.C.

Formulations for powder inhalers may comprise a finely divided dry powder containing conjugate and may also include a bulking agent, such as lactose, sorbitol, sucrose, or mannitol in amounts which facilitate dispersal of the powder from the device, e.g., 50% to 90% by weight of the formulation. The particles of the powder may have aerodynamic properties in the lung corresponding to particles with a density of about 1 $g/cm^2$ having a median diameter less than 10 micrometers, preferably between 0.5 and 5 micrometers, most preferably of between 1.5 and 3.5 micrometers. An example of a powder inhaler suitable for use in accordance with the teachings herein is the Spinhaler powder inhaler, manufactured by Fisons Corp., Bedford, Mass. The powders for these devices may be generated and/or delivered by methods disclosed in U.S. Pat. Nos. 5,997,848, 5,993,783, 5,985,248, 5,976,574, 5,922,354, 5,785,049 and 5,654,007.

For oral preparations, the subject compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

Methods of administration of the agent through the skin or mucosa include, but are not necessarily limited to, topical application of a suitable pharmaceutical preparation, transdermal transmission, injection, iontophoresis, and epidermal administration. For transdermal transmission, absorption promoters or iontophoresis are suitable methods. Iontophoretic transmission may be accomplished using "patches" which deliver their product continuously via electric pulses through unbroken skin for periods of several days or more.

The subject compounds of the embodiments can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agent can also be delivered to the subject by enteral administration. Enteral routes of administration include, but are not necessarily limited to, oral and rectal (e.g., using a suppository) delivery.

Furthermore, the subject compounds can be made into suppositories by mixing with a variety of bases such as emulsifying bases or water-soluble bases. The compounds of the embodiments can be administered rectally via a suppository. The suppository can include vehicles such as cocoa butter, carbowaxes and polyethylene glycols, which melt at body temperature, yet are solidified at room temperature.

Dosages

Depending on the subject and condition being treated and on the administration route, the subject compounds may be administered in dosages of, for example, 0.1 μg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is one which provides up to about 1 µg to about 1,000 µg or about 10,000 µg of subject composition of the to reduce a symptom in a subject animal.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the embodiments. Similarly, unit dosage forms for injection or intravenous administration may comprise the compound(s) in a composition as a solution in sterile water, normal saline or another pharmaceutically acceptable carrier.

Combination Therapy

For use in the subject methods, the subject compounds may be formulated with or otherwise administered in combination with other pharmaceutically active agents, including other CFTR-activating agents. The subject compounds may be used to provide an increase in the effectiveness of another chemical, such as a pharmaceutical (e.g., other CFTR-activating agents, or agents potentiate gating defective mutant-CFTR), or a decrease in the amount of another chemical, such as a pharmaceutical (e.g., other CFTR-activating agents), that is necessary to produce the desired biological effect.

Examples of other CFTR activating agents include, but are not limited to, enhancers of intracellular cAMP levels, such as for example, but not limited to, forskolin, rolipram, 8-bromo-cAMP, theophylline, papaverine, cAMP and salts, analogs, or derivatives thereof. Other examples include beta agonists, tobramycin (TOBI®, Chiron Inc., Emeryville, Calif.) and curcumin (Egan et al., (2004) *Science* 304:600-603). The compounds of the embodiments may also be used in combination with specific mutant CFTR activators, such as correctors and/or potentiators. Examples of mutant-CFTR potentiating agents include, but are not limited to, phenylglycine containing compounds and sulfonamide containing compounds described in WO2005/120497 and WO2009/051910, the disclosures of each of which are incorporated herein by reference in their entirety.

The compounds described above may also be combined with other therapies for CF, including oral corticosteroids, ibuprofen, ribovarin or antibiotics such as dicloxacillin, cephalosporin, cephalexin, erythromycin, amoxicillin-clavulanate, ampicillin, tetracycline, trimethoprim-sulfamethoxazole, chloramphenicol ciprofloxacin, tobramycin, gentamicin, cephalosporins, monobactams and the like.

The compounds described herein for use in combination therapy with the compounds of the embodiments may be administered by the same route of administration (e.g. intrapulmonary, oral, enteral, etc.) that the 'compounds are administered. In the alternative, the compounds for use in combination therapy with the compounds of the embodiments may be administered by a different route of administration that the compounds are administered.

Methods

Methods for Increasing Chloride Ion Permeability of a Mutant-CFTR Cell

The present disclosure provides methods for increasing ion permeability of a cell that produces mutant-CFTR protein, with cells having gating defective and/or a folding or processing defective mutant-CFTR being of interest, such as cells having a ΔF508-CFTR. In certain embodiments, the method involves contacting the cell with a compound in an amount effective to activate and/or correct the folding or processing defect of a mutant-CFTR protein and increase ion permeability of the cell. In some embodiments, the cell contains a recombinant expression cassette that encodes said mutant-CFTR protein. In other embodiments, the cell contains a genome that encodes said mutant-CFTR protein. In yet other embodiments, the mutant-CFTR is a ΔF508-CFTR. In another embodiment of interest, a compound of the embodiments is used in the method in combination with a second mutant-CFTR activator, potentiator, corrector or corrector-potentiator.

The present disclosure provides methods for treating a subject having a condition associated with mutant-CFTR, which involves administering to the subject a therapeutically effective amount of a pharmaceutical composition of the embodiments. The present disclosure also provides a method of increasing ion permeability of a cell producing a mutant-CFTR protein, which involves contacting the cell with an effective amount of the pharmaceutical composition of the embodiments so as to increase CFTR-mediated ion permeability of the cell. In some embodiments, the condition is cystic fibrosis. In some embodiments, the subject, after treatment, has a decrease in mucous or bacterial titer in their lungs, a decrease in coughing or wheezing, a decrease in pancreatic insufficiency, or a decrease in electrolyte levels in their sweat. In some embodiments, the subject is a non-human animal. In some embodiments, the subject is human. In some embodiments, the animal is a mammal. In some embodiments, the mutant-CFTR is a ΔF508-CFTR.

In certain embodiments, the mutant-CFTR protein is present on the plasma membrane of the cell. Methods of detecting mutant-CFTR protein presence on the plasma membrane are well known in the art and can include but are not limited to, for example, labeling a molecule that binds to CFTR protein with a fluorescent, chemical or biological tag. Examples of molecules that bind to CFTR protein include, without limitation, antibodies (monoclonal and polyclonal), FAB fragments, humanized antibodies and chimeric antibodies. For an example of an antibody that binds to CFTR protein, see, e.g. U.S. Pat. No. 6,201,107.

In certain embodiments, the cell has increased permeability to chloride ions, and the contacting of the cell with a compound of the embodiments, increases the rate of chloride ion transport across the plasma membrane of the cell. Contacting the cell with a compound of the embodiments may increase the activity of mutant-CFTR protein to increase ion transport and/or correct the folding or processing of mutant-CFTR protein to increase ion transport.

In certain embodiments, the ion transport activity of mutant-CFTR, or the permeability of a cell to ions, is increased by 10% or more, 20% or more, 50% or more, 100% or more, 150% or more, 200% or more, 300% or more, 400% or more, 500% or more, 800% or more, or 1000% or more. In certain embodiments, where there is no detectable ion transport activity of mutant-CFTR or permeability of a cell to ions, contacting of the cell with a compound of the embodiments causes detectable activity of mutant-CFTR or permeability of a cell to ions.

Activation of mutant-CFTR and/or ion permeability may be measured using any convenient methods that may use molecular markers, e.g., a halide sensitive GFP or another molecular marker (e.g., Galietta et al., (2001) FEBS Lett. 499, 220-224), patch clamp assays, and short circuit assays.

Suitable cells include those cells that have an endogenous or introduced mutant-CFTR gene. Suitable cells include mammalian cell systems (e.g., COS, CHO, BHK, 293, 3T3 cells etc.) harboring constructs that have an expression cassette for expression of mutant-CFTR. The cell used in the subject methods may be a cell present in vivo, ex vivo, or in vitro. As used herein, the term "expression cassette" is meant to denote a genetic sequence, e.g. DNA or RNA, that codes for mutant-CFTR protein, e.g., $\Delta$F508-CFTR. Methods of introducing an expression cassette into a cell are well known in the art. See for example, Sambrook et al., *Molecular Cloning: A Laboratory Manual*. Cold Spring Harbor Laboratory Press, NY, Vols. 1-3 (1989).

Methods of Treating Cystic Fibrosis

The present disclosure also provides methods of treating a subject having a condition associated with mutant-CFTR, e.g., cystic fibrosis. In general, the method involves administering to the subject a compound of the embodiments in an amount effective to activate a mutant-CFTR protein to increase ion transport and thereby treat the condition. In some instances, a compound of the embodiments is administered in combination with a second mutant-CFTR activator, potentiator, corrector or corrector-potentiator, e.g., a compound that enhances intracellular cAMP, e.g., forskolin or a potentiator compound, such as the phenylglycine and sulfonamide containing potentiator compound described in WO 2005/120497 and WO2009/051910, the disclosures of each of which are incorporated herein by reference in their entirety.

The compounds disclosed herein are useful in the treatment of a mutant-CFTR mediated condition, e.g., any condition, disorder or disease, or symptom of such condition, disorder, or disease, that results from the presence and/or activity of mutant-CFTR as compared to wild-type CFTR, e.g., activity of mutant-CFTR in ion transport. Such conditions, disorders, diseases, or symptoms thereof are amenable to treatment by correction of cellular processing or folding of a mutant-CFTR, e.g., activation of mutant-CFTR chloride transport. Cystic fibrosis, a hereditary condition associated with a mutant-CFTR, e.g., $\Delta$F508-CFTR, is an example of a condition that is treatable using the compounds of the embodiments. Use of the compounds of the embodiments in combination with a second mutant CFTR activator, potentiator, corrector or corrector-potentiator is of interest in certain embodiments.

The above methods may be used to treat CF and its symptoms in humans or in animals. Several animal models for CF are known in the art. For example, Engelhardt et al. (*J. Clin. Invest.* 90: 2598-2607, 1992) developed an animal model of the human airway, using bronchial xenografts engrafted on rat tracheas and implanted into nude mice. More recently transgenic models of cystic fibrosis have been produced (e.g., Clarke et al., *Science* 257: 1125-1128, 1992; Dorin et al., *Nature* 359: 21 1-215, 1992). With the recent advances of nuclear transfer and stem cell transformation technologies, the alteration of a wild type CFTR gene in an animal to make it into a mutant-CFTR gene is possible for a wide variety of animals.

Many of these animals show human CF symptoms. In particular, many of these animals showed measurable defects in ion permeability of airway and intestinal epithelia, similar to those demonstrable in human CF tissues, and a susceptibility to bacterial infection. Furthermore, most of the deficient mice had intestinal pathology similar to that of meconium ileus. Also, there appeared to be no prenatal loss from litters produced from crosses between heterozygotes.

Animals suitable for treatment using the subject methods include any animal with a mutant-CFTR related condition, particularly a mammal, e.g., non-human primates (e.g., monkey, chimpanzee, gorilla, and the like), rodents (e.g., rats, mice, gerbils, hamsters, ferrets, and the like), lagomorphs, swine (e.g., pig, miniature pig), equine, canine, feline, and the like. Large animals are of particular interest. Transgenic mammals may also be used, e.g. mammals that have a chimeric gene sequence. Methods of making transgenic animals are well known in the art, see, for example, U.S. Pat. No. 5,614,396. For an example of a transgenic mouse with a CFTR defect, see e.g. WO1994/104669.

Such animals may be tested in order to assay the activity and efficacy of the subject compounds. Improvement in lung function can be assessed by, for example, monitoring prior to and during therapy the subject's forced vital capacity (FVC), carbon monoxide diffusing capacity (DLco), and/or room air $pO_2>55$ mmHg at rest. Significant improvements in one or more of these parameters are indicative of efficacy. It is well within the skill of the ordinary healthcare worker (e.g., clinician) provide adjust dosage regimen and dose amounts to provide for optimal benefit to the patient according to a variety of factors (e.g., patient dependent factors such as the severity of the disease and the like), the compound administered, and the like).

Subjects Suitable for Treatment

Subjects suitable for treatment with a method of the embodiments include individuals having mutant-CFTR protein-mediated condition disorder or disease, or symptom of such condition, disorder, or disease that results from or is correlated to the presence of a mutant-CFTR, usually two alleles of the mutant CFTR. Moreover, subjects suitable for treatment with a method of the embodiments include individuals with CF. Of interest in many embodiments is the treatment of humans with CF.

Symptoms of mutant-CFTR protein-mediated conditions include meconium ileus, liver disease including biliary tract obstruction and stenosis, pancreatic insufficiency, pulmonary disease including chronic *Pseudomonas aeruginosa* infections and other infections of the lung, infertility associated with abnormal vas deferens development or abnormal cervical mucus, and carcinoma including adenocarcinoma.

The corrector-potentiator compounds of the embodiments affect the ion transport capability of the mutant-CFTR by increasing the reduced level of ion transport mediated by a mutant-CFTR, such as the $\Delta$F508-CFTR. As such, the corrector-potentiator compounds of the embodiments have clinical utility in treating a subset of CF patients that have mutations in the CFTR gene that results a mutant-CFTR that is expressed in the plasma membrane and has reduced chloride conductance capability due to folding or cellular processing (i.e., the mutant-CFTR is folding or cellular processing defective). As such, the corrector-potentiator compounds of the embodiments have clinical utility in treating CF patients having a folding or cellular processing mutant-CFTR, such as $\Delta$F508-CFTR. The corrector-potentiator compounds of the present disclosure also affect the ion transport capability of the mutant-CFTR by increasing the reduced level of ion transport mediated by a mutant-CFTR, such as the $\Delta$F508-CFTR, G551D-CFTR, G1349D-CFTR, or D1152H-CFTR. As such, the corrector-potentiator compounds of the present disclosure also have clinical utility in treating a subset of CF patients that have mutations in the CFTR gene that results a mutant-CFTR that is expressed in the plasma membrane and has reduced chloride conductance capability or has abnormal regulation of conductance (i.e., the mutant-CFTR is gating defective). As such, the corrector-potentiator compounds of the present disclosure also have clinical utility in treating CF patients having a gating-defective mutant-CFTR, such as ΔF508-CFTR, G551D-CFTR, G1349D-CFTR, or D1152H-CFTR.

CFTR mutations associated with CF are well known in the art. These mutations can be classified in five general categories with respect to the CFTR protein. These classes of CFTR dysfunction include limitations in CFTR production (e.g., transcription and/or translation) (Class I), aberrant folding and/or trafficking (Class II), abnormal regulation of conduction (Class III), decreases in chloride conduction (Class IV), and reductions in synthesis (Class V). Due to the lack of functional CFTR, Class I, II, and III mutations are typically associated with a more severe phenotype in CF (i.e. pancreatic insufficiency) than the Class IV or V mutations, which may have very low levels of functional CFTR expression. A listing of the different mutations that have been identified in the CFTR gene is as found at the world-wide website of the Cystic Fibrosis Mutation Database at genet.sickkids.on.ca/cgi-bin/WebObjects/MUTATION, incorporated by reference herein in its entirety.

A subject suitable for treatment with a method of the embodiments may be homozygous for a specific mutant-CFTR, i.e. homozygous subjects with two copies of a specific mutant-CFTR, e.g., ΔF508-CFTR. In addition, subjects suitable for treatment with a method of the embodiments may also be compound heterozygous for two different CFTR mutants, i.e., wherein the genome of the subjects includes two different mutant forms of CFTR, e.g., a subject with one copy of ΔF508-CFTR and a copy of different mutant form of CFTR.

In certain embodiments, the mutant-CFTR polypeptide is ΔF508-CFTR. In certain embodiments, the mutant-CFTR polypeptide is G551D-CFTR. In certain embodiments, the mutant-CFTR polypeptide is G1349D-CFTR. In certain embodiments, the mutant-CFTR polypeptide is D152H-CFTR. The present disclosure, however, should not be construed to be limited solely to the treatment of CF patients having this mutant form of CFTR. Rather, the present disclosure should be construed to include the treatment of CF patients having other mutant forms of CFTR with similar characteristics, that result in expression of the mutant-CFTR in the plasma membrane and has reduced chloride conductance capability or has abnormal regulation of conductance.

Methods of Making Cyanoquinoline Compounds

The present disclosure also provides methods of making the cyanoquinoline compounds disclosed herein. In certain embodiments, the cyanoquinoline compounds are synthesized using the following reaction scheme:

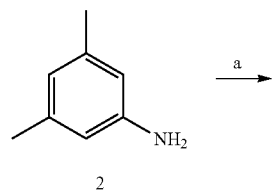

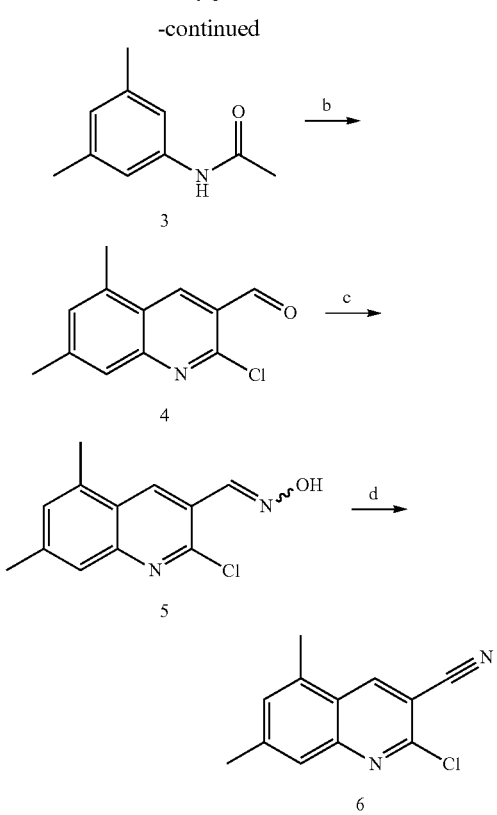

In some instances, the cyanoquinoline core was synthesized starting from 3,5-dimethylaniline 2. Although 3,5-dimethylaniline is used in the reaction scheme described here, any substituted aniline compound may be used as the starting compound for these reactions, such that the final cyanoquinoline compound may have any of a variety of desired substituents on the cyanoquinoline ring. In some cases, dimethylaniline 2 may be acylated to give compound 3. In certain embodiments, a Vilsmeier Haack type reaction is performed on compound 3 to give chloroquinoline carboxaldehyde 4. In some cases, the aldehyde may be condensed with hydroxylamine to give hydroxylimine 5, which may then be converted to nitrile 6 by dehydration with $SOCl_2$.

In certain embodiment, Compound 6 may be linked to a diamine tether (e.g., diamino ethyl, diamino propyl, 1,4-piperazine, and the like). In some cases, an aromatic substitution reaction is used to link Compound 6 to the diamine tether to form a carbonitrile-tether complex, where the Cl of the carbonitrile compound is replaced by a bond to the tether group. Aromatic displacement between various diamines and Compound 6 may allow for diversification of the tethered subunit as shown in the reaction scheme below. For example, 1,2-diamino ethane, 1,4-piperazine and 1,3-diamino propane may be used as the tether portion of the cyanoquinoline compounds. In certain embodiments, the piperazine linker constrains conformational flexibility while the 1,3-diaminopropane linker increases the number potential conformers, as compared to the 1,2-diamino ethyl tether group.

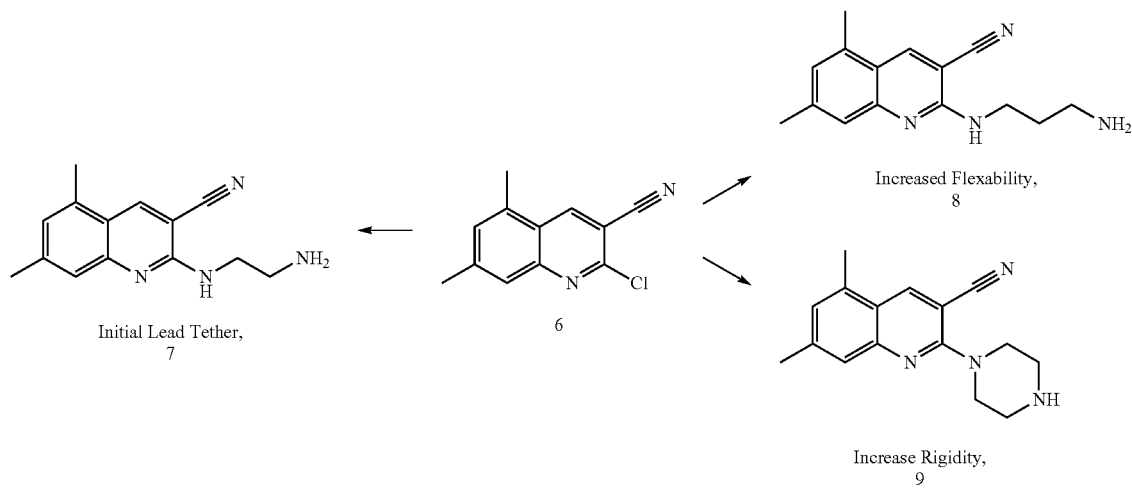 [SMILES: Cc1cc(C)c2cc(C#N)c(NCCCN)nc2c1 ; Cc1cc(C)c2cc(C#N)c(NCCN)nc2c1 ; Cc1cc(C)c2cc(C#N)c(Cl)nc2c1 ; Cc1cc(C)c2cc(C#N)c(N3CCNCC3)nc2c1]

Initial Lead Tether, 7

6

Increased Flexability, 8

Increase Rigidity, 9

In certain embodiments, further diversification of primary or secondary amino products 7, 8 and 9 may be performed by amide coupling reactions, such as, but not limited to, 1-ethyl-3-[3-dimethylaminopropyl]carbodiimide (EDC) mediated amide coupling. For example, aryl acids shown below may be used in the amide coupling reaction, as well as any of a variety of substituted or unsubstituted aryl acids, such that the final cyanoquinoline compound may have any of a variety of desired substituents.

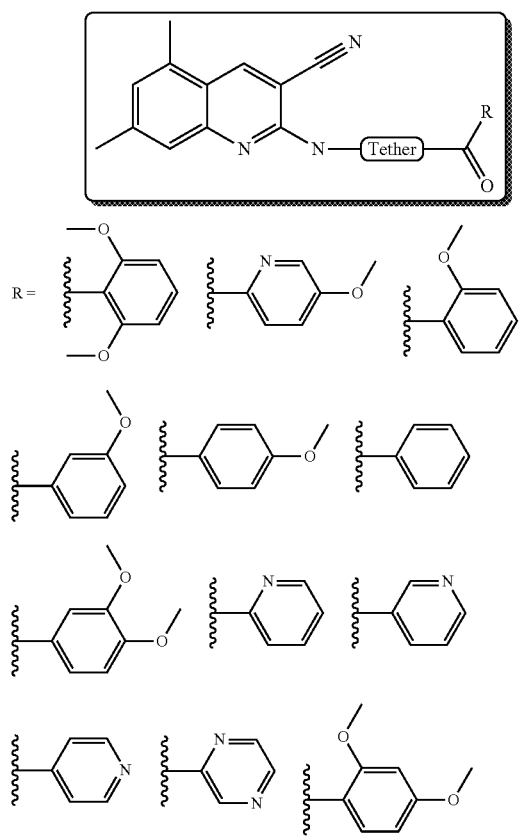

Kits & Systems

Also provided are kits and systems that find use in practicing the subject methods, as described above. The kits typically contain unit doses of the subject compounds, usually in oral or injectable doses. For example, kits and systems for practicing the subject methods may include one or more pharmaceutical formulations that include a corrector-potentiator compound of the embodiments, and optionally one or more additional components. As such, in certain embodiments the kits may include a single pharmaceutical composition present as one or more unit dosages. In yet other embodiments, the kits may include two or more separate pharmaceutical compositions, as well as be part of a system. The term "system" as employed herein refers to a collection of components or agents present in single or disparate compositions that are brought together for the purpose of practicing the subject methods. This includes systems libraries of the compounds of the embodiments as well as individual compounds of the embodiments.

Thus, the kits can include one or more of, depending upon the intended use of the kit, the compositions described herein, such as: a corrector compound of the embodiments. Other optional components of the kit include: buffers, delivery vehicles, delivery systems etc., for administering a corrector compound, and/or for performing a diagnostic assay. The various components of the kit may be present in separate containers or certain compatible components may be pre-combined into a single container, as desired. The kits also may include one or more additional pharmaceuticals or agents for treating a mutant-CFTR.

In addition to the above components, the subject kits may further include instructions for practicing the subject methods, such as an informational package insert describing the use and attendant benefits of the drugs in treating pathological condition of interest. These instructions may be present in the kits in a variety of forms, one or more of which may be present in or on the kit. One form in which these instructions may be present is as printed information on a suitable medium or substrate, e.g., a piece or pieces of paper on which the information is printed, in or on the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

In a specific embodiment, a kit is provided for use in treating a subject suffering from cystic fibrosis. This kit includes a pharmaceutical composition that includes a corrector-potentiator compound of the embodiments and instructions for the effective use of the pharmaceutical composition in a method of treating a subject suffering from cystic fibrosis.

Such instructions may include not only the appropriate handling properties, dosing regiment and method of administration, and the like, but further include instructions to optionally screen and type the subject for mutant-CFTR (e.g., ΔF508-CFTR, G551D-CFTR, G1349D-CFTR, or D1152H-CFTR). This aspect assists the practitioner of the kit in tracking or gauging the potential responsiveness of the subject to treatment with a composition of the embodiments. In another embodiment, the kit includes one or more corrector compositions that are detectably labeled.

EXAMPLES

The following examples are put forth so as to provide those of ordinary skill in the art with a complete disclosure and description of how to make and use the present embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric. Thus it is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

General Material and Methods

The following materials and methods illustrate the synthesis, analysis and testing of embodiments of mutant-CFTR corrector-potentiator compounds.

Cell lines. Fischer rat thyroid (FRT) epithelial cells were stably transfected with ΔF508, G551D or wildtype CFTR. A549 cells stably expressing ΔF508-CFTR were also used as described below. Each of the CFTR-expressing cell lines (and the non-transfected parental cells) were also transfected with halide-sensitive yellow fluorescent protein YFP-H148Q/I152L/F46L. FRT cells were cultured in Coon's modified Ham's F12 medium and A549 cells in DMEM/Ham's F12 (1:1). All media were supplemented with 10% FBS, 2 mM L-glutamine, 100 U/ml penicillin, and 100 μg/ml streptomycin. For primary screening, ΔF508-CFTR-expressing FRT cells were plated in black, 96-well microplates (Costar, Corning Inc.) at 50,000 cells/well. For short-circuit current measurements, cells were cultured on Snapwell permeable supports (Costar, Corning Inc.) at 500,000 cells/insert.

Screening procedures. Screening of compounds for activity was carried out using a Beckman Coulter platform equipped with FLUOstar fluorescence plate readers (Optima; BMG Labtech) with dual syringe pumps and 500±10 nm excitation and 535±15 nm emission filters (Chroma Corp.).

For the corrector assay, FRT cells were grown at 37° C./5% $CO_2$ for 18-24 h and then incubated for 18-24 h with 100 μL of medium containing test compounds (25 μM final concentration). At the time of the assay, cells were washed with PBS and then incubated for 10 min with PBS containing forskolin (20 μM) and genistein (50 μM). For the potentiator assay, FRT cells were grown at 37° C./5% $CO_2$ for 18-24 h and then for 18-24 h at 27° C. At the time of the assay, cells were washed with PBS and then incubated for 10 min with PBS (50 μL) containing forskolin (20 μM) and test compound (0-25 μM final concentration). For both the corrector and potentiator assays, each well was assayed individually for $I^-$ influx by recording fluorescence continuously (200 ms per point) for 2 s (baseline) and then for 12 s after rapid addition of 165 μL PBS in which 137 mM $Cl^-$ was replaced by $I^-$. Initial $I^-$ influx rate was computed by fitting the final 11.5 seconds of the data to an exponential for extrapolation of initial slope, which was normalized for background-subtracted initial fluorescence. All compound plates contained negative controls and positive controls (10 μM Corr-4a for corrector assay; 50 μM genistein for potentiator assay).

Short-circuit current measurements. ΔF508-CFTR-expressing FRT cells were cultured on Snapwell inserts for 7-9 days. For corrector testing, test compounds were incubated with FRT cells for 18-24 h at 37° C. prior to measurements. For potentiator testing, the FRT cells were incubated for 18-24 h at 27° C. prior to measurements. The basolateral solution contained 130 mM NaCl, 2.7 mM KCl, 1.5 mM $KH_2PO_4$, 1 mM $CaCl_2$, 0.5 mM $MgCl_2$, 10 mM glucose, and 10 mM Na-HEPES (pH 7.3). In the apical bathing solution, 65 mM NaCl was replaced by Na gluconate, and $CaCl_2$ was increased to 2 mM. Solutions were bubbled with air and maintained at 37° C. The basolateral membrane was permeabilized with 250 μg/ml amphotericin B. Hemichambers were connected to a DVC-1000 voltage clamp (World Precision Instruments Inc.) via Ag/AgCl electrodes and 1 M KCl agar bridges for recording of short-circuit current.

CFTR Immunoblot. DF508-CFTR expressing FRT cells grown on 6-well plates were treated with Corr-4a (10 mM), Compound 22 (20 mM) or negative control at 37° C. for 24 h. After treatment, cells were washed with PBS and lysed in 20 mM Hepes (pH 7), 150 mM NaCl, 1 mM EGTA and 1% Igepal containing Complete Protease Inhibitor Cocktail (Roche). After pre-clearing, lysates were subjected to SDS-PAGE and analyzed by immunoblot. Proteins were immunodetected using a mouse monoclonal anti-CFTR antibody (M3A7, Millipore) followed by HRP-conjugated anti-mouse IgG, and visualized by chemiluminescence (ECL Plus, Amersham).

Computations. For Compound 22 and Compound AW2, a two-step conformational search was performed. First, candidate conformers were identified via a systematic search in Spartan '10[13] in which each bond between the aryl moieties was given 2-fold rotational freedom ($sp^2$-$sp^2$ bonds) or 3-fold rotational freedom ($sp^2$-$sp^3$ and $sp^3$-$sp^3$ bonds) and atoms in rings were given 3-fold puckering mobility. This procedure resulted in 36 candidate conformations for Compound 22 and 42 candidate conformations for Compound AW2, each within 10 kcal/mol of the lowest energy conformation, as assessed by the MMFF94 force field. These candidates were then subjected to further geometry optimization using the M06-2X/6-31+G(d,p) density functional theory method as implemented in the Gaussian '09 software suite. After this refinement, five conformers within 3 kcal/mol of the lowest energy conformer of 5 and 18 conformers within 3 kcal/mol of the lowest energy conformer of Compound AW2 (four within 2 kcal/mol) were found, as assessed by computed electronic energies with solvent (water) modeled by the SMD continuum solvation model (via single-point calculations). Select conformers were further refined with full solvent optimization and frequency calculations in order to include entropy contributions to the computed relative free energies. Constrained calculations were also performed on some conformers.

Compound 22 Synthesis

Scheme 1:

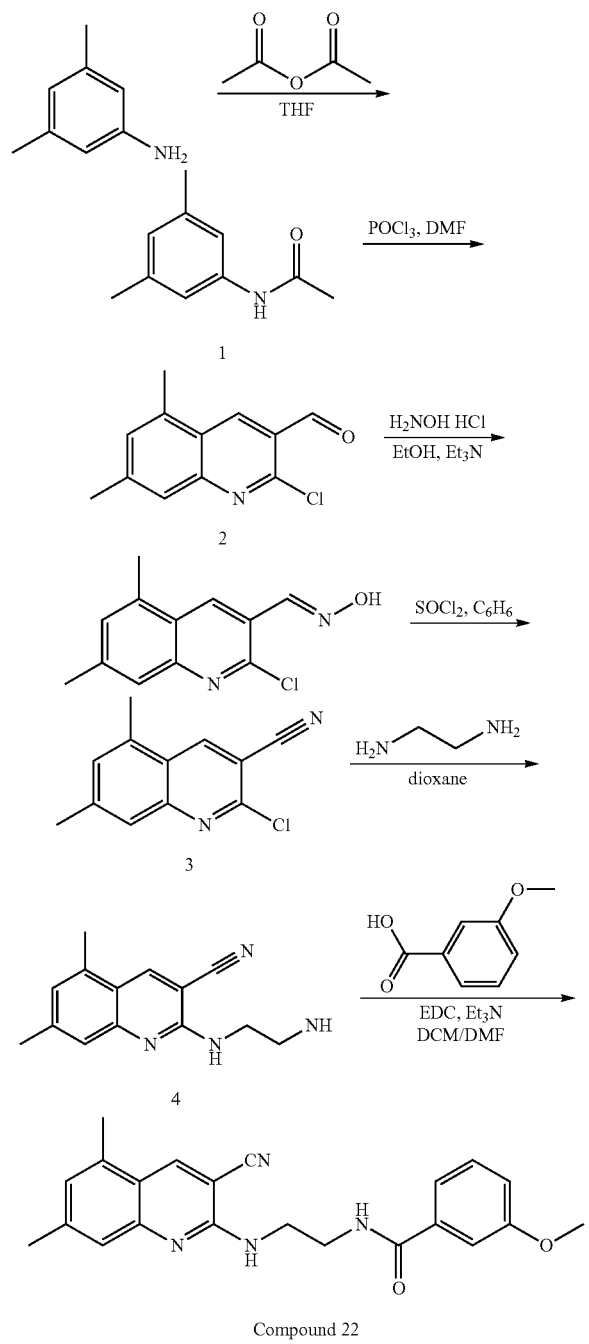

N-(3,5-Dimethylphenyl)acetamide (1). Acetic anhydride (2.84 mL, 30 mmol) was dissolved in dry THF (10 mL), purged with $N_2$ and brought to 0° C. 3,5-Dimethylaniline (1.25 mL, 10 mmol) was then added dropwise. After the addition of the aniline, the reaction was allowed to warm to room temperature and stirred for an additional hour. The solution was then poured over ice and 1 M NaOH (aq) was added until the pH was between 12 and 14. The precipitate was filtered, dissolved in DCM and dried over $Na_2SO_4$. The drying agent was filtered and solvent was removed under reduced pressure to afford pure product in 99% yield as a white solid.

2-Chloro-5,7-dimethylquinoline-3-carbaldehyde (2). Phosphorous oxychloride (6.52 mL, 70 mmol) and dry DMF (1.94 mL, 25 mmol) were refluxed for 2 h under $N_2$. Acetamide 1 (1.632 g, 10 mmol) was added to the reaction solution as a solid and stirred at room temperature for an additional 3 h. The solution was poured slowly over ice, diluted with water (200 mL) and neutralized with solid $K_2CO_3$. The precipitate was then filtered, dissolved in chloroform and dried over $Na_2SO_4$. The drying agent was filtered and solvent was removed under reduced pressure to afford pure product as an orange solid in 95% yield.

2-Chloro-5,7-dimethylquinoline-3-carbonitrile (3). Aldehyde 2 (1.095 g, 5 mmol), hydroxylamine hydrochloride (0.365 g, 5.25 mmol) and triethylamine (1.00 mL, 7 mmol) were combined in ethanol (50 mL). The solution was refluxed for 3 h and then the ethanol was removed under reduced pressure. HCl (1 M, aq, 100 mL) was added to the crude material and product was extracted with dichloromethane (DCM) (100 mL). The organic layer was separated and dried over $Na_2SO_4$, the drying agent was removed by filtration, and the solvent was removed under reduced pressure. The crude product was then dissolved in 50 mL of dry benzene. Thionyl chloride (0.73 mL, 10 mmol) was added dropwise to the solution and the reaction was refluxed for 4 h under $N_2$. The solution was allowed to cool to room temperature, then the benzene and excess thionyl chloride were removed under reduced pressure to afford the known product 3 in 93% yield as a light brown solid [$^1$H NMR (400 MHz, CDCl$_3$) δ 8.62 (s, 1H), 7.62 (s, 1H), 7.33 (s, 1H), 2.66 (s, 3H), 2.54 (s, 3H)], which in some instances was used directly in the next reaction.

General Procedure for Aromatic Substitution of Carbonitrile 3 with a Diamine Tether. Carbonitrile 3 (1.083 g, 5 mmol) and 1,2-dimethylaminoethane (1.00 mL, 15 mmol) was refluxed in dioxane (50 mL). The reaction was allowed to cool to room temperature and dioxane was removed under reduced pressure. The crude product was suspended in saturated $NH_4Cl$ (aq) and filtered. The solids were washed with diethylether and allowed to dry on filter paper under vacuum to give the carbonitrile-tether complex.

General Procedure for Amide Coupling Reactions. EDC hydrochloride (0.192 g, 1 mmol), acid (1 mmol) and triethylamine (0.14 mL, 2.5 mmol) were dissolved in dry DCM (10 mL). The reaction was stirred at room temperature for 30 min. The carbonitrile-tether complex from the previous reaction (0.201 g, 1 mmol) dissolved in 5 mL dry DCM was added dropwise to the solution and reaction stirred for 18 h. The reaction was diluted with DCM (50 mL) and washed with 1M $NaHSO_4$ (aq, 2×100 mL). Organics were dried over $Na_2SO_4$, filtered and solvent was removed under reduced pressure. The crude product was then purified by flash chromatography.

For example, the aromatic substitution and amide coupling reactions of carbonitrile 3 to give Compound 22 were performed as follows:

2-((2-Aminoethyl)amino)-5,7-dimethylquinoline-3-carbonitrile (4). Carbonitrile 3 (1.083 g, 5 mmol) and 1,2-aminoethane (1.00 mL, 15 mmol) was refluxed in dioxane (50 mL). The reaction was allowed to cool to room temperature and dioxane was removed under reduced pressure. The crude product was suspended in saturated NH$_4$Cl (aq) and filtered. The solids were washed with diethylether and allowed to dry on filter paper under vacuum to give the known product 4 in 80% yield [$^1$H NMR (400 MHz, CDCl$_3$) δ 8.31 (s, 1H), 7.32 (s, 1H), 6.92 (s, 1H), 5.64 (t, J=4.8, 1H), 3.65 (q, J=5.7, 2H), 3.01 (t, J=6.0, 2H), 2.52 (s, 3H), 2.42 (s, 3H)], which was used directly in the next reaction.

N-(2-((3-Cyano-5,7-dimethylquinolin-2-yl)amino)ethyl)-3-methoxybenzamide (Compound 22). EDC hydrochloride (0.192 g, 1 mmol), m-anisic acid (0.152 g, 1 mmol) and triethylamine (0.14 mL, 2.5 mmol) were dissolved in dry DCM (10 mL). The reaction was stirred at room temperature for 30 min. Carbonitrile 4 (0.201 g, 1 mmol) dissolved in 5 mL dry DCM was added dropwise to the solution and reaction stirred for 18 h. The reaction was diluted with DCM (50 mL) and washed with 1M NaHSO$_4$ (aq, 2×100 mL). Organics were dried over Na$_2$SO$_4$, filtered and solvent was removed under reduced pressure. The crude product was then purified by flash chromatography (4:1 hexane:ethyl acetate mobile phase) to produce a light yellow solid (Compound 22) in 73% yield. $^1$H NMR (400 MHz, CDCl$_3$) δ 8.35 (s, 1H), 8.13 (s, 1H), 7.32 (s, 1H), 7.28 (s, 1H), 7.20 (d, J=7.5, 1H), 7.13 (t, J=7.8, 1H), 6.98 (s, 1H), 6.95 (d, J=8.1, 1H), 5.82 (s, 1H), 3.91 (q, J=5.3, 2H), 3.79-3.68 (m, 5H), 2.55 (s, 3H), 2.42 (s, 3H); $^{13}$C NMR (100 MHz, CDCl$_3$) δ 168.10, 159.87, 155.10, 144.27, 140.97, 136.27, 135.41, 129.42, 127.13, 124.48, 119.35, 119.23, 117.72, 116.87, 112.46, 94.30, 55.49, 43.39, 41.25, 29.92, 22.21, 18.57. IR (neat): 3380, 3357, 2957, 2925, 2217, 1605, 1583, 1535, 1258. ESI-LCMS m/z [M+H]$^+$= 375.18.

Results

Identification of Cyanoquinoline Correctors/Potentiators of ΔF508-CFTR

Screening of about 110,000 small molecules was done to identify new ΔF508-CFTR corrector scaffolds having high correction efficiency and/or having independent potentiator activity. FIG. 1A shows a schematic of a high-throughput screening procedure used to identify dual-acting ΔF508-CFTR corrector-potentiator compounds. FRT cells co-expressing human ΔF508-CFTR and a halide-sensing YFP were incubated with test compounds at 37° C. (corrector assay) or 27° C. (potentiator assay). ΔF508-CFTR function was assayed in a plate reader from YFP fluorescence quenching in response to iodide addition in the presence of forskolin (20 μM) plus genistein (50 μM) for corrector assay, or forskolin (20 μM) alone for potentiator assay. As shown in FIG. 1A (left), primary screening for corrector activity was done using a cell-based fluorescence assay of iodide influx in which FRT cells expressing ΔF508-CFTR and an iodide-sensitive YFP were incubated with test compounds at 10 μM for 18-24 h prior to assay. Iodide influx was measured by addition of extracellular iodide in the presence of a potentiator (50 μM genistein) and cAMP agonist (20 μM forskolin). Compound efficacy and potency (from concentration-dependence studies) in the corrector assay were compared to reference bithiazole Corr-4a (10 μM) and to low-temperature rescued cells. Active compounds were counter-screened for potentiator activity (FIG. 1A, right) in which iodide influx was measured in the ΔF508-CFTR expressing FRT cells after low-temperature rescue and in the presence of 20 μM forskolin.

Figure 1B:
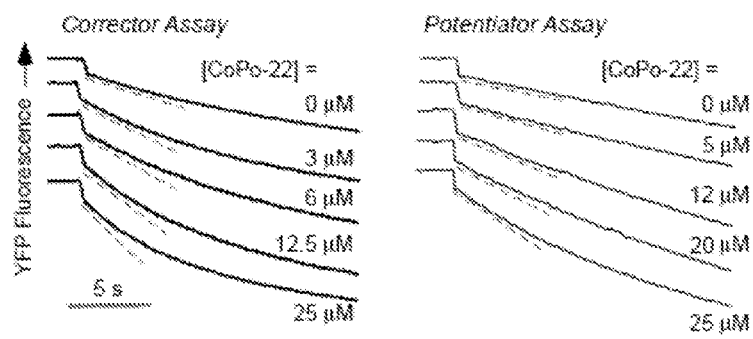
FIG. 1B shows graphs of fluorescence showing iodide influx at different [Compound 22] for corrector assay (left) and potentiator assay (right), according to embodiments of the present disclosure.
Figure 1C:
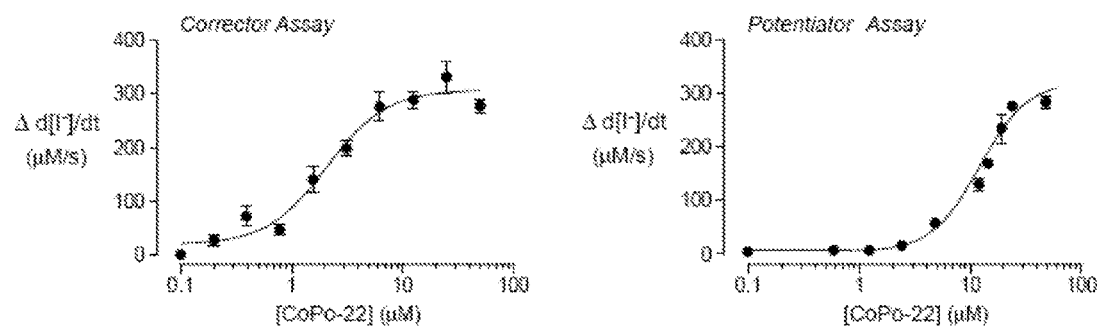
FIG. 1C shows graphs of dose-response data of Compound 22 in corrector (left) and potentiator (right) assays (SEM, n=3), according to embodiments of the present disclosure. Fits to single-site activation model are shown.

Corrector activity was verified by CFTR$_{inh}$-172-inhibition of corrector-dependent iodide influx and inability to increase iodide influx in FRT null cells (data not shown). The cyanoquinoline Compound 22 showed independent potentiator activity. Representative iodide influx data from the corrector (left) and potentiator (right) fluorescence plate reader assays of Compound 22 are shown in FIG. 1B. Concentration-dependence data are shown in FIG. 1C, which shows graphs of dose-response data of Compound 22 in corrector (left) and potentiator (right) assays (SEM, n=3). Fits to single-site activation model are shown. As shown by electrophysiological analysis below, Compound 22 corrector and potentiator maximum efficacy were comparable to those of the bithiazole Corr-4a and the flavone genistein, respectively.

Synthesis and Structure-activity Relationship Analysis of Cyanoquinoline Compounds Cyanoquinoline compounds of the present disclosure were screened to identify corrector-potentiator analogs with improved potency as well as to establish initial structure-activity relationship data of the core cyanoquinoline scaffold. Table VIII summarizes corrector and potentiator activities (EC$_{50}$ and V$_{max}$ from concentration-dependence studies) of active compounds. The structure-activity relationships for corrector and potentiator activities are summarized below in relation to the following general chemical structure for corrector-potentiator compounds according to the present disclosure.

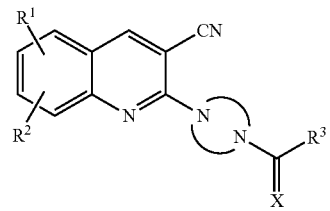

In the chemical structure above, the curved bonds between the two nitrogens each independently represent an optional alkyl or substituted alkyl bond, where the alkyl bond, if present, includes from two to five carbons. For corrector activity, in certain embodiments, corrector-potentiator compounds have greater corrector activity when R$^1$ and R$^2$ represent 5,7-dimethyl substituents on the cyanoquinoline ring. Other corrector-potentiator compounds that may display corrector activity may include 6-methyl or 6-methoxy substituents as R$^1$. In certain embodiments, corrector-potentiator compound have greater corrector activity when R$^3$ is methoxybenzene, dimethoxybenzene or 2-thiophene. Other corrector-potentiator compounds that may display corrector activity may include 1,3-diaminopropane as R$^3$. In certain embodiments, corrector-potentiator compounds may have low corrector activity or be inactive as correctors when —C(=X)R$^2$ is replaced by —SO$_2$Ph. In certain embodiments, corrector-potentiator compounds have greater corrector activity when the optional bond between the two nitrogens is not present. Other corrector-potentiator compounds that may display corrector activity may include an alkyl bond between the two nitrogens, such that the two nitrogens are linked together in a piperazine or diazepane heterocyclic ring structure. In certain embodiments, corrector-potentiator compounds where X is O have greater corrector activity than corrector-potentiator compounds where X is S.

For potentiator activity, in certain embodiments, corrector-potentiator compounds have greater potentiator activity when R$^1$ is 6-methoxy. Other corrector-potentiator compounds that may display potentiator activity may include cyanoquinoline compounds where R$^1$ is 7-methyl or 8-methyl, or where R$^1$ and R$^2$ represent 5,7-dimethyl substituents on the cyanoquinoline ring. In certain embodiments, corrector-potentiator compound have greater potentiator activity when R$^3$ is 2-ethoxybenzene, 2-thiophene or 2-halophenyl, where the halogen is F, Cl or Br. Other corrector-potentiator compounds that may display potentiator activity may have the —C(=X)R$^3$ group replaced by —SO$_2$Ph. In certain embodiments, corrector-potentiator compounds may have low potentiator activity or be inactive as potentiators when —C(=X)R$^3$ is replaced by —(=S)NH$_2$ or —(=S)NHR$^2$. In certain embodiments, corrector-potentiator compounds have similar potentiator activity when the optional bond between the two nitrogens is not present or when there is an alkyl bond between the two nitrogens, such that the two nitrogens are linked together in a piperazine or diazepane heterocyclic ring structure. In certain embodiments, corrector-potentiator compounds where X is O have greater corrector activity than corrector-potentiator compounds where X is S.

Figure 2:
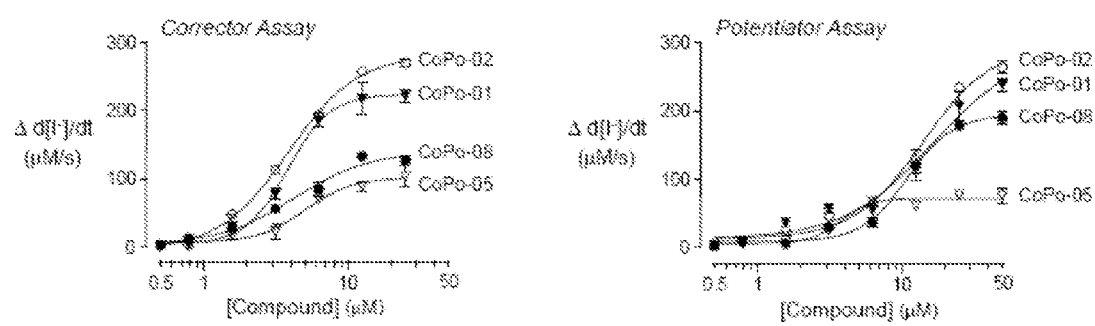
FIG. 2 shows graphs of the concentration-dependence of corrector (left) and potentiator (right) activities of Compound 01, Compound 02, Compound 05 and Compound 08, according to embodiments of the present disclosure.

FIG. 2 shows representative concentration-dependence data for four analogs. Six compounds showed both corrector and potentiator activities. Compound 01 and Compound 02 are structurally similar to Compound 22, and have corrector and potentiator activities comparable to those of Compound 22. Compounds containing heterocycles, such as the thiophene Compound 03 and the benzosulfonamide Compound 05, also show dual activities. Several compounds, such as Compound 14, showed potentiator-only activity. In certain embodiments, replacing the ethylene bridge with a piperazine or 1,4-diazepane ring resulted in compounds that had lower or no corrector activity (e.g., comparing Compound 03 and Compound 20).

Figure 7:
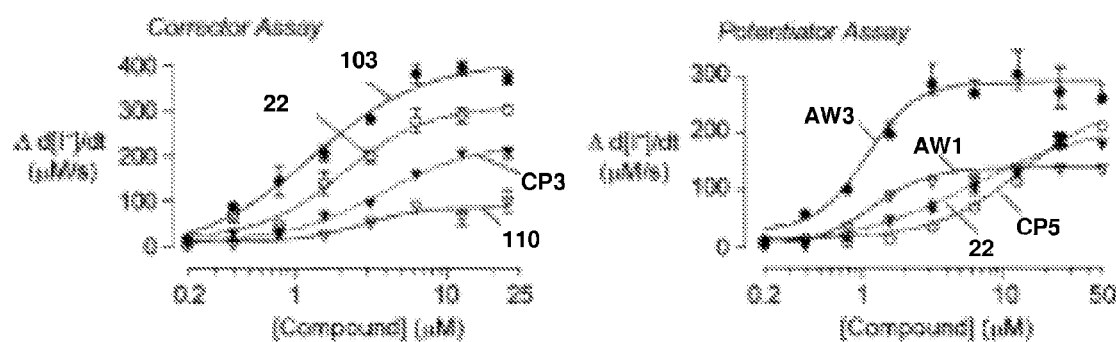
FIG. 7 shows graphs of the concentration-dependence of corrector (left) and potentiator (right) activities of the indicated compounds in FRT cells expressing ΔF508-CFTR measured by iodide (I$^-$) influx, according to embodiments of the present disclosure.

FIG. 7 shows representative concentration-dependence data for Compounds 22, 103, 110, CP3, CP5, AW1 and AW3. Five compounds (e.g, Compounds 22, 103, 110, CP3 and CP5) showed both corrector and potentiator activities. Two compounds, Compounds AW1 and AW3, showed potentiator-only activity.

Table VIII summarizes corrector and potentiator activities (EC$_{50}$ and V$_{max}$ from concentration-dependence studies) of embodiments of certain active compounds.

TABLE VIII

| | Corrector and potentiator activities | | | |
| --- | --- | --- | --- | --- |
| | Corrector | | Potentiator | |
| Compound | EC$_{50}$ (µM) | V$_{max}$ (µM/s) | EC$_{50}$ (µM) | V$_{max}$ (µM/s) |
| 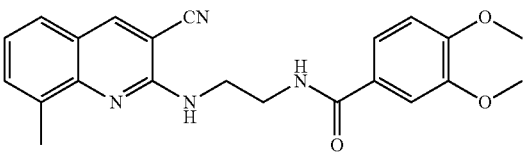 (Compound 01) | 3.8 | 223 | 15 | 250 |
| 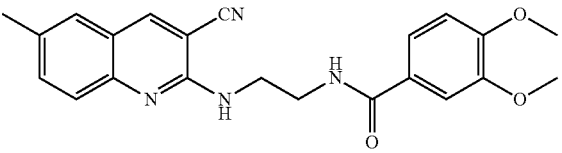 (Compound 02) | 3.9 | 281 | 15 | 297 |
| 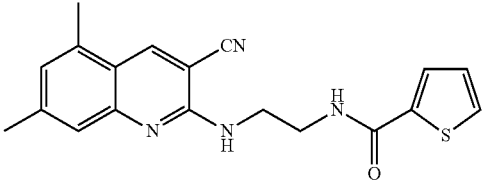 (Compound 03) | 14 | 228 | 14 | 289 |
| 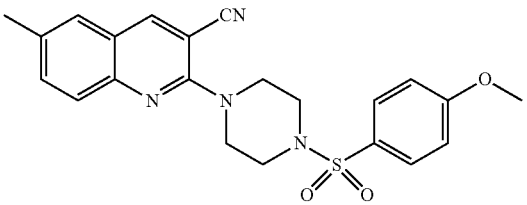 (Compound 05) | 5.0 | 102 | 3.8 | 72 |

TABLE VIII-continued
Corrector and potentiator activities
| Compound | Corrector | | Potentiator | |
|---|---|---|---|---|
| | EC$_{50}$ (μM) | V$_{max}$ (μM/s) | EC$_{50}$ (μM) | V$_{max}$ (μM/s) |
| 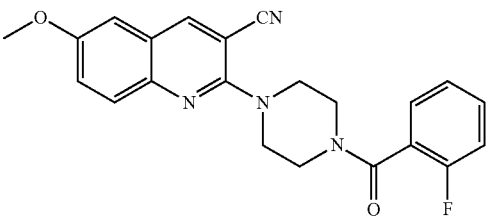 (Compound 08) | 4.2 | 140 | 11 | 195 |
| 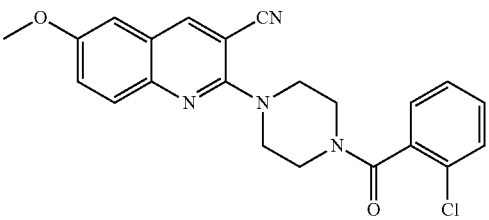 (Compound 09) | inactive | inactive | 13 | 261 |
| 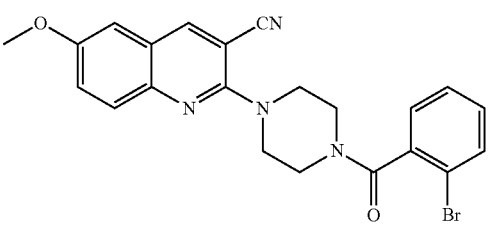 (Compound 10) | inactive | inactive | 5.0 | 235 |
| 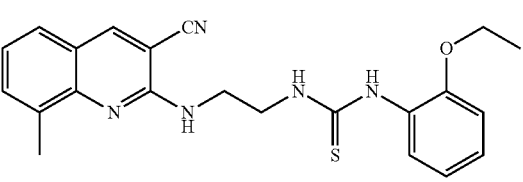 (Compound 14) | inactive | inactive | 6.0 | 275 |
| 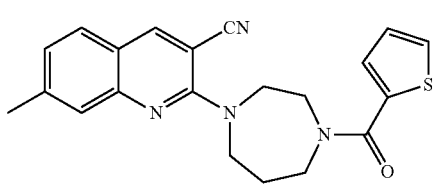 (Compound 20) | inactive | inactive | 13 | 261 |
| 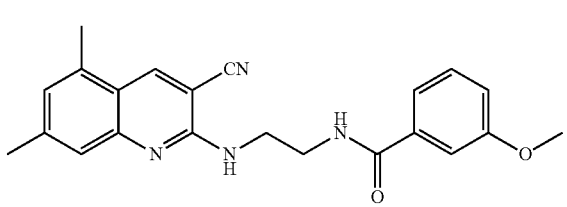 (Compound 22) | 2.2 | 300 | 14 | 306 |

TABLE VIII-continued

Corrector and potentiator activities

| Compound | Corrector | | Potentiator | |
|---|---|---|---|---|
| | $EC_{50}$ (μM) | $V_{max}$ (μM/s) | $EC_{50}$ (μM) | $V_{max}$ (μM/s) |
| (Compound CP1) | 11 | 114 | 2.3 | 154 |
| (Compound CP3) | 3.0 | 172 | 4.1 | 181 |
| (Compound CP4) | inactive | inactive | 1.2 | 80 |
| (Compound CP5) | 15.2 | 223 | 11 | 152 |
| (Compound CP6) | 9.1 | 172 | 10 | 220 |
| (Compound AW1) | inactive | inactive | 1.0 | 129 |

TABLE VIII-continued
| | Corrector | | Potentiator | |
|---|---|---|---|---|
| Compound | $EC_{50}$ (µM) | $V_{max}$ (µM/s) | $EC_{50}$ (µM) | $V_{max}$ (µM/s) |
| 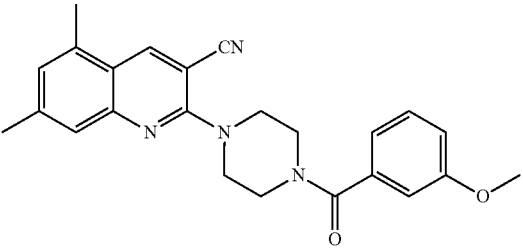<br>(Compound AW2) | inactive | inactive | 1.2 | 200 |
| 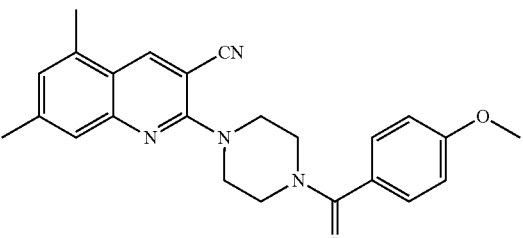<br>(Compound AW3) | inactive | inactive | 1.3 | 281 |
| 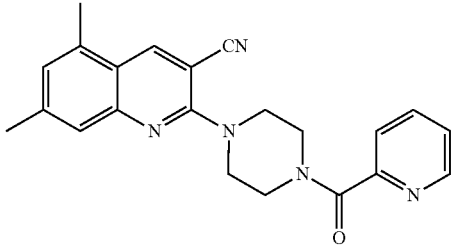<br>(Compound AW4) | inactive | inactive | 7.4 | 102 |
| 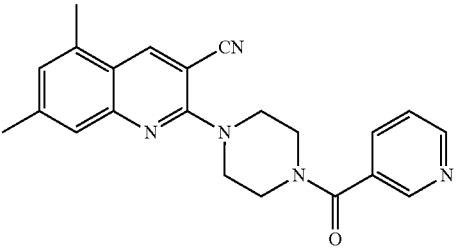<br>(Compound AW5) | inactive | inactive | inactive | inactive |
| 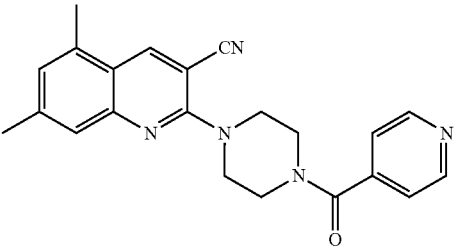<br>(Compound AW6) | inactive | inactive | n/a | n/a |

TABLE VIII-continued
| | Corrector | | Potentiator | |
|---|---|---|---|---|
| Compound | EC$_{50}$ (μM) | V$_{max}$ (μM/s) | EC$_{50}$ (μM) | V$_{max}$ (μM/s) |
| 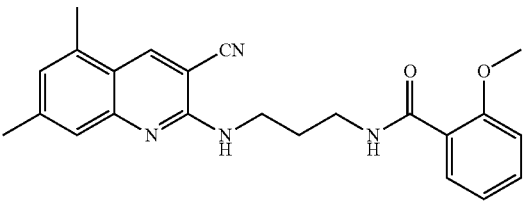 (Compound AW7) | n/a | n/a | n/a | n/a |
| 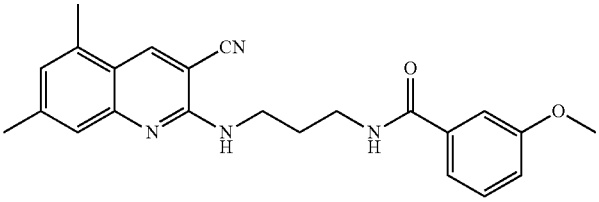 (Compound AW8) | 4.6 | 134 | 4.6 | 147 |
| 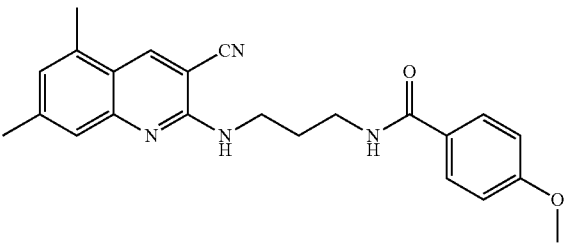 (Compound AW9) | 4.3 | 112 | 5.0 | 231 |
| 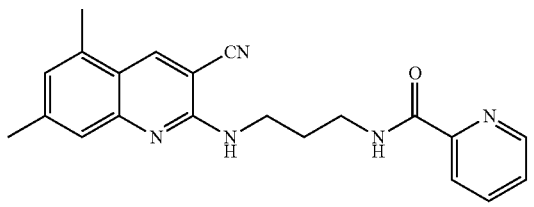 (Compound AW10) | n/a | n/a | 6.1 | 233 |
| 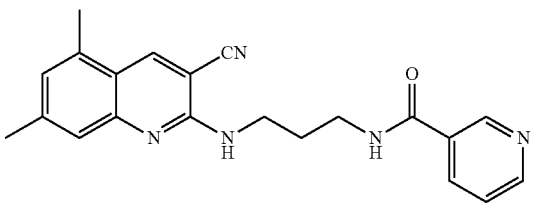 (Compound AW11) | inactive | inactive | 16 | 115 |

TABLE VIII-continued

| | Corrector and potentiator activities | | | |
|---|---|---|---|---|
| | Corrector | | Potentiator | |
| Compound | $EC_{50}$ (μM) | $V_{max}$ (μM/s) | $EC_{50}$ (μM) | $V_{max}$ (μM/s) |
| (Compound AW12) [5,7-dimethylquinoline-3-CN with NH-CH2CH2CH2-NH-C(=O)-pyridin-4-yl] | inactive | inactive | n/a | n/a |

Additional experiments were performed using the protocols described above to test the corrector and potentiator activities ($EC_{50}$ and $V_{max}$ from concentration-dependence studies) of active compounds. Table IX summarizes corrector and potentiator activities ($EC_{50}$ and $V_{max}$ from concentration-dependence studies) of embodiments of certain active compounds.

TABLE IX

| | Corrector and potentiator activities | | | |
|---|---|---|---|---|
| | Corrector | | Potentiator | |
| Compound | $EC_{50}$ (μM) | $V_{max}$ (μM/s) | $EC_{50}$ (μM) | $V_{max}$ (μM/s) |
| (Compound 22) | 2.2 ± 0.3 | 300 | 5.9 ± 0.5 | 216 |
| (Compound CP1) | 11.0 ± 0.9 | 114 | 2.3 ± 0.4 | 154 |
| (Compound CP3) | 3.0 ± 0.3 | 172 | 4.1 ± 1.0 | 181 |

TABLE IX-continued
Corrector and potentiator activities
| Compound | Corrector | | Potentiator | |
|---|---|---|---|---|
| | EC$_{50}$ (μM) | V$_{max}$ (μM/s) | EC$_{50}$ (μM) | V$_{max}$ (μM/s) |
| 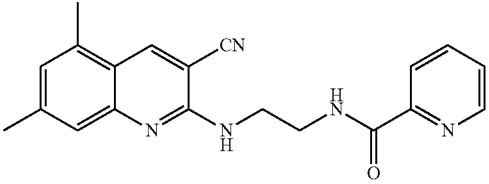 (Compound CP4) | inactive | inactive | 1.2 ± 0.4 | 80 |
| 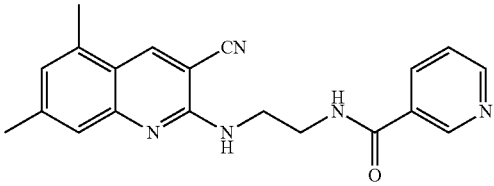 (Compound CP5) | 2.7 ± 0.6 | 151 | 13.2 ± 0.6 | 242 |
| 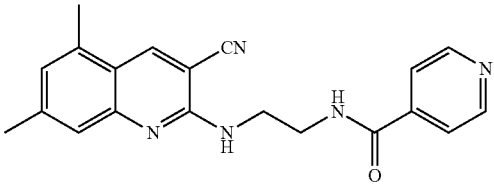 (Compound CP6) | 7.3 ± 0.8 | 176 | 10.0 ± 3.1 | 220 |
| 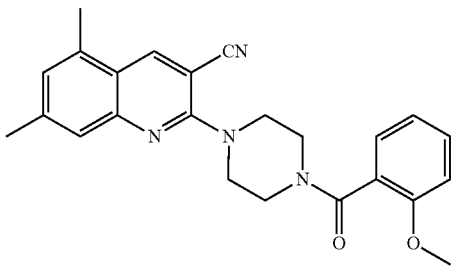 (Compound AW1) | inactive | inactive | 1.0 ± 0.3 | 129 |
| 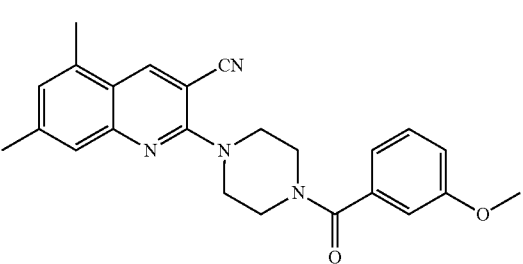 (Compound AW2) | inactive | inactive | 1.2 ± 0.3 | 200 |

TABLE IX-continued
Corrector and potentiator activities
| Compound | Corrector | | Potentiator | |
| --- | --- | --- | --- | --- |
| | EC$_{50}$ (μM) | V$_{max}$ (μM/s) | EC$_{50}$ (μM) | V$_{max}$ (μM/s) |
| 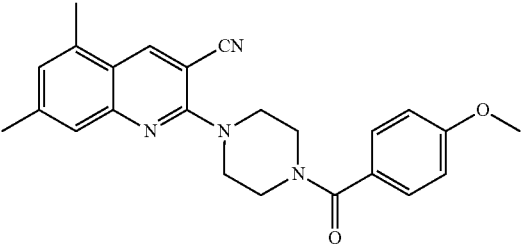 (Compound AW3) | inactive | inactive | 1.3 ± 0.2 | 281 |
| 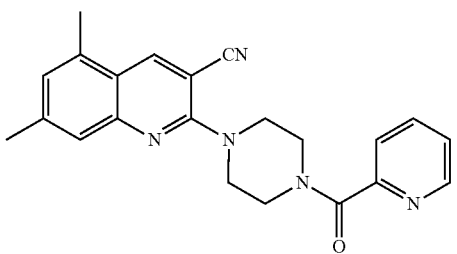 (Compound AW4) | inactive | inactive | 7.4 ± 0.3 | 102 |
| 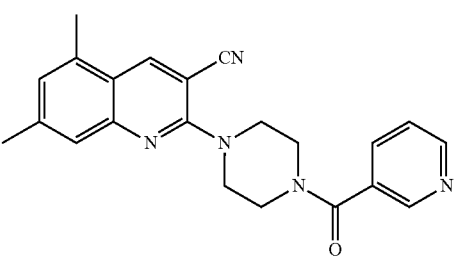 (Compound AW5) | inactive | inactive | inactive | inactive |
| 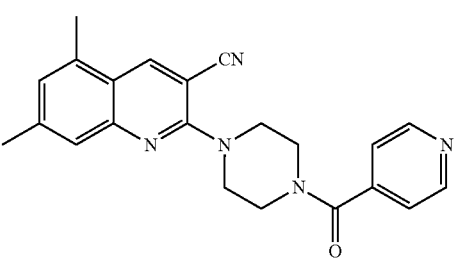 (Compound AW6) | inactive | inactive | inactive | inactive |
| 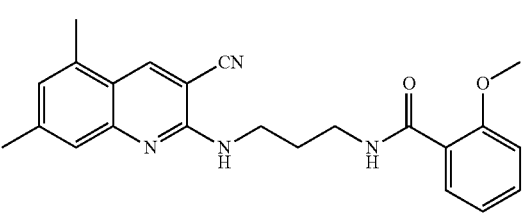 (Compound AW7) | inactive | inactive | 27.6 ± 2.0 | 254 |

TABLE IX-continued
Corrector and potentiator activities
| Compound | Corrector | | Potentiator | |
|---|---|---|---|---|
| | $EC_{50}$ (μM) | $V_{max}$ (μM/s) | $EC_{50}$ (μM) | $V_{max}$ (μM/s) |
| 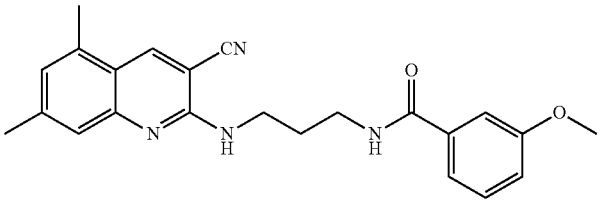<br>(Compound AW8) | 4.6 ± 0.2 | 134 | 4.6 ± 0.4 | 147 |
| 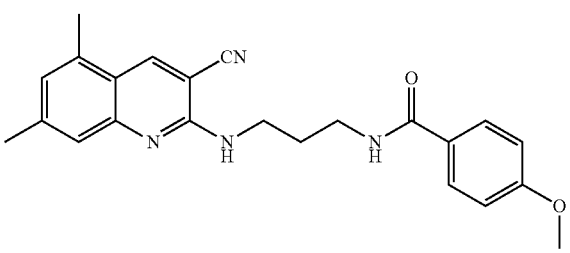<br>(Compound AW9) | 4.3 ± 0.2 | 112 | 5.0 ± 0.2 | 231 |
| 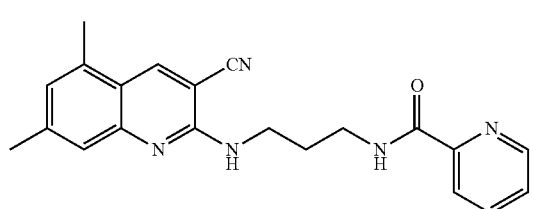<br>(Compound AW10) | inactive | inactive | 6.1 ± 0.2 | 233 |
| 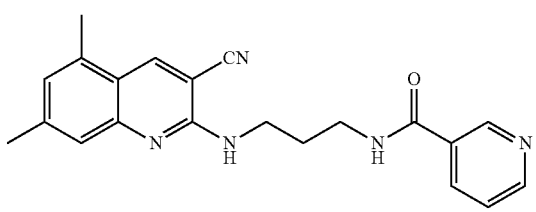<br>(Compound AW11) | 3.0 ± 0.5 | 140 | 16.0 ± 0.3 | 115 |
| 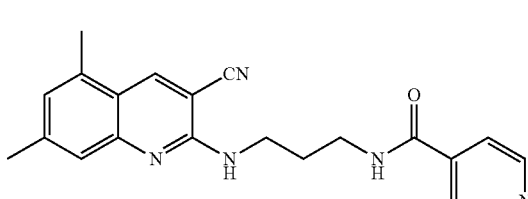<br>(Compound AW12) | 8.2 ± 0.4 | 61 | 13.2 ± 0.4 | 53 |

TABLE IX-continued
Corrector and potentiator activities
| Compound | Corrector | | Potentiator | |
|---|---|---|---|---|
| | EC$_{50}$ (μM) | V$_{max}$ (μM/s) | EC$_{50}$ (μM) | V$_{max}$ (μM/s) |
| 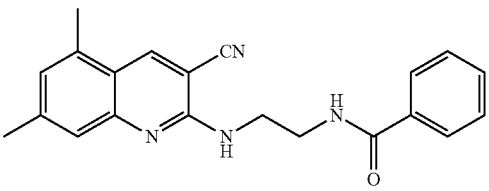 (Compound 100) | inactive | inactive | 10.0 ± 2.0 | 210 |
| 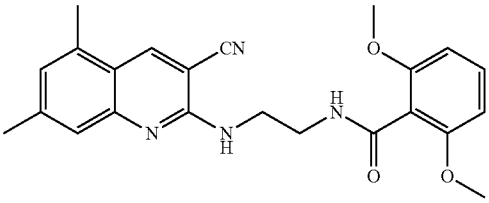 (Compound 101) | 3.7 ± 0.6 | 111 | 11.5 ± 1.0 | 119 |
| 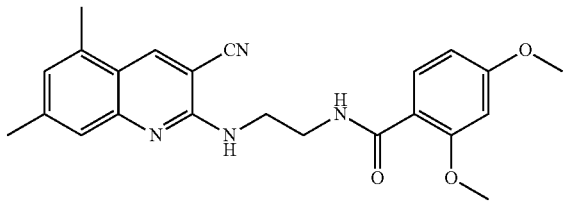 (Compound 102) | 4.2 ± 0.4 | 108 | 55.0 ± 3.5 | 426 |
| 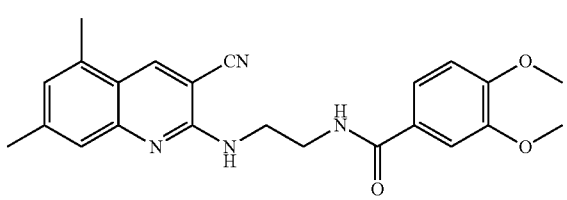 (Compound 103) | 1.5 ± 0.4 | 380 | 48.0 ± 5.0 | 216 |
| 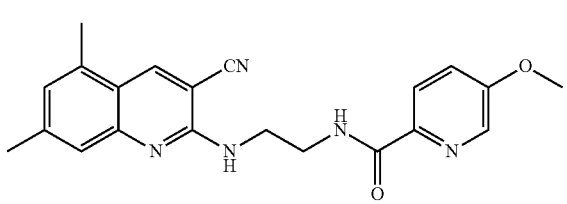 (Compound 110) | 2.7 ± 0.5 | 88 | 3.4 ± 0.5 | 70 |
| 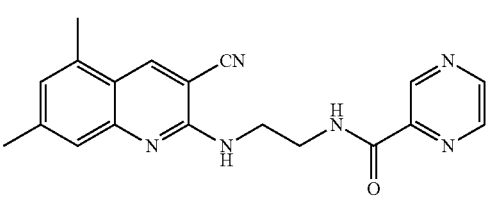 (Compound 111) | 6.7 ± 1.0 | 174 | inactive | inactive |

For further characterization studies, Compound 22 was synthesized in >98% purity in six steps with an overall yield of 52% (see Scheme 1 above). Acetylation of 3,5-dimethylaniline resulted in near quantitative yield of the corresponding acetamide. Formation of the quinoline ring was achieved through reaction with phosphorous oxychloride, giving 2-chloroquinoline carbaldehyde. Condensation of the carbaldehyde with hydroxylamine followed by dehydration using thionyl chloride formed the cyanoquinoline core in 93% yield. Displacement of the chloride by the aminoethane gave amino-cyanoquinoline, which was coupled with m-anisic acid using 1-ethyl-3-(3-dimethylaminopropyl) carbodiimide to give Compound 22 in 73% yield after purification.

Characterization of Compound 22 Corrector Activity

DF508-CFTR expressing FRT cells were incubated with Compound 22 (20 mM) or Corr-4a (10 mM) for 24 h at 27° C. or 37° C. to determine whether Compound 22 corrector activity was additive with low-temperature rescue. As shown in FIG. 3A, Compound 22 and Corr-4a each increased iodide influx at 37° C., with the need for inclusion of genistein. Both compounds substantially increased iodide influx at 27° C. in an approximately additive manner with low-temperature rescue (control, 27° C.), suggesting separate mechanisms for low-temperature rescue and corrector action. In FIG. 3A, iodide influx (SEM, n=4) is shown in the presence of forskolin (20 μM) or forskolin (20 μM) plus genistein (50 μM). *P<0.01 compared to control. To further investigate the forskolin requirement to increase ΔF508-CFTR conductance in the corrector assay, a forskolin concentration-dependence experiment was done in the ΔF508-CFTR-expressing FRT cells after corrector incubation and/or low-temperature rescue. FIG. 3B shows a graph of forskolin dose-response for experiments as in A, measured in the presence of genistein (50 μM). FIG. 3B shows that substantial increase in iodide influx by each of the rescue/corrector maneuvers required relatively high concentrations of forskolin compared to that of <1 μM needed for activation of wildtype CFTR.

Figure 3D:
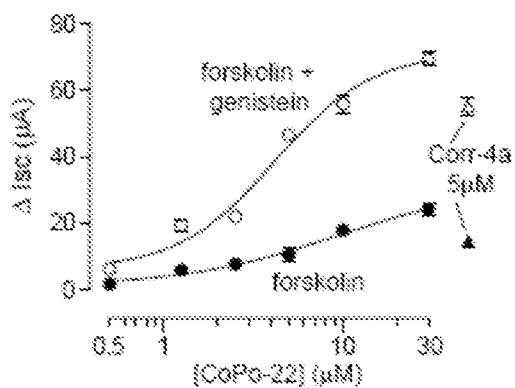
FIG. 3D shows a graph of Compound 22 concentration-dependence deduced from experiments as in FIG. 3C (SEM, n=3-4), according to embodiments of the present disclosure. Fits to single-site binding model are shown.

Short-circuit current was measured as a definitive electrophysiological assay to verify Compound 22 corrector action. Apical membrane chloride current was measured in ΔF508-CFTR expressing FRT cells after basolateral membrane permeabilization and in the presence of a transepithelial chloride gradient (apical, 65 mM; basolateral, 130 mM). In FIG. 3C, incubation with Corr-4a (5 μM) is shown as reference (right). Forskolin (20 μM), genistein (50 μM) and CFTR$_{inh}$-172 (10 μM) were added where indicated. FIG. 3C shows increased apical membrane current when cells were incubated for 18-24 h with increasing concentrations of Compound 22 prior to short-circuit current assay. The increased apical membrane current was fully inhibited by CFTR$_{inh}$-172. The increase in apical membrane current conferred by 5 and 10 μM Compound 22 was comparable to that conferred by 5 μM Corr-4a (FIG. 3C, right). FIG. 3D summarizes Compound 22 concentration dependence data from short-circuit current studies.

Figure 4A:
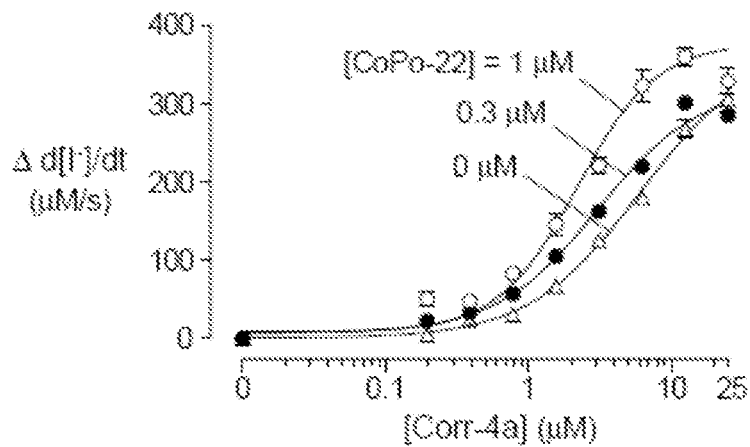
FIG. 4A shows a graph of Corr-4a concentration-dependence of iodide influx (measured with 20 μM forskolin+50 μM genistein) in the presence of indicated (submaximal) concentration of Compound 22 (SEM, n=4), according to embodiments of the present disclosure.
Figure 4B:
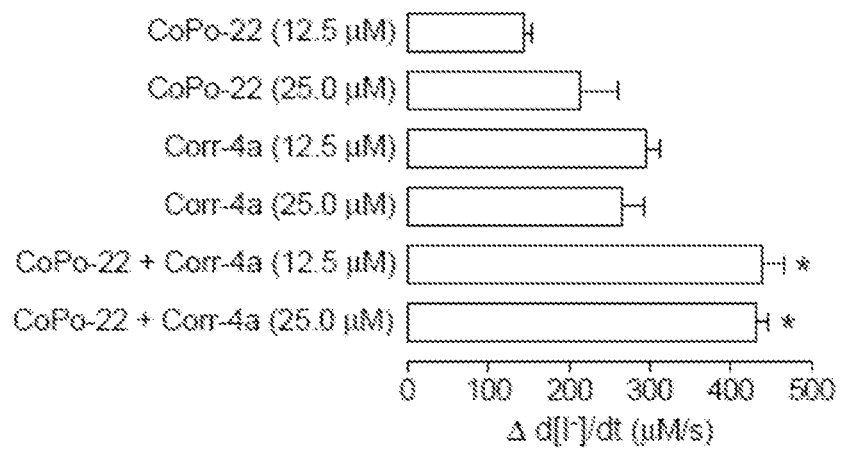
FIG. 4B shows graphs of additivity studies showing iodide influx following incubation with maximal Compound 22 and Corr-4a (SEM, n=4, *P<0.01 compared to Compound 22 or Corr-4a alone), according to embodiments of the present disclosure.

Experiments were performed to investigate possible synergy (e.g., additive corrector efficacy) between Compound 22 and Corr-4a in corrector efficacy. A Corr-4a concentration-dependence experiment was performed at submaximal concentrations of Compound 22 of 0.3 and 1 mM, which did not by itself increase iodide influx significantly. FIG. 4A shows a small though significant increase in iodide influx at relatively high Corr-4a for 1 vs. 0 μM Compound 22. Experiments were also performed to investigate additivity from measurements of iodide influx done after incubation with maximal concentrations of Compound 22 and Corr-4a, alone or in combination. FIG. 4B shows significant additivity of Compound 22 and Corr-4a action, which indicates the independent actions of these correctors.

Figure 4C:
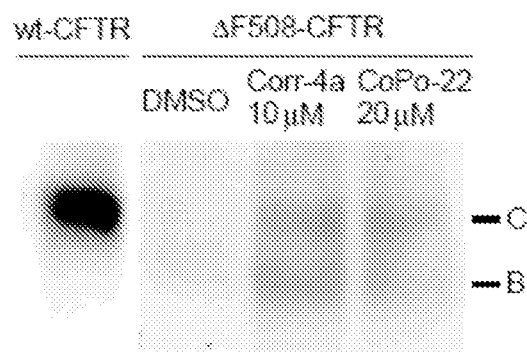
FIG. 4C shows an immunoblot (anti-CFTR antibody) following 24 h incubation at 37° C. of ΔF508-CFTR expressing FRT cells with Corr-4a or Compound 22 (or negative control), according to embodiments of the present disclosure. Bands B (core glycosylated) and C (complex glycosylated) are indicated. For comparison, data is shown for (untreated) FRT cells expressing wildtype CFTR.

The action of Compound 22 as corrector of defective ΔF508-CFTR cellular processing was verified by CFTR immunoblot analysis (FIG. 4C). Wildtype CFTR was detected as a strong band at 170 kDa (band C), corresponding to complex glycosylated CFTR. Little or no band C for ΔF508-CFTR was detected in the absence of corrector, but band C was visualized after 24 h incubation at 37° C. with Compound 22 or Corr-4a. Band B, which corresponds to core-glycosylated ΔF508-CFTR, was also seen.

Characterization of Compound 22 Potentiator Activity

Figure 5A:
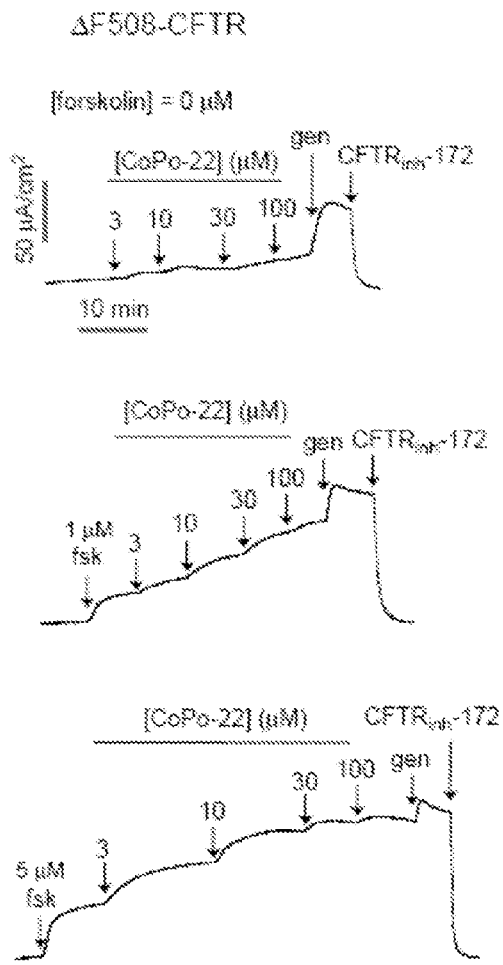
FIGS. 5A and 5B show graphs of short-circuit current measured in FRT cells expressing (FIG. 5A) wildtype CFTR and (FIG. 5B) ΔF508-CFTR, showing responses to indicated forskolin and Compound 22 concentrations, according to embodiments of the present disclosure. Graphs are representative of 2-4 sets of measurements.

Short-circuit current measurements were performed to further characterize Compound 22 potentiator activity in which apical membrane chloride current was measured in ΔF508-CFTR expressing FRT cells, after low-temperature rescue, in response to Compound 22 additions. FIG. 5A shows Compound 22 concentration-dependent increases in apical membrane current seen in the presence of forskolin. ΔF508-CFTR expressing cells were incubated at 27° C. for 24 h prior to measurement. Where indicated, genistein (50 μM) and CFTR$_{inh}$-172 (10 μM) were added. The lack of Compound 22 effect in the absence of forskolin indicates the need for ΔF508-CFTR phosphorylation, as has been found for other potentiators. Genistein produced a small increase in chloride current following maximal Compound 22. CFTR$_{inh}$-172 abolished all chloride current, as expected. Apparent EC$_{50}$ for Compound 22 potentiator activity as measured by short-circuit current was about 10 μM.

Figure 5B:
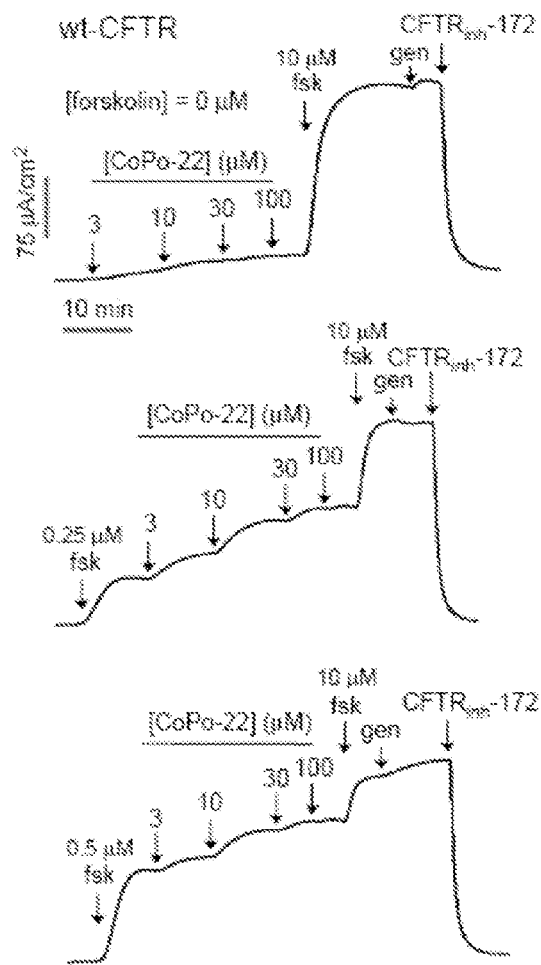

To further investigate Compound 22 potentiator action, short-circuit current was measured in FRT cells expressing wildtype CFTR (FIG. 5B). Studies were done as in FIG. 5A except that low concentrations of forskolin (0-0.5 μM) were used because higher concentrations fully activate wildtype CFTR and thus would mask Compound 22 potentiator action. As found for ΔF508-CFTR, there was little effect of Compound 22 in the absence of forskolin. In each experiment, after Compound 22 additions, 10 μM forskolin was added to fully activate wildtype CFTR, followed by 50 μM genistein, which had little effect, followed by 10 μM CFTR$_{inh}$-172, which inhibited all chloride current. Compound 22 partially activated wildtype CFTR when added after 0.25 or 0.5 μM forskolin, with EC$_{50}$ of about 10 μM.

Potentiator studies were also performed in FRT cells expressing G551D-CFTR, a CF-causing CFTR mutation with defective channel gating but not plasma membrane trafficking. FIG. 6A (top) shows short-circuit current measured in FRT cells G551D-CFTR, showing responses to indicated forskolin and Compound 22 concentrations. Where indicated, genistein (100 μM) and CFTR$_{inh}$-172 (10 μM) were added. Graphs are representative of 3 sets of measurements. FIG. 6A (bottom) shows a plate reader assay of G551D-CFTR chloride conductance showing representative fluorescence quenching curves (inset) and deduced concentration dependence of Compound 22 and genistein potentiator action (SEM, n=4). Measurements were made in the presence of 20 μM forskolin. FIG. 6A shows that Compound 22 functioned as a weak potentiator of G551D-CFTR, producing a smaller increase in chloride current than that produced by genistein.

FIG. 6B shows graphs of potentiator assays done in ΔF508-CFTR expressing A549 cells by YFP/iodide fluorescence quenching as in FIG. 1. Representative fluorescence quenching curves (FIG. 6B (top)) shown with deduced Compound 22 and genistein concentration dependence (FIG. 6B (bottom), SEM, n=4). Fluorescence plate reader assays in FIG. 6B confirmed that Compound 22 activated G551D-CFTR in the presence of forskolin, with lower maximal efficacy than genistein. Apparent $EC_{50}$ for Compound 22 activation of G551-CFTR was about 5 µM (FIG. 6A, bottom), with maximum efficacy lower than that of genistein.

Characterization of Compound 22 Activity in Human A549 Cells

Figure 6C:
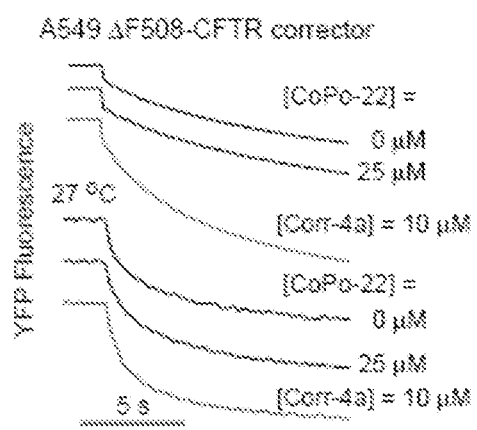
FIG. 6C shows graphs of a corrector assay performed in ΔF508-CFTR expressing A549 cells by YFP/iodide fluorescence quenching, in which cells were incubated with vehicle or indicated correctors at 37° C. (top) or 27° C. (bottom) for 24 h prior to iodide influx measurement, according to embodiments of the present disclosure. Graphs are representative of 3 sets of measurements.

To test whether Compound 22 is active in a different cell background, potentiator and corrector assays were performed in ΔF508-CFTR transfected A549 cells, which are of human lung epithelial origin. FIG. 6B (top) shows that Compound 22 had potentiator activity in the A549 cells comparable to that in FRT cells. Apparent $EC_{50}$ for Compound 22 potentiator activity was about 8 µM (FIG. 6B). However, Compound 22 showed little corrector activity compared to Corr-4a when incubated for 24 h at 37° C. (FIG. 6C, top). Compound 22 was further tested for corrector activity in A549 cells under the low-temperature synergy condition; however, DF508-CFTR was fully activated by forskolin (20 mM) and genistein (50 mM) in this cell model (FIG. 6C, bottom).

Characterization of Corrector/Potentiator Activity for Cyanoquinoline Analogs

Product purification was performed either on an automated flash chromatography system (Combiflash by Teledyne: 35 min of elution with linear gradient from 100% hexane to 100% EtOAc solvent) with silica gel columns or on an HPLC system (Waters: 15 mL/min flow rate, linear gradient elution with 0.1% TFA-containing $H_2O$/MeCN from 5 to 95% MeCN in 20 min, Xterra Prep MS C18 OBD column (19 mm 100 mm), and dual wavelength absorbance detector). NMR spectra ($^1H$ at 600 MHz; $^{13}C$ at 150 MHz) were recorded in $CDCl_3$ solvent on a Varian 600. Chemical shifts were expressed in parts per million relative solvent. Coupling constants were expressed in units of hertz (Hz). Splitting patterns were designated as s (singlet), d (doublet), t (triplet), q (quartet), m (multiplet), and bs (broad singlet). LC/MS (Waters Micromass ZQ) specifications were as follows: electrospray (Þ)) ionization, mass ranging from 100 to 900 Da, 20 V cone voltage. LC: Xterra MS C18 column (2.1 mm 50 mm 3.5 µm), 0.2 mL/min water/acetonitrile (containing 0.1% TFA), 30 min linear gradient 0-100% acetonitrile. The LC/MS UV detector was a diode array with 200-400 nm wavelength range. Purity was based on the peak area percentage of the UV diode array signals. Compound purities were determined by RP-HPLC and were >95%.

ΔF508-CFTR Corrector and Potentiator Activity Assay

Screening procedures. Plate reader activity assay was carried out using a Beckman Coulter platform containing a robotic arm, $CO_2$ incubator containing microplate carousel, plate-washer, liquid handling work station, bar code reader, de-lidding station, plate sealer, and FLUOstar fluorescence plate readers (Optima; BMG LABTECH Gmbh), equipped with dual syringe pumps and 500±10 nm excitation and 535±15 nm emission filters (Chroma Corp.). For the corrector assay, ΔF508-CFTR-expressing FRT cells were grown at 37° C. (90% humidity; 5% $CO_2$) for 18-24 h and then incubated for 18-24 h with 100 µL of medium containing test compounds (0-25 µM final concentration). At the time of the assay, cells were washed with PBS and then incubated for 10 min with PBS containing forskolin (20 µM) and genistein (50 µM). For the potentiator assay, FRT cells were grown at 37° C. (90% humidity; 5% $CO_2$) for 18-24 h and then for 18-24 h at 27° C. At the time of the assay, cells were washed with PBS and then incubated for 10 min with PBS (50 µL) containing forskolin (20 µM) and test compound (0-50 µM final concentration). For both the corrector and potentiator assays, each well was assayed individually for $I^-$ influx by recording fluorescence continuously (200 ms per point) for 2 s (baseline) and then for 12 s after rapid addition of 165 µL PBS in which 137 mM $Cl^-$ was replaced by $I^-$. Initial $I^-$ influx rate was computed by fitting the final 11.5 seconds of the data to an exponential for extrapolation of initial slope, which was normalized for background-subtracted initial fluorescence. All compound plates contained negative controls and positive controls (10 µM Corr-4a for corrector assay; 50 µM genistein for potentiator assay).

Short-circuit current measurements. ΔF508-CFTR-expressing FRT cells were cultured on Snapwell inserts for 7-9 days. For corrector testing, test compounds were incubated with FRT cells 18-24 h at 37° C. prior to measurements. For potentiator testing, the FRT cells were incubated for 18-24 h at 27° C. prior to measurements. The basolateral solution contained 130 mM NaCl, 2.7 mM KCl, 1.5 mM $KH_2PO_4$, 1 mM $CaCl_2$, 0.5 mM $MgCl_2$, 10 mM glucose, and 10 mM Na-HEPES (pH 7.3). In the apical bathing solution, 65 mM NaCl was replaced by Na gluconate, and $CaCl_2$ was increased to 2 mM. Solutions were bubbled with air and maintained at 37° C. The basolateral membrane was permeabilized with 250 µg/ml amphotericin B. Hemichambers were connected to a DVC-1000 voltage clamp (World Precision Instruments Inc.) via Ag/AgCl electrodes and 1 M KCl agar bridges for recording of apical membrane or short-circuit current.

The corrector and potentiator activities for cyanoquinoline analog compounds (e.g., Compounds CP1, CP3, CP4, CP5, CP6, AW1, AW2, AW3, AW4, AW5, AW6, AW7, AW8, AW9, AW10, AW11 and AW12) were assayed for corrector and potentiator activities in ΔF508-expressing FRT cells as described above. Table VIII summarizes corrector and potentiator activities ($EC_{50}$ and $V_{max}$ from concentration-dependence studies). In certain embodiments, compounds with the 1,3-diamino propane tether had activities comparable to the parent 1,2-diamino ethane compounds (e.g., comparing Compound 22 to Compounds AW8, AW9, AW11 and AW12). In some instances, substitution at the 2-position of the arylacid group diminished corrector activity. For instance, moving the methoxy group from the 3-position (e.g., Compound 22) to the 2-position (e.g., Compound CP1) resulted in a decrease of corrector $EC_{50}$ from 2.2 to 11 µM. In certain cases, nitrogen-containing heteroaromatic rings were less active than the corresponding arylacid compounds (e.g., comparing Compound 22 and Compound CP-5). In some instances, replacing the diamino ethylene tether with a piperazine ring diminished or abolished corrector activity (e.g., comparing Compound 22 and Compound AW2). In some cases, replacing the diamino ethylene tether with a piperazine ring diminished or abolished corrector activity, but resulted in significant potentiator activity (e.g., Compounds AW1, AW2 and AW3). In some instances, substitution at the ortho position of the arylamide resulted in a decrease in corrector activity, but an increase in potentiator activity (e.g., Compounds CP1, CP4, AW1, AW4 and AW10). In certain cases, an increase in corrector activity was observed with a compound having an ethylene tether with methoxy substitutions at either the meta (e.g., Compound 22), para (e.g., Compound CP3), or both meta and para (e.g., Compound 103) positions of the arylamide. In certain instances, a similar trend in corrector activity with different methoxy substitutions on the arylamide was observed with compounds having a propylene tether (e.g., Compound AW8 (meta) and Compound AW9 (para) had greater corrector activity than Compound AW7 (ortho)). In certain embodiments, the dual corrector-potentiator activity may depend on the particular scaffold and/or substituents.

Short-circuit current was measured in an electrophysiology assay to verify corrector activity. Apical membrane chloride current was measured in ΔF508-CFTR expressing FRT cells after basolateral membrane permeabilization and in the presence of a transepithelial chloride gradient. An increase in apical membrane current was measured when cells were incubated for 18-24 h with CP-3 (10 µM) prior to the short-circuit current assay. The increased apical membrane current was fully inhibited by CFTR$_{inh}$-172. To assay potentiator activity apical membrane chloride current was measured after low-temperature rescue, in response to CP-3 addition. CP-3 concentration-dependent increases in apical membrane current were measured in the presence of 5 µM forskolin. Genistein produced a small increase in chloride current following maximal CP-3. CFTR$_{inh}$-172 abolished all chloride current. Apparent EC$_{50}$ for CP-3 potentiator effect as measured by short-circuit current was 3 µM.

Figure 8A:
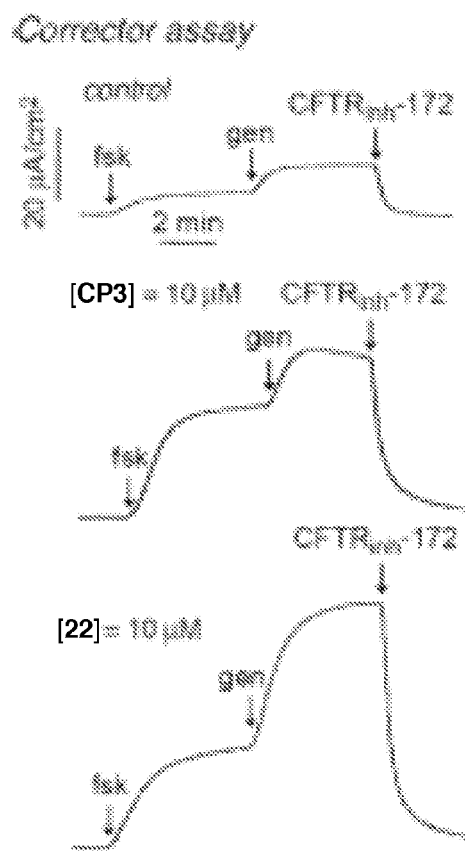
FIGS. 8A and 8B show graphs of short-circuit current measurement of ΔF508-CFTR chloride conductance, according to embodiments of the present disclosure. Measurements of corrector and potentiator activities of Compound CP3 and Compound 22 were done in the presence of an apical-to-basolateral chloride gradient in basolateral membrane-permeabilized cells. Added compounds included forskolin (fsk, 20 μM), genistein (gen, 50 μM), and CFTR$_{inh}$-172 (10 μM).
Figure 8B:
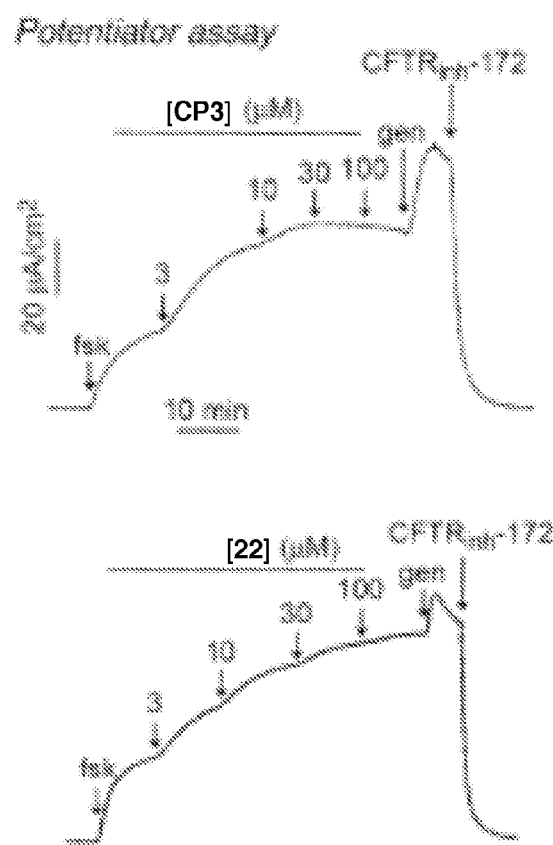

FIGS. 8A and 8B shows representative short-circuit assays of corrector and potentiator activities of Compound CP3, compared to Compound 22, in which apical membrane chloride current was measured in the ΔF508-CFTR expressing FRT cells after basolateral membrane permeabilization and in the presence of a transepithelial chloride gradient. The corrector assay was done by incubation of cells for 18-24 h with test compound at 37° C., followed by addition of forskolin and the potentiator genistein. The potentiator assay was done in low temperature-rescued cells by addition of forskolin followed by test compound. Short-circuit data as in FIGS. 8A and 8B confirmed the results obtained using the fluorescence plate reader assay.

That which is claimed is:

1. A pharmaceutical composition that comprises a compound of formula (I):

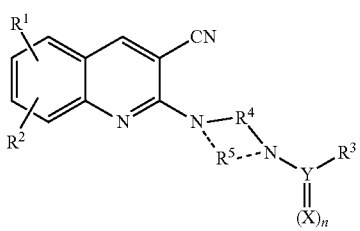

(I)

or salts, solvates, and hydrates thereof, and stereoisomers thereof,
wherein:
$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl;
$R^3$ is selected from alkyl, substituted alkyl, alkylamino, alkylarylamino, aryl, substituted aryl, substituted cycloalkyl, heteroaryl, substituted heteroaryl, heterocyclyl, and substituted heterocyclyl;
$R^4$ is an alkyl or substituted alkyl;
$R^5$ is optional and, if present, is an alkyl or substituted alkyl; and
Y is C or S, with the provisos that:
when Y is C, X is either O or S, and n is 1,
when Y is S, X is O, and n is 2, and
wherein if $R^3$ is alkyl, then Y is S.

2. The pharmaceutical composition of claim 1, wherein $R^1$ is selected from hydrogen, alkyl, substituted alkyl, alkenyl, substituted alkenyl, alkoxy, substituted alkoxy, aryl, and substituted aryl.

3. The pharmaceutical composition of claim 1, wherein $R^1$ is selected from hydrogen, alkyl, substituted alkyl, alkoxy, and substituted alkoxy.

4. The pharmaceutical composition of claim 1, wherein $R^2$ is selected from hydrogen, alkyl, substituted alkyl, alkenyl, substituted alkenyl, alkoxy, substituted alkoxy, aryl, and substituted aryl.

5. The pharmaceutical composition of claim 1, wherein $R^2$ is selected from hydrogen, alkyl, substituted alkyl, alkoxy, and substituted alkoxy.

6. The pharmaceutical composition of claim 1, wherein $R^3$ is selected from aryl, substituted aryl, heteroaryl, and substituted heteroaryl.

7. The pharmaceutical composition of claim 1, wherein the compound is a compound of formula (II):

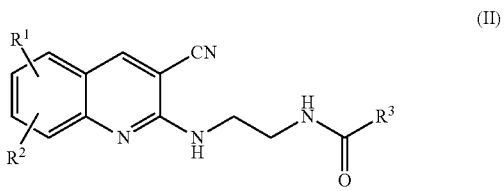

(II)

or salts, solvates, and hydrates thereof, and stereoisomers thereof, wherein:
$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and
$R^3$ is selected from aryl, substituted aryl, cycloalkyl, substituted cycloalkyl, heteroaryl, substituted heteroaryl, heterocyclyl, and substituted heterocyclyl.

8. The pharmaceutical composition of claim 7, wherein $R^1$ is selected from hydrogen, alkyl, substituted alkyl, alkenyl, substituted alkenyl, alkoxy, substituted alkoxy, aryl, and substituted aryl.

9. The pharmaceutical composition of claim 7, wherein $R^1$ is selected from hydrogen, alkyl, substituted alkyl, alkoxy, and substituted alkoxy.

10. The pharmaceutical composition of claim 7, wherein $R^2$ is selected from hydrogen, alkyl, substituted alkyl, alkenyl, substituted alkenyl, alkoxy, substituted alkoxy, aryl, and substituted aryl.

11. The pharmaceutical composition of claim 7, wherein $R^2$ is selected from hydrogen, alkyl, substituted alkyl, alkoxy, and substituted alkoxy.

12. The pharmaceutical composition of claim 7, wherein $R^3$ is selected from aryl, substituted aryl, heteroaryl, and substituted heteroaryl.

13. The pharmaceutical composition of claim 1, wherein the compound is a compound of formula (III):

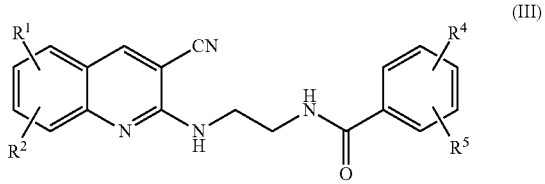

(III)

or salts, solvates, and hydrates thereof, and stereoisomers thereof, wherein:
$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and $R^4$ and $R^5$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl.

14. The pharmaceutical composition of claim 13, wherein $R^1$ is selected from hydrogen, alkyl, substituted alkyl, alkenyl, substituted alkenyl, alkoxy, substituted alkoxy, aryl, and substituted aryl.

15. The pharmaceutical composition of claim 13, wherein $R^1$ is selected from hydrogen, alkyl, substituted alkyl, alkoxy, and substituted alkoxy.

16. The pharmaceutical composition of claim 13, wherein $R^2$ is selected from hydrogen, alkyl, substituted alkyl, alkenyl, substituted alkenyl, alkoxy, substituted alkoxy, aryl, and substituted aryl.

17. The pharmaceutical composition of claim 13, wherein $R^2$ is selected from hydrogen, alkyl, substituted alkyl, alkoxy, and substituted alkoxy.

18. The pharmaceutical composition of claim 13, wherein $R^4$ is selected from hydrogen, alkyl, substituted alkyl, alkenyl, substituted alkenyl, alkoxy, substituted alkoxy, aryl, and substituted aryl.

19. The pharmaceutical composition of claim 13, wherein $R^4$ is selected from hydrogen, alkyl, substituted alkyl, alkoxy, and substituted alkoxy.

20. The pharmaceutical composition of claim 13, wherein $R^5$ is selected from hydrogen, alkyl, substituted alkyl, alkenyl, substituted alkenyl, alkoxy, substituted alkoxy, aryl, and substituted aryl.

21. The pharmaceutical composition of claim 13, wherein $R^5$ is selected from hydrogen, alkyl, substituted alkyl, alkoxy, and substituted alkoxy.

22. The pharmaceutical composition of claim 1, wherein the compound is a compound of formula (IV):

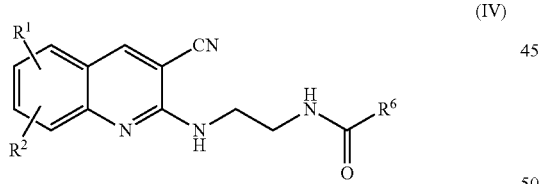

(IV)

or salts, solvates, and hydrates thereof, and stereoisomers thereof, wherein:

$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and $R^6$ is selected from heteroaryl and substituted heteroaryl.

23. The pharmaceutical composition of claim 22, wherein $R^1$ is selected from hydrogen, alkyl, substituted alkyl, alkenyl, substituted alkenyl, alkoxy, substituted alkoxy, aryl, and substituted aryl.

24. The pharmaceutical composition of claim 22, wherein $R^1$ is selected from hydrogen, alkyl, substituted alkyl, alkoxy, and substituted alkoxy.

25. The pharmaceutical composition of claim 22, wherein $R^2$ is selected from hydrogen, alkyl, substituted alkyl, alkenyl, substituted alkenyl, alkoxy, substituted alkoxy, aryl, and substituted aryl.

26. The pharmaceutical composition of claim 22, wherein $R^2$ is selected from hydrogen, alkyl, substituted alkyl, alkoxy, and substituted alkoxy.

27. The pharmaceutical composition of claim 1, wherein the compound is a compound of formula (V):

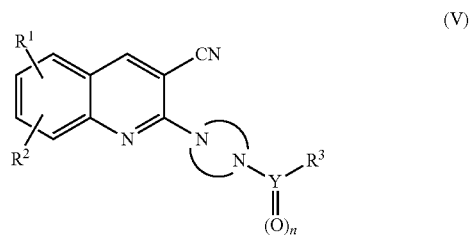

(V)

or salts, solvates, and hydrates thereof, and stereoisomers thereof, wherein:

$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl;

$R^3$ is selected from alkyl, substituted alkyl, aryl, substituted aryl, substituted cycloalkyl, heteroaryl, substituted heteroaryl, heterocyclyl, and substituted heterocyclyl;

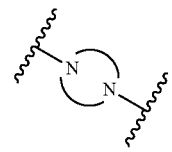

is a heterocylyl or substituted heterocyclyl; and

Y is C or S, with the provisos that:
when Y is C, n is 1,
when Y is S, n is 2, and
wherein if $R^3$ is alkyl, then Y is S.

28. The pharmaceutical composition of claim 27, wherein $R^1$ is selected from hydrogen, alkyl, substituted alkyl, alkenyl, substituted alkenyl, alkoxy, substituted alkoxy, aryl, and substituted aryl.

29. The pharmaceutical composition of claim 27, wherein $R^1$ is selected from hydrogen, alkyl, substituted alkyl, alkoxy, and substituted alkoxy.

30. The pharmaceutical composition of claim 27, wherein $R^2$ is selected from hydrogen, alkyl, substituted alkyl, alkenyl, substituted alkenyl, alkoxy, substituted alkoxy, aryl, and substituted aryl.

31. The pharmaceutical composition of claim 27, wherein $R^2$ is selected from hydrogen, alkyl, substituted alkyl, alkoxy, and substituted alkoxy.

32. The pharmaceutical composition of claim 27, wherein $R^3$ is selected from aryl, substituted aryl, heteroaryl, and substituted heteroaryl.

33. A pharmaceutical composition comprising a compound of formula (VI):

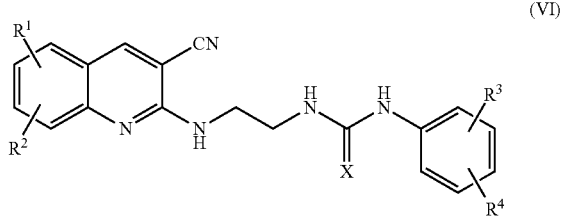

(VI)

or salts, solvates, and hydrates thereof, and stereoisomers thereof, wherein:

$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and $R^3$ and $R^4$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and X is O or S.

34. The pharmaceutical composition of claim 33, wherein $R^1$ is selected from hydrogen, alkyl, substituted alkyl, alkenyl, substituted alkenyl, alkoxy, substituted alkoxy, aryl, and substituted aryl.

35. The pharmaceutical composition of claim 33, wherein $R^1$ is selected from hydrogen, alkyl, substituted alkyl, alkoxy, and substituted alkoxy.

36. The pharmaceutical composition of claim 33, wherein $R^2$ is selected from hydrogen, alkyl, substituted alkyl, alkenyl, substituted alkenyl, alkoxy, substituted alkoxy, aryl, and substituted aryl.

37. The pharmaceutical composition of claim 33, wherein $R^2$ is selected from hydrogen, alkyl, substituted alkyl, alkoxy, and substituted alkoxy.

38. The pharmaceutical composition of claim 33, wherein $R^3$ is selected from hydrogen, alkyl, substituted alkyl, alkenyl, substituted alkenyl, alkoxy, substituted alkoxy, aryl, and substituted aryl.

39. The pharmaceutical composition of claim 33, wherein $R^3$ is selected from hydrogen, alkyl, substituted alkyl, alkoxy, and substituted alkoxy.

40. The pharmaceutical composition of claim 33, wherein $R^4$ is selected from hydrogen, alkyl, substituted alkyl, alkenyl, substituted alkenyl, alkoxy, substituted alkoxy, aryl, and substituted aryl.

41. The pharmaceutical composition of claim 33, wherein $R^4$ is selected from hydrogen, alkyl, substituted alkyl, alkoxy, and substituted alkoxy.

42. The pharmaceutical composition of claim 1, wherein the compound is a compound of formula (VII):

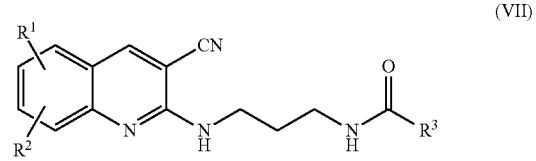

(VII)

or salts, solvates, and hydrates thereof, and stereoisomers thereof, wherein:

$R^1$ and $R^2$ are each independently selected from hydrogen, alkyl, substituted alkyl, alkenyl, substituted alkenyl, alkynyl, substituted alkynyl, alkoxy, substituted alkoxy, aryl, substituted aryl, cycloalkyl, substituted cycloalkyl, heteroaryl, substituted heteroaryl, heterocyclyl, and substituted heterocyclyl; and $R^3$ is selected from aryl, substituted aryl, cycloalkyl, substituted cycloalkyl, heteroaryl, substituted heteroaryl, heterocyclyl, and substituted heterocyclyl.

43. The pharmaceutical composition of claim 42, wherein $R^1$ is selected from hydrogen, alkyl, substituted alkyl, alkenyl, substituted alkenyl, alkoxy, substituted alkoxy, aryl, and substituted aryl.

44. The pharmaceutical composition of claim 42, wherein $R^1$ is selected from hydrogen, alkyl, substituted alkyl, alkoxy, and substituted alkoxy.

45. The pharmaceutical composition of claim 42, wherein $R^2$ is selected from hydrogen, alkyl, substituted alkyl, alkenyl, substituted alkenyl, alkoxy, substituted alkoxy, aryl, and substituted aryl.

46. The pharmaceutical composition of claim 42, wherein $R^2$ is selected from hydrogen, alkyl, substituted alkyl, alkoxy, and substituted alkoxy.

47. The pharmaceutical composition of claim 42, wherein $R^3$ is selected from aryl, substituted aryl, heteroaryl, and substituted heteroaryl.

48. A pharmaceutical composition comprising a compound selected from Compounds 03, 05, 08, 09, 10, 14, 20, CP1, CP3, CP4, CP5, CP6, AW1, AW2, AW3, AW4, AW5, AW6, AW7, AW8, AW9, AW10, AW11, AW12, 100, 101, 102, 103, 110 and 111.

49. A pharmaceutical composition comprising a therapeutically effective amount of a compound of claim 1.

50. A method of treating a subject having a condition associated with a mutant-CFTR, said method comprising administering to the subject a therapeutically effective amount of a pharmaceutical composition comprising a compound of claim 1, wherein said condition is cystic fibrosis.

51. The method of claim 50, wherein the subject, after treatment, has a decrease in mucous or bacterial titer in their lungs, a decrease in coughing or wheezing, a decrease in pancreatic insufficiency, or a decrease in electrolyte levels in their sweat.

52. The method of claim 50, wherein said subject is human.

53. The method of claim 50, wherein the mutant-CFTR is ΔF508-CFTR.

54. A method of increasing ion permeability of a cell producing a mutant-CFTR protein, said method comprising:
contacting said cell with a therapeutically effective amount of a pharmaceutical composition comprising a compound of claim 1, said contacting being effective to increase CFTR-mediated ion permeability of said cell.

55. The method of claim 54, wherein said cell contains a recombinant expression cassette that encodes mutant-CFTR protein.

56. The method of claim 54, wherein said cell contains a genome that encodes said mutant-CFTR protein.

57. The method of claim 54, wherein the mutant-CFTR is ΔF508-CFTR.

* * * * *